(12) United States Patent
Lennek et al.

(10) Patent No.: US 11,945,803 B2
(45) Date of Patent: Apr. 2, 2024

(54) MODULATORS OF RAS GTPase

(71) Applicant: Tosk, Inc., Mountain View, CA (US)

(72) Inventors: Annie L. Lennek, Mountain View, CA (US); Stephen D. Yanofsky, Mountain View, CA (US); Brian D. Frenzel, Mountain View, CA (US); Solomon B. Ungashe, Mountain View, CA (US); William A. Garland, Mountain View, CA (US); Philip Liaw, Mountain View, CA (US)

(73) Assignee: Tosk, Inc., Mountain View, CA (US)

( * ) Notice: Subject to any disclaimer, the term of this patent is extended or adjusted under 35 U.S.C. 154(b) by 296 days.

(21) Appl. No.: 17/260,711

(22) PCT Filed: Aug. 6, 2019

(86) PCT No.: PCT/US2019/045315
§ 371 (c)(1),
(2) Date: Jan. 15, 2021

(87) PCT Pub. No.: WO2020/033413
PCT Pub. Date: Feb. 13, 2020

(65) Prior Publication Data
US 2021/0261532 A1 Aug. 26, 2021

Related U.S. Application Data

(60) Provisional application No. 62/715,505, filed on Aug. 7, 2018.

(51) Int. Cl.
C07D 403/14 (2006.01)
C07D 413/12 (2006.01)

(52) U.S. Cl.
CPC ......... *C07D 403/14* (2013.01); *C07D 413/12* (2013.01)

(58) Field of Classification Search
CPC .. C07D 403/12; C07D 403/14; C07D 413/12; C07D 271/06
See application file for complete search history.

(56) References Cited

U.S. PATENT DOCUMENTS

2018/0086752 A1   3/2018   Rabizadeh et al.

FOREIGN PATENT DOCUMENTS

WO   WO2005012256 A1   2/2005
WO   WO2017023133 A2   2/2017

OTHER PUBLICATIONS

Chemical Abstract compounds, STN express RN 1269064-16-5 (Entered STN: Mar. 21, 2011) See the structure.

(Continued)

*Primary Examiner* — Kortney L. Klinkel
*Assistant Examiner* — Padmaja S Rao
(74) *Attorney, Agent, or Firm* — James J. Diehl; Bret E. Field; Bozicevic, Field & Francis LLP

(57) ABSTRACT

RAS modulating compounds and methods of using the same are provided. The compounds find use in modulating the activity of a target RAS in a sample. The target RAS can be a mutant RAS that is implicated in a disease of interest. In some cases, the subject compounds can inhibit the growth of cancer cells whose progression is driven by kRAS or a mutated kRAS. Methods of treating a subject for a RAS driven disease including administering a therapeutically effective amount of the subject compound are provided. Also provided are pharmaceutical compositions and kits which include the subject compounds.

9 Claims, 10 Drawing Sheets

(56) References Cited

OTHER PUBLICATIONS

Chemical Abstract compounds, STN express RN 2109536-59-4 (Entered STN: Aug. 7, 2017) See the structure.
Chemical Abstract compounds, STN express RN 1360253-07-1 (Entered STN: Mar. 7, 2012) See the structure.
McCarthy et al., Discovery of High-Affinity Noncovalent Allosteric KRAS Inhibitors That Disrupt Effector Binding, ACS Omega, Feb. 2019, vol. 4, p. 2921-2930.
Moore et al., RAS-targeted therapies: is the undruggable drugged?, Nature Reviews Drug Discovery, Jun. 2020, vol. 19, p. 533-552.

A

B

A

B

A

B

A

B

A

B

*p<0.028

MODULATORS OF RAS GTPase

CROSS-REFERENCE TO RELATED APPLICATION

Pursuant to 35 U.S.C. § 119 (e), this application claims priority to the filing date of U.S. Provisional Patent Application Ser. No. 62/715,505 filed Aug. 7, 2018; the disclosure of which application is herein incorporated by reference.

GOVERNMENT RIGHTS

This invention was made with government support under grant No. 1 R43CA189549-01, awarded by the Department of Health and Human Services. The government has certain rights in the invention.

INTRODUCTION

The RAS family of proteins represents a group of 189 amino acid (21 kDa molecular mass), closely related, monomeric, globular GTPases which associate with the plasma membrane and bind either guanosine diphosphate (GDP) or guanosine triphosphate (GTP). The proteins act as molecular switches in signal transduction in cells. When bound to GDP, RAS is in its off (resting) position and is inactive. When activated by its cell surface growth factor EGF, RAS exchanges bound GDP for GTP. With GTP bound, RAS is "switched on" and can interact with and activate other proteins including its "downstream targets," such as the pro-growth Ras-Raf-MEK-ERK pathway. The RAS protein itself has a very low intrinsic ability to turn itself off by hydrolyzing GTP back to GDP. Switching RAS off requires extrinsic proteins termed GTPase-activating proteins (GAPs) that interact with RAS and greatly accelerate the conversion of GTP to GDP. Any mutation in RAS which affects its ability to interact with a GAP or to convert GTP back to GDP can result in a prolonged activation of the protein and consequently provide a prolonged signal to cells to proliferate. Because these signals result in cell growth and division, overactive RAS signaling can lead to cancer. Conversely, compounds that bind the inactive GDP-bound RAS and inhibit the exchange of GDP for GTP inhibit RAS activity by preventing its association with, and activation of, its downstream targets. Compounds that inhibit the association of activated GTP-bound RAS with its downstream targets such as the RAF family of proteins also inhibit RAS-induced promotion of cell growth and proliferation and are of interest as potential anti-cancer drugs.

Mutations in any one of the three main isoforms of RAS (hRAS, nRAS, or kRAS) genes are among the most common events in human tumorigenesis. About 30% of all human tumors are found to carry some mutation in RAS. Remarkably, RAS mutations are detected in 30% of tumors and of these mutations 86% are in kRAS. By comparison, the rates of oncogenic mutation occurring in the nRAS and hRAS family members are much lower (11% and 3% respectively). The most common kRAS mutations are at residue G12 and G13 in the P-loop and at residue Q61. kRAS is mutated in 61% of pancreatic cancers, 43% of colon cancers, 21% of endometrial cancers, 26% of lung adenocarcinomas, eg, non-small cell lung carcinoma, 3% of skin cancers, 4% of acute myeloid leukemia (AML) liquid tumors and in 1% or so of multiple myeloma cancers.

SUMMARY

RAS modulating compounds and methods of using the same are provided. The compounds find use in modulating the activity of a target RAS in a sample. The target RAS can be a mutant RAS that is implicated in a disease of interest. In some cases, the subject compounds can inhibit the growth of cancer cells whose progression is driven by kRAS or a mutated kRAS. Methods of treating a subject for a RAS driven disease including administering a therapeutically effective amount of the subject compound are provided. Also provided are pharmaceutical compositions and kits which include the subject compounds.

DEFINITIONS

Figure 1:
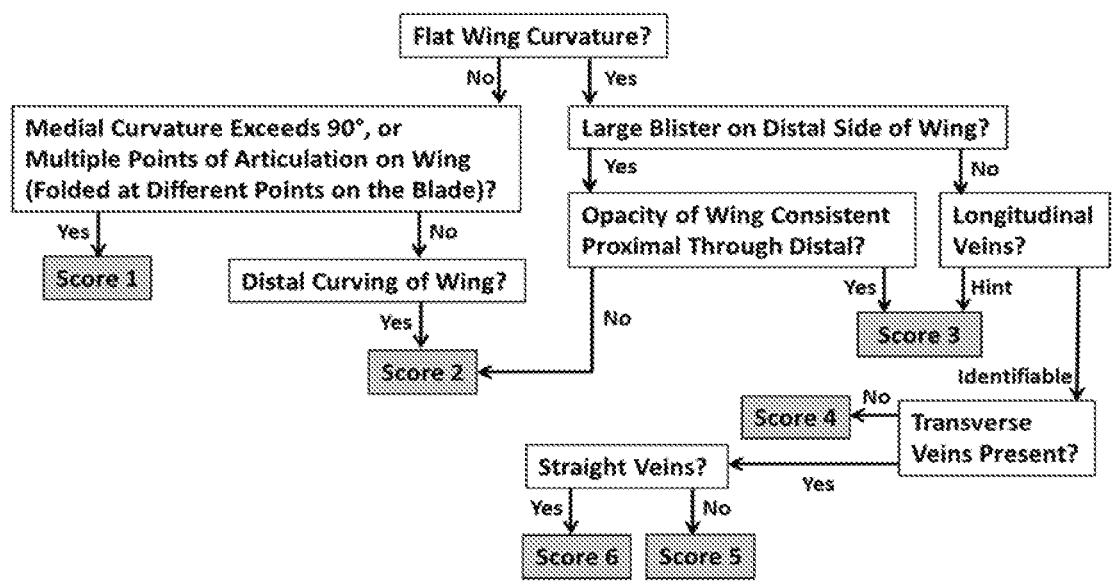
FIG. 1 shows a schematic of a scoring tree employed to test for phenotype reversal in fly assays. Each wing from mutant flies receiving treatment with either water or compound received a score from two independent scorers according to the scheme outlined in the schematic. The analysis of the scores given to the compound group was compared to the scores given for the control (water) group.

Unless defined otherwise, all technical and scientific terms used herein have the same meaning as is commonly understood by one of skill in the art to which this invention belongs. All patents and publications referred to herein are incorporated by reference. As used in the specification and claims, the singular form "a", "an" and "the" include plural references unless the context clearly dictates otherwise.
ALB is albumin which is the most abundant blood plasma protein and is produced in the liver and forms a large proportion of all plasma protein. Its main function is to regulate the colloidal osmotic pressure of blood.

Alkyl by itself or as part of another substituent refers to a monovalent saturated aliphatic hydrocarbon group. This term includes linear, cyclic, or branched groups or a combination thereof. The group can have the number of carbon atoms designated (e.g., C1-C8 means one to eight carbon atoms). In some cases, an alkyl group has from 1 to 10 carbon atoms, such as 1 to 6 carbon atoms, or 1 to 5, or 1 to 4, or 1 to 3 carbon atoms. Examples of alkyl groups include, but are not limited to, methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc.
Structures for a few exemplary alkyl groups are provided in Table 1 below.

TABLE 1

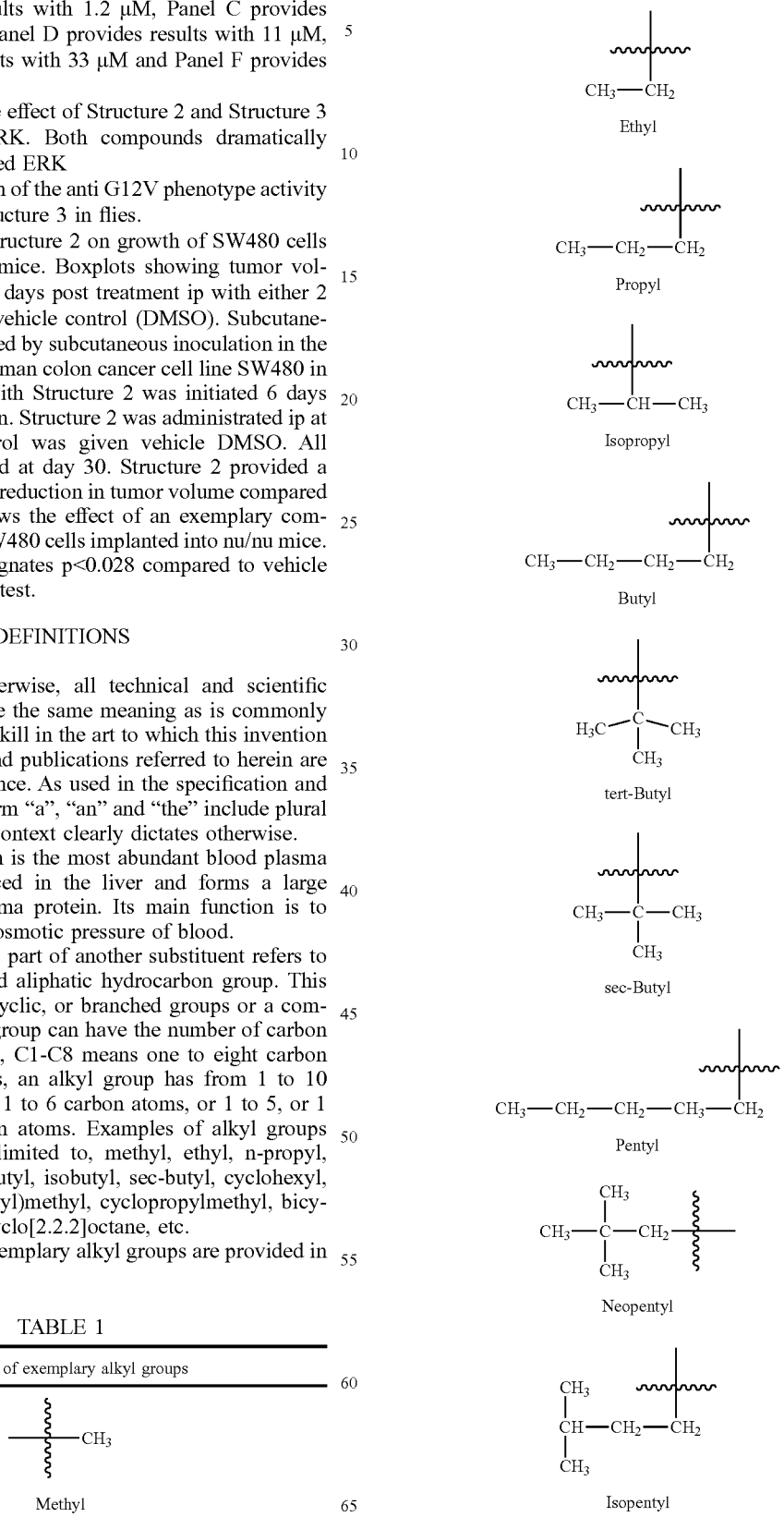

TABLE 1-continued

Structure of exemplary alkyl groups

Hexyl

Isohexyl

Alkyl groups can be substituted or unsubstituted, unless otherwise indicated.

The term "substituted alkyl" refers to an alkyl group as defined herein wherein one or more carbon atoms in the alkyl chain have been optionally replaced with a heteroatom such as O—, N—, S—, —S(O)$_n$— (where n is 0 to 2), —NR— (where R is hydrogen or alkyl) and having from 1 to substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, SO$_2$-heteroaryl, and —NRaRb, wherein R' and R" may be the same or different and are chosen from hydrogen, optionally substituted alkyl, cycloalkyl, alkenyl, cycloalkenyl, alkynyl, aryl, heteroaryl and heterocyclic. Examples of substituted alkyl include haloalkyl, thioalkyl, aminoalkyl, and the like.

Alkenyl refers to an unsaturated hydrocarbon group which may be linear, cyclic or branched or a combination thereof. Alkenyl groups with 2-8 carbon atoms are preferred. The alkenyl group may contain 1, 2 or 3 carbon-carbon double bonds. Examples of alkenyl groups include ethenyl, n-propenyl, isopropenyl, n-but-2-enyl, n-hex-3-enyl, cyclohexenyl, cyclopentenyl and the like. Alkenyl groups can be substituted or unsubstituted, unless otherwise indicated.

Aryl or Ar refers to a polyunsaturated, aromatic hydrocarbon group having a single ring (bicyclic) or multiple rings (preferably bicyclic) which can be fused together or linked covalently. In some cases, an Aryl group has 6 to 18 carbon atoms, such as 6-10 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. Examples of aryl groups include, but are not limited to, phenyl and naphthalene-1-yl, naphthalene-2-yl, biphenyl and the like. Aryl groups can be substituted or unsubstituted, unless otherwise indicated. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. The structures of a few exemplary aryl groups are provided in Table 2 below.

TABLE 2

Examples of aryl groups

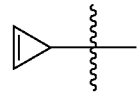

Cyclopropenyl

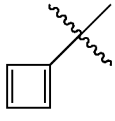

Cyclobuta-1,3-dienyl

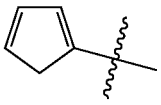

Cyclopenta-1,3-dienyl

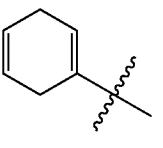

Cyclohexa-1,4-dienyl

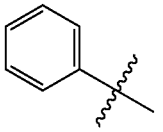

Benzyl

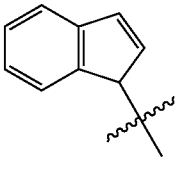

1H-indenyl

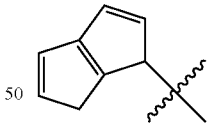

1,6-dihydropentalenyl

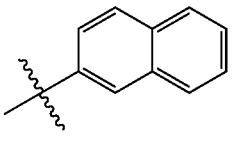

Napthylenyl

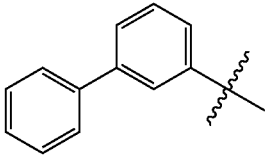

1,1'-Biphenyl

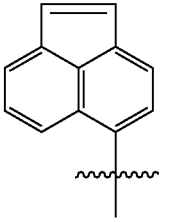

Acenaphthylenyl

TABLE 2-continued

Examples of aryl groups

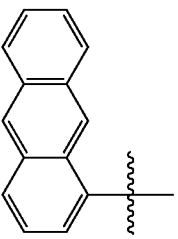
Anthracenyl

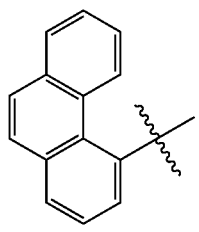
Phenanthrenyl

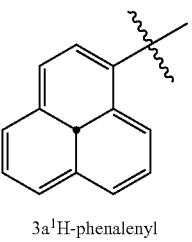
3a¹H-phenalenyl

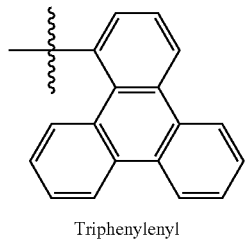 [SMILES: *c1cccc2c3ccccc3c3ccccc3c12]
Triphenylenyl

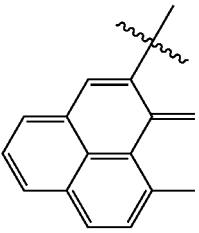
Pyrenyl

ALP is alkaline phosphatase which is a protein found in all body tissues. Tissues with higher amounts of ALP include the liver, bile ducts, and bone.

AMY is Amylase, which is an enzyme that helps digest carbohydrates. It is made in the pancreas and the glands that make saliva. When the pancreas is diseased or inflamed, amylase releases into the blood.

ANOVA is analysis of variance, which is a collection of statistical models used to analyze the differences among group means and their associated procedures (such as "variation" among and between groups), developed by statistician and evolutionary biologist Ronald Fisher.

AUC is the area under the curve, which is the area under the curve (mathematically known as definite integral) in a plot of concentration of drug in blood plasma against time in the field of pharmacokinetics. Typically, the area is computed starting at the time the drug is administered and ending when the concentration in plasma is negligible. In practice, the drug concentration is measured at certain discrete points in time and the trapezoidal rule is used to estimate AUC.

BUN stands for blood urea nitrogen. Urea nitrogen is what forms when protein breaks down. Increased BUN levels suggest impaired kidney function. This may be due to acute or chronic kidney disease, damage, or failure.

Cl is Clearance. Drug clearance defines how much drug should be administered, how frequently to dose a patient, and how two interacting drugs will affect a patient. The primary PK parameter clearance is very similar to its friend, volume of distribution. Clearance (Cl) is a proportionality factor that relates the concentration of drug measured in the body to the rate of elimination.

CRE is creatinine which is a breakdown product of creatine phosphate in muscle, and is usually produced at a fairly constant rate by the body. Serum creatinine is an important indicator of renal health because it is an easily measured byproduct of muscle metabolism that is excreted unchanged by the kidneys.

DIRAS is diverse RAS, which is a distinct branch of the functionally diverse RAS superfamily of monomeric GTPases.

DMEM is Dulbecco's Modified Eagle Medium. It is a modification of Basal Medium Eagle (BME) that contains a four-fold higher concentration of amino acids and vitamins, as well as additional supplementary components. The original DMEM formula contains 1000 mg/L of glucose and was first reported for culturing embryonic mouse cells.

Effective amount or therapeutically effective amount refers to an amount of a compound sufficient to effect the intended application, such as an amount sufficient to treat a specified disorder or disease or one or more of its symptoms and/or to prevent the occurrence of the disease or disorder. The therapeutically effective amount may vary depending upon the intended treatment application (e.g., in vivo), or the subject and disease condition being treated, e.g., the weight and age of the subject, the severity of the disease condition, the manner of administration and the like, which can readily be determined by one of ordinary skill in the art.

Enantiomer. Enantiomers are stereoisomers that are non-superimposable mirror images. A molecule with 1 chiral carbon atom exists as 2 stereoisomers termed enantiomers. Enantiomers differ in their configuration (R or S) at the stereogenic center.

ERAS is RAS expressed by ES cells. This is a constitutively active member of the small GTPase RAS protein family. The encoded protein activates the phosphatidylinositol 3-kinase signal transduction pathway in undifferentiated stem cells, but is not expressed in differentiated cells. This gene may be involved in cancer and chemotherapy resistance.

ERK is extracellular-signal-regulated kinase which is a widely expressed protein kinase and intracellular signaling molecules involved in functions including the regulation in differentiated cells of meiosis, mitosis, and post-mitotic action.

F is bioavailability. Bioavailability simply means the fraction of administered drug that reached the systemic circulation (blood). It can range from 0% (no drug) to 100% (all of the administered drug).

GEM is GTP binding protein overexpressed in skeletal muscle. The protein belongs to the RAD/GEM family of GTP-binding proteins. It is associated with the inner face of the plasma membrane and could play a role as a regulatory protein in receptor-mediated signal transduction. Alternative splicing occurs at this locus and two transcript variants encoding the same protein have been identified.

G Domain is a highly conserved domain common to all GTPases that is located on the largest of the G proteins three subunits, the α unit. The two smaller subunits are the β and γ units.

GLOB is globulin. It is a generic term used to describe a set of sixty proteins including the antibodies or gamma globulins and protein-carbohydrate compounds known as glycoproteins.

GLU is a type of sugar, called glucose. Glucose comes from carbohydrate foods. It is the main source of energy used by the body.

GRA is granulocytes. Granulocytes are WBCs that contain cytoplasmic granules. These include neutrophils, eosinophils, and basophils. These cells are produced in the bone marrow. Increased granulocyte counts normally indicate a neutrophilia, and decreased counts indicate a neutropenia.

GTPase refers to a large family of hydrolase enzymes that bind and hydrolyze GTP.

Halo or halogen, by itself or as part of a substituent refers to a chlorine, bromine, iodine, or fluorine atom. Additionally, "haloalkyl", as a substituted alkyl group, refers to a monohaloalkyl or polyhaloalkyl group, most typically substituted with from 1-3 halogen atoms. Examples include, but are not limited to, 1-chloroethyl, 3-bromopropyl, trifluoromethyl and the like.

Heterocyclyl refers to a saturated or unsaturated non-aromatic group containing at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like. Heterocyclic groups can be monocyclic, or can be fused or linked covalently to an aryl or heteroaryl ring system.

Heteroaryl refers to an aromatic group containing at least one heteroatom. Examples include, but are not limited to, pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl. Preferred heteroaryl groups are those having at least one aryl ring nitrogen atom, such as quinolinyl, quinoxalinyl, purinyl, benzimidazolyl, benzopyrazolyl, benzotriazolyl, benzothiazolyl, indolyl, quinolyl, isoquinolyl and the like. Preferred 6-ring heteroaryl systems include pyridyl, pyridazinyl, pyrazinyl, pyrimidinyl, triazinyl and the like. Preferred 5-ring heteroaryl systems include isothiazolyl, pyrazolyl, imidazolyl, thienyl, furyl, triazolyl, tetrazolyl, oxazolyl, isoxazolyl, oxadiazolyl, thiadiazolyl, pyrrolyl, thiazolyl and the like.

Heterocyclyl and heteroaryl groups can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Heterocyclyl and heteroaryl groups can be substituted or unsubstituted, unless otherwise indicated. For substituted groups, the substitution may be on a carbon or heteroatom. The structures of a few exemplary heterocyclyls are shown in Table 3.

TABLE 3

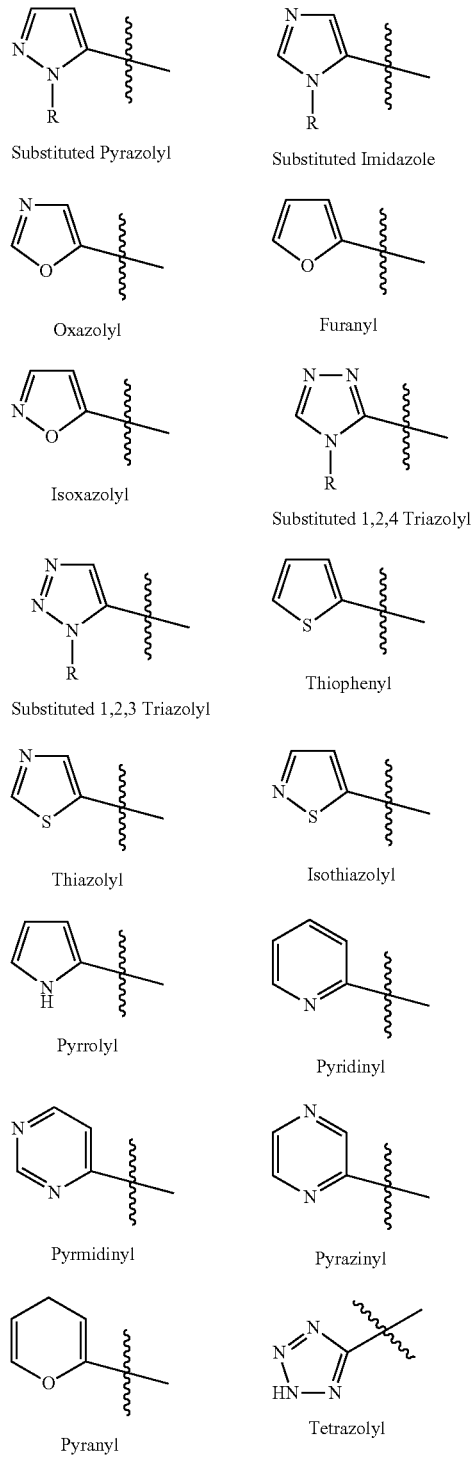

Examples of heterocyclyls

Substituted Pyrazolyl

Substituted Imidazole

Oxazolyl

Furanyl

Isoxazolyl

Substituted 1,2,4 Triazolyl

Substituted 1,2,3 Triazolyl

Thiophenyl

Thiazolyl

Isothiazolyl

Pyrrolyl

Pyridinyl

Pyrmidinyl

Pyrazinyl

Pyranyl

Tetrazolyl

Substituents of interest for substituted alkyl, substituted alkenyl, and substituted alkynyl groups include, but are not limited to, halogen, —ON, —CO₂R', —C(O)R', —C(O)NR'R", oxo (=O), —OR', —OC(O)R', —OC(O)NR'R"— NO₂, —NR'C(O)R', —NR'''C(O)NR'R", —NR'R", —NR'CO₂R", —NR'S(O)₂R''', —SR', —S(O)R", —S(O)₂R', —S(O)₂NR'R", —SiR'R" R''', —N₃, substituted or unsubstituted $O_{6-10}$ aryl, substituted or unsubstituted 5- to 10-membered heteroaryl, and substituted or unsubstituted 3- to 10-membered heterocyclyl, in a number ranging from zero to (2m'+1), where m' is the total number of carbon atoms in such radical.

Substituents of interest for substituted aryl, substituted heteroaryl and substituted heterocyclyl groups include, but are not limited to, halogen, —ON, —CO$_2$R', —C(O)R', —C(O)NR'R", oxo, —OR', —OC(O)R', —OC(O)NR'R", —NO$_2$, —NR'C(O)R", —NR'C(O)NR"R"', —NR'R", —NR'CO$_2$R", —NR'S(O)$_2$R", —SR', —S(O)R', —S(O)$_2$R', —S(O)$_2$NR'R", —NR'—C(NHR").dbd.NR"', —SiR'R" R"', —N$_3$, substituted or unsubstituted $C_{1-8}$ alkyl group, substituted or unsubstituted $C_{6-10}$ aryl group, substituted or unsubstituted 5- to 10-membered heteroaryl, and substituted or unsubstituted 3- to 10-membered heterocyclyl, in a number ranging from zero to the total number of open valences on the aromatic ring system. As used above, R', R" and R"' each independently refer to a variety of groups including hydrogen, substituted or unsubstituted $C_{2-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, substituted or unsubstituted arylalkyl, and substituted or unsubstituted aryloxyalkyl. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl).

HCT stands for hematocrit. It is used interchangeably to indicate the percent of red blood cells in a unit of whole blood. When a blood sample is centrifuged (spun hematocrit), it separates into three layers: an upper layer of plasma, a middle layer of WBCs and thrombocytes (buffy coat), and a bottom layer of packed RBCs. Technically, the hematocrit is a measure of all cellular elements of blood (WBCs, thrombocytes, and RBCs), but by common usage it has become synonymous with packed cell volume.

HGB is hemoglobin which is the oxygen-carrying pigment formed by developing RBCs in the bone marrow. The hemoglobin value of a blood sample is approximately one-third of the packed cell volume. Variations from this indicate a laboratory error, hemolysis, or abnormalities such as Heinz bodies or lipemia. Altered hemoglobin can form Heinz bodies or crystals. Determination of hemoglobin provides no clinical advantage over measurement of the packed cell volume, other than allowing the determination of mean corpuscular hemoglobin and mean corpuscular hemoglobin concentration.

kDa is kilo Dalton. Dalton is the standard unit that is used for indicating mass on an atomic or molecular scale.

LYM is lymphocytes. Lymphocytes in the blood are a mixed population of B-cells and T-cells. They are the major cellular component of immunity in the body. B-lymphocytes synthesize antibodies that are responsible for humoral immunity. T-lymphocytes are the principal component of cellular immunity. Lymphocytes also participate in immune regulation and surveillance, and some are cytotoxic.

MEK, mitogen-activated protein kinase also known as MAP2K, MEK, MAPKK, is a kinase enzyme which phosphorylates mitogen-activated protein kinase (MAPK).

MET, methyl, is a chemical group with a structure CH$_3$—.

MCV is mean corpuscular volume which is the average volume of a single RBC. It is determined by direct measurement with an electronic cell counter such as the analyzer. Increases are usually due to reticulocytes and indicate a responsive anemia.

MCH is mean corpuscular hemoglobin. It is the average amount of hemoglobin in each RBC. This calculated index is increased with hemolysis. Decreases are termed hypochromasia, and are seen with reticulocytosis and iron deficiency.

MCHC is mean corpuscular hemoglobin concentration. MCHC measures the mean concentration of hemoglobin in RBCs. Increases are usually caused by hemolysis. Decreases are termed hypochromasia and are seen in reticulocytosis and iron deficiency anemia.

MON is monocytes. They are the immature blood stage of tissue macrophages. Increased numbers occur in response to inflammation. Their main function is phagocytosis of foreign material, cellular debris, and pathogens that are not effectively controlled by neutrophils. They engulf intracellular organisms and those causing a granulomatous inflammatory response. They are effective scavengers, removing tissue debris, cellular remnants, and foreign material. Monocytes are also active in regulating the immune response, processing antigen, and activating killer cells and macrophages. Monocytes are the most commonly misidentified leukocyte in blood smears, often being placed into the lymphocyte category.

MPV is mean platelet volume. The MPV is a machine calculation of platelet size. In thrombocytopenic dogs, increased mean platelet volume gives indirect evidence of increased megakaryocyte response. High mean volume (>12 fl) indicates increased response, but decreased volume (<12 fl) is not accurate in predicting lack of bone marrow megakaryocyte production.

MRAS is muscle RAS oncogene homolog. This gene encodes a member of the RAS family of small GTPases. These membrane-associated proteins function as signal transducers in multiple processes including cell growth and differentiation, and dysregulation of RAS signaling has been associated with many types of cancer. The encoded protein may play a role in the tumor necrosis factor-alpha and MAP kinase signaling pathways. Alternatively spliced transcript variants encoding multiple isoforms have been observed for this gene.

MRT is mean residence time. For the pharmaceutical field, mean residence time often refers to the amount of time that a drug spends in the body. This is dependent on an individual's body size, the rate at which the drug will move through and react within the person's body, and the amount of the drug administered.

MYH is a base excision repair gene responsible for a hereditary colon cancer syndrome. MYH is located on the short (p) arm of chromosome 1 in region 1p34.3-p32.1. MYH encodes an enzyme that removes the base adenine from mispairs (with 8-oxoguanine) that arise during the replication of oxidized DNA.

NKIRAS is NFKB inhibitor interacting RAS-like. Among its related pathways are NF-KappaB Family Pathway and TNF-alpha/NF-kB Signaling Pathway. It is also related to GTP binding and GTPase activity.

NSCLC is non-small-cell lung carcinoma. NSCLC is any type of epithelial lung cancer other than small cell lung carcinoma. As a class, NSCLCs are relatively insensitive to chemotherapy, compared to small cell carcinoma. When possible, they are primarily treated by surgical resection with curative intent, although chemotherapy is increasingly being used both pre-operatively and post-operatively.

PBS is phosphate-buffered saline. PBS is a buffer solution commonly used in biological research. It is a water-based salt solution containing sodium phosphate, sodium chloride and, in some formulations, potassium chloride and potassium phosphate.

PCT is procalcitonin which is a marker of inflammatory response and is stimulated by bacterial products (endotoxins/LPS) and cytokines (IL-1,IL-2, IL-6, TNFα). The exact biological role of PCT remains largely unknown, however, recent data suggests that PCT may play a pathologic role in sepsis.

PDWc is platelet distribution width count. Platelet distribution width is a measure of platelet anisocytosis (variation in size). A mixture of large and small platelets can give a normal mean platelet volume (MPV) but a high PDW. This would indicate active platelet release.

Pharmaceutically acceptable carrier, diluent, or excipient is a carrier, diluent, or excipient compatible with the other ingredients of the formulation and not deleterious to the recipient thereof.

Pharmaceutically-acceptable salt refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts. The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

PHOS is phosphorus. It is a mineral the body needs to build strong bones and teeth. It is important for nerve signaling and muscle contraction PI3K is phosphatidylinositol-4,5-bisphosphate 3-kinase. PI3K(s) are a family of enzymes involved in cellular functions such as cell growth, proliferation, differentiation, motility, survival and intracellular trafficking, which in turn are involved in cancer.

PLT is platelet. Platelets are small, flat disks produced by megakaryocytes. They adhere to exposed sub-endothelial collagen within seconds of injury to form a hemostatic plug. Low platelet counts predispose an animal to hemorrhage.

RAF are a family of three serine/threonine-specific protein kinases that are related to retroviral oncogenes. RAF kinases participate in the RAS-RAF-MEK-ERK signal transduction cascade, also referred to as the mitogen-activated protein kinase (MAPK) cascade. Activation of RAF kinases requires interaction with RAS-GTPases. The three RAF kinase family members are: A-Raf, B-Raf and C-Raf (Raf-1).

Radiation therapy means exposing a subject, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including x-rays, gamma rays and neutrons.

RAL is RAS-related protein ral. Ral protein family, including RALA and RALB, belongs to the RAS family of small GTPases. Like other RAS GTPases, Ral proteins function as molecular switches alternating between inactive GDP-bound and active GT-bound states.

RAP is GTP-binding protein also known as RAS-related proteins or simply RAP is a type of small GTPase, similar in structure to RAS. These proteins share approximately 50% amino acid identity with the classical RAS proteins and have numerous structural features in common. The most striking difference between RAP proteins and RAS proteins resides in their 61st amino acid: glutamine in RAS is replaced by threonine in RAP proteins. RAP counteracts the mitogenic function of RAS because it can interact with RAS GAPs and RAF in a competitive manner.

RAS refers to a family of related proteins which are ubiquitously expressed in all cell lineages and organs. All RAS protein family members belong to a class of protein called small GTPase that are involved in transmitting signals within cells. RAS proteins are a type of G-protein found in the cytosol that are homologous to the alpha subunit of heterotrimeric G-proteins, but unlike the alpha subunit of G proteins, a small GTPase can function independently as a hydrolase enzyme to bind to and hydrolyze a guanosine triphosphate (GTP) to form guanosine diphosphate (GDP). RAS proteins of interest include, but are not limited to hRAS, kRAS and nRAS.

RBC is red blood cell. RBCs transport oxygen from the lungs to body tissues. Their production is stimulated by erythropoietin, secretion of which is controlled by blood oxygen tension. Erythropoietin stimulates maturation of RBC precursors in bone marrow into mature RBCs. Blood loss, parasitism, renal failure, RBC damage, chronic inflammatory disease, hematopoietic malignancies, and insufficient dietary iron, copper, or vitamin B12 cause a deficiency of RBCs. Shock, fluid loss, or increased RBC production can cause increased RBC numbers. Dehydration or protein fluid extravasation causes a relative decrease in the fluid portion of the blood and a relative increase in the cellular fraction. Carbon monoxide, lung disease, heart disease, and high altitude cause excessive RBC production by stimulating erythropoietin secretion. Erythrocytic malignancies and polycythemia vera cause excessive RBC production without normal stimulation.

RDWc is red cell distribution width count. The red cell distribution width is an electronic measure of anisocytosis (variation of cell size). RDW increases where the degree of anisocytosis is increased. In regenerative anemia, RDW increases when large cells are produced even before the MCV exceeds the reference range. It also increases when small cells are produced as with iron deficiency anemia.

REM1/REM2 is RAS (RAD and GEM)-like GTP-binding 1. The proteins are expressed in endothelial cells, where they promotes reorganization of the actin cytoskeleton and morphological changes in the cells.

RERG is RAS-related and estrogen-regulated growth inhibitor. RERG, a member of the RAS superfamily of GTPases, inhibits cell proliferation and tumor formation.

SALT THEREOF refers to a compound formed when the hydrogen of an acid is replaced by a cation, such as a metal cation or an organic cation and the like. In some cases, the salt is a pharmaceutically-acceptable salt, although this is not required for salts of intermediate compounds which are not intended for administration to a patient.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Signal transduction is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

SOS (Son of Sevenless) refers to guanine nucleotide exchange factor that act on RAS proteins and catalyzes the exchange of guanosine diphosphate (GDP) with guanosine triphosphate (GTP).

TBIL is total bilirubin, which is an orange-yellow pigment, a waste product primarily produced by the normal breakdown of heme. Heme is a component of hemoglobin, which is found in red blood cells (RBCs). Bilirubin is ultimately processed by the liver to allow its elimination from the body. Any condition that accelerates the breakdown of RBCs or affects the processing and elimination of bilirubin may cause an elevated blood level.

TREATING or TREATMENT as used herein refers to the treating or treatment of a disease or medical condition (such as a bacterial infection) in a patient, such as a mammal (particularly a human or a companion animal) which includes: ameliorating the disease or medical condition, i.e., eliminating or causing regression of the disease or medical condition in a patient; suppressing the disease or medical condition, i.e., slowing or arresting the development of the disease or medical condition in a patient; or alleviating the symptoms of the disease or medical condition in a patient.

Certain compounds of the present disclosure can exist in unsolvated forms as well as solvated forms, including hydrated forms. In general, both solvated forms and unsolvated forms are intended to be encompassed within the scope of the present disclosure. Certain compounds of the present disclosure may exist in multiple crystalline or amorphous forms (i.e., as polymorphs). In general, all physical forms are equivalent for the uses contemplated by the present disclosure and are intended to be within the scope of the present disclosure.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. Enantiomeric and stereoisomeric mixtures can be resolved into their component enantiomers or stereoisomers using separation techniques or chiral synthesis techniques well known to the skilled artisan. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

Certain compounds of the present disclosure possess asymmetric carbon atoms (optical centers) or double bonds; the racemates, diastereomers, geometric isomers and individual isomers (e.g., separate enantiomers) are all intended to be encompassed within the scope of the present disclosure. The compounds of the present disclosure may also contain unnatural proportions of atomic isotopes at one or more of the atoms that constitute such compounds. For example, the subject compounds may be radiolabeled with radioactive isotopes, such as for example tritium, iodine-$^{125}$I or $^{14}$C. Examples of isotopes that can be incorporated into the compounds disclosed herein include, but are not limited to, $^{2}$H, $^{3}$H, C, $^{11}$C, $^{14}$C, $^{15}$N, $^{18}$O, $^{17}$O, etc. All isotopic variations of the subject compounds, whether radioactive or not, are intended to be encompassed within the scope of the present disclosure.

Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

Furthermore, except as otherwise noted, the chemical methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

TP is total protein. A total serum protein test measures the total amount of protein in the blood. It also measures the amounts of two major groups of proteins in the blood: albumin and globulin.

$V_z$ is apparent volume of distribution during terminal phase, theoretical volume in which a drug is distributed.

WBC is white blood cell count. The total WBC count combines circulating numbers of neutrophils, lymphocytes, monocytes, eosinophils and basophils. Because neutrophils are the predominant leukocytic cell type, a high total WBC count (leukocytosis) is generally due to an increase in this cell type. However, absolute values of individual leukocytic cell types often provide more diagnostic specificity. Leukopenia (decreased WBCs) is generally evident only with a decrease in neutrophils. Leukocytosis and leukopenia occur with a variety of diseases.

As used herein and unless indicated otherwise, the term "linker" or "linkage" refers to a linking moiety that connects two groups and has a backbone of 100 atoms or less in length. A linker or linkage may be a covalent bond that connects two groups or a chain of between 1 and 100 atoms in length, for example a chain of 1, 2, 3, 4, 5, 6, 8, 10, 12, 14, 16, 18, 20 or more carbon atoms in length, where the linker may be linear, branched, cyclic or a single atom. In some cases, the linker is a branching linker that refers to a linking moiety that connects three or more groups. In certain cases, one, two, three, four or five or more carbon atoms of a linker backbone may be optionally substituted with a sulfur, nitrogen or oxygen heteroatom. The bonds between backbone atoms may be saturated or unsaturated, and in some cases not more than one, two, or three unsaturated bonds are present in a linker backbone. The linker may include one or more substituent groups, for example with an alkyl, aryl or alkenyl group. A linker may include, without limitations, polyethylene glycol; ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone.

When describing the compounds, compositions, methods and processes of this invention, the following terms have the meanings defined herein, unless otherwise indicated.

DETAILED DESCRIPTION

As summarized above, RAS modulating compounds and methods of using the same are provided. The compounds find use in modulating the activity of a target RAS in a sample. The target RAS can be a mutant RAS that is implicated in a condition or disease. In some cases, the subject compounds can inhibit the growth of cancer cells whose progression is driven by kRAS or a mutated kRAS. Methods of treating a subject for a RAS driven disease including administering a therapeutically effective amount of the subject compound are provided. Also provided are pharmaceutical compositions and kits which include the subject compounds.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Modulation of Ras

The present disclosure provides RAS modulating compounds and salts thereof, and solvate, hydrate and/or prodrug form thereof, and compositions including the same. Also provided are methods that find use in the modulation of the activity of a target RAS GTPase. As used herein, the terms "RAS" and "RAS GTPase" are used interchangeably to refer to members of the class of hydrolase enzymes called, also called "small GTPase", that are involved in transmitting signals within cells. RAS subfamily members of interest which may be targeted using the subject compounds include, but are not limited to, hRAS, kRAS and nRAS. In some cases, the target RAS is one that is implicated in a cancer of interest. Exemplary target RAS proteins of interest which may be targeted using the subject compounds include, but are not limited to, DIRAS1; DIRAS2; DIRAS3; ERAS; GEM; MRAS; NKIRAS1; NKIRAS2; nRAS; RALA; RALB; RAP1A; RAP IB; RAP2A; RAP2B; RAP2C; RASD1; RASD2; RASL10A; RASL10B; RASL11A; RASL11B; RASL12; REM1; REM2; RERG; RERGL; RRAD; RRAS; RRAS2.

The target RAS can be a RAS GTPase or a mutant RAS GTPase which is implicated in a disease condition (e.g., as described herein). In some cases, the target RAS is a mutant RAS GTPase, such as a hRAS, a nRAS or a kRAS mutant. The mutant RAS can include a mutation at a variety of positions, such as mutation at G12, G13 or Q61. In certain cases, the RAS is a RAS-G1 2V mutant. The present disclosure provides RAS modulating compounds that can have anti-cancer activity.

In further describing the various aspects of the invention, the function and structure of various embodiments of RAS modulating compounds are described first in greater detail, followed by a description of methods and applications in which the compounds finds use.

Compounds that Modulate RAS Activity

As summarized above, aspects of the present disclosure include RAS modulating compounds. The RAS modulating compounds are compounds which modulate the activity of a target RAS GTPase in a sample upon contact with a sample or components thereof. In some cases, by modulating the activity of a target RAS GTPase is meant that an activity related to the RAS in a cell is inhibited by 10% or more, such as 20% or more, 30% or more, 40% or more, 50% or more, 60% or more, 70% or more, 80% or more, 90% or more, or even more relative to a control, e.g., a cell not contacted with the compound of interest. Any convenient methods can be utilized in assessing modulation of the activity of RAS in a sample.

The sample can include a cell which includes the target RAS GTPase. In some embodiments, the RAS modulating compound decreases RAS-induced proliferation of cells that include the RAS GTPase. In some cases, the RAS-induced cellular proliferation is induced by a mutant RAS that can be targeted for inhibition using the subject compounds. By "decreases RAS-induced proliferation" is meant decreasing proliferation of the cells by 10% or more, such as 20% or more, 30% or more, 40% or more, 50% or more, 60% or more, 70% or more, 80% or more, 90% or more, or even more, relative to a control, e.g., cells not contacted with the compound of interest. In certain instances the RAS modulating compound is an inhibitor of kRAS, such as a specific inhibitor of a mutated kRAS variant. The subject compound can provide a significant anti-cancer effect in patients suffering a malignancy.

Structural Features

A RAS modulating compound can include a linear arrangement of at least four structural features including an optional first cyclic group (e.g., monovalent cyclic group) connected to a second cyclic group, connected to a linking group which is connected to a third cyclic group (e.g., monovalent cyclic group). In some cases, the first cyclic group is present and the second cyclic group is bivalent. The first, second and third cyclic groups can each independently be a heterocyclic group or a carbocyclic group and can be unsubstituted or substituted. In some cases, the first, second and third cyclic groups are each independently selected from an aryl, a cycloalkyl, a heterocycle and a heteroaryl, where the group can be monovalent or divalent and substituted or unsubstituted.

The linking group can be acyclic or can include a cyclic group. In some cases, the linking group is of between 1 and 20 atoms in length, such as of 1 to 10, or 2 to 6 atoms in length. The linking group may include a ring structure (e.g., a heterocycle group or a cycloalkyl group), and may include 1 or more heteroatoms, and/or may be optionally substituted. In certain instances, the linking group is selected from a carbon chain (e.g., a substituted or unsubstituted C1-C10 alkyl linker), a carbon chain including an ether, an amino or an amido functional group and a polyethyleneglycol (PEG) chain. In certain instances, the linking group includes a heterocycle group or a cycloalkyl group.

In some embodiments, the compound is of Formula 1:

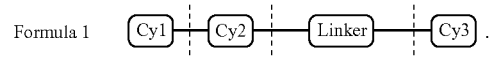

Formula 1 where Cy 1, Cy2, and Cy3 are each independently a cyclic group and Linker is a linking group. Any convenient aryl and heteroaryl groups can be used as the Cy1, Cy2 and C3 groups of Formula 1. Any convenient linking groups can be utilized as the Linker of Formula 1. It is understood that the subject compounds of Formula 1 could include a salt form or a stereoisomer, or a solvate, hydrate and/or prodrug form thereof, and that all such forms are meant to be encompassed by the present disclosure. In Formula 1, Cy1 and Cy2, Cy2 and Linker and Linker and Cy3 can be connected to each other via single covalent bonds. For example, Scheme 1 below illustrates two exemplary compounds (Structure 2 and 3) of Formula 1 where the connection and configuration of exemplary Cy1, Cy2, Linker and Cy3 groups is shown.

Scheme 1

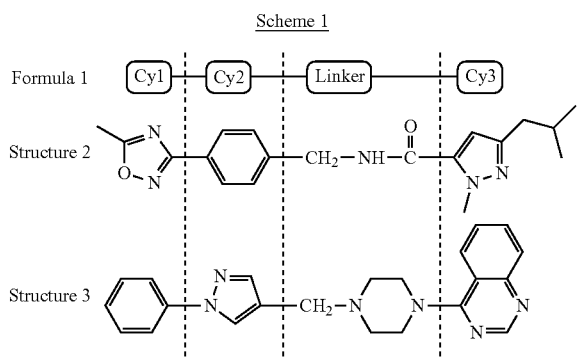

In some embodiments of Formula 1, Cy1, Cy2 and Cy3 are each independently selected from substituted cycloalkyl, unsubstituted cycloalkyl, substituted aryl, unsubstituted aryl, substituted heteroaryl, unsubstituted heteroaryl, substituted cycloheteroalkyl, unsubstituted cycloheteroalkyl, substituted bicycloalkenyl, unsubstituted bicycloalkenyl substituted bicycloheteroalkenyl, unsubstituted bicycloheteroalkenyl, substituted bicycloaryl, unsubstituted bicycloaryl, substituted bicycloheteroaryl and substituted bicycloheteroaryl.

A variety of substituents of interest can be included on one or more of the Cy1, Cy2 and Cy3 groups of the subject compounds (e.g., a compound of Formula 1 or any of the structural formulae described herein), eg, from 1 to 5 substituents (e.g., the X groups or X substituents described in any one of the Formula described herein) independently selected from halogen, —CN, —NO$_2$, —OH, —OR$_1$, —C(O)R$_1$, —CO$_2$R1, —O(CO)R$_1$, —C(O)NR$_1$R2, —OC(O)NR$_1$R2, —SR$_1$, —SOR$_1$, —SO$_2$R1, —SO$_2$NR$_1$R2, —NR$_1$R2, —NR$_1$C(O)R$_2$, —NR$_1$C(O)$_2$R2, —NR$_1$SO$_2$R2, —NR$_1$(CO)NR$_2$R3, unsubstituted or substituted C$_{1-8}$ alkyl, unsubstituted or substituted C$_{2-8}$ alkenyl, unsubstituted or substituted C$_{2-8}$ alkynyl, unsubstituted or substituted C$_{3-8}$ cycloalkyl, unsubstituted or substituted C$_{6-10}$ aryl, unsubstituted or substituted 5- to 10-membered heteroaryl, and unsubstituted or substituted 3- to 10-membered heterocyclyl; where R$_1$, R$_2$ and R$_3$ are each independently selected from hydrogen, unsubstituted or substituted C$_{1-6}$ haloalkyl, unsubstituted or substituted C$_{1-6}$ alkyl, unsubstituted or substituted C$_{3-6}$ cycloalkyl, unsubstituted or substituted C$_{2-6}$ alkenyl, unsubstituted or substituted C$_{2-6}$ alkynyl, unsubstituted or substituted C$_{6-10}$ aryl, unsubstituted or substituted 5- to 10-membered heteroaryl, unsubstituted or substituted aryl-C$_{1-4}$ alkyl, unsubstituted or substituted aryl-C$_{1-4}$ alkyl, and unsubstituted or substituted aryloxy-C$_{1-4}$ alkyl; or two of R$_1$, R$_2$ together or R$_1$ and R$_3$ together with the atom(s) to which they are attached, may form an unsubstituted or substituted 5-, 6- or 7-membered ring.

In some instances of Formula 1, the compound has the Formula 1a:

wherein:
Cy$_1$ is an optional cyclic group selected from an oxadiazole or a thiadiazole;
Cy$_2$ is a phenyl;
Cy$_3$ is a pyrazole, wherein Cy$_1$, Cy$_2$ and Cy$_3$ are optionally further substituted;
n and m are each independently 0, 1, 2, 3, 4, 5 or 6, wherein n+m is less than 7;

each R$^1$ and each R$^2$ is independently H, an alkyl or a substituted alkyl; and
Y$^1$ is selected from —CONR—, —NRCO—, —NRSO$_2$—and —SO$_2$NR—wherein R is H, an alkyl or a substituted alkyl.

In some embodiments of Formula 1a, the Cy1 group is an oxadiazole or a thiadiazole (e.g., a 1,2,4-oxa or thia-diazole) which is connected to Cy2 via the 3-position and is optionally further substituted. In certain embodiments of Formula 1 a, the Cy2 group is a phenyl which is connected to Cy1 and Linker via any convenient positions of the ring. In some cases, the Cy2 is a 1,4-linked phenyl which is optionally further substituted. In some cases, the Cy2 is a 1,3-linked phenyl which is optionally further substituted. In certain embodiments of Formula 1a, the Cy3 group is a pyrazole which is connected to Linker via the 5-position. The pyrazole ring can be further substituted, e.g., as the 1, 3 and/or 4 positions. In certain embodiments of Formula 1a, the Cy3 group is a pyrazole which is connected to Linker via the 3-position. The pyrazole ring can be further substituted, e.g., as the 1, 4 and/or 5 positions. In some embodiments of Formula 1 a, the Linker group is —(CH$_2$)$_n$NRCO— or —CONR(CH$_2$)$_n$— where n is 0, 1, 2, 3, 4 or 5 (e.g., n is 1) and R is H or an alkyl (e.g., methyl). In certain instances of Formula 1 a, n is 0. In certain instances of Formula 1a, m is 0. In certain instances of Formula 1a, Y is —CONR—or —NRCO—where R is H.

In some instances of Formula 1, the compound has the Formula 1b:

wherein:
Cy$_1$ is selected from phenyl and a 4, 5 or 6-membered heterocycle (e.g., heteroaryl) comprising one or more heteroatoms in the ring independently selected from O, N and S and at least one carbon atom;
Cy$_2$ is selected from a pyrazole, a pyrrole, a 1,2,3-triazole and an imidazole;
Cy$_3$ is a pyridinyl, a pyrimidinyl, a triazinyl, a quinazolinyl, a pyrido-pyrimidinyl, a pyrido-pyridazinyl, a pyrrolo-pyrimidinyl, a pyrazolo-pyrimidinyl or a purine (e.g., a heterocyclic group of Table 6, described herein), wherein Cy$_1$, Cy$_2$ and Cy$_3$ are optionally further substituted;
n is 0, 1, 2, 3, 4, 5 or 6, and m is 0 or 1;
each R$^1$, each R$^2$ and R is independently H, an alkyl or a substituted alkyl; and
Y$^2$ is a cycloalkyl, a monocyclic heterocycle or a bicyclic heterocycle.

In some embodiments of Formula 1b, the Cy1 group is a phenyl which is connected to Cy2 and is optionally further substituted. In some embodiments of Formula 1b, the Cy1 group is a 6-membered heteroaryl which is connected to Cy2 and is optionally further substituted. In some embodiments of Formula 1b, the Cy1 group is a 6-membered heteroaryl selected from a 2-pyridyl, a 3-pyridyl, a 4-pyridyl, a 3-pyridazinyl, a 4-pyridazinyl, a 4-1,2,3-triazinyl, a 4-pyrimidinyl, where the Cy1 is optionally further substituted. In some embodiments of Formula 1b, the Cy1 group is selected from a 2-pyridyl, a 3-pyridyl, a 4-pyridyl, where the Cy1 is optionally further substituted. In certain embodiments of Formula 1b, the Cy2 group is a pyrazole or a pyrrole which is connected to Cy1 and Linker via any convenient positions of the ring. In some cases, the Cy2 is a 1,4-linked pyrazole which is optionally further substituted. In some cases, the Cy2 is a 1,3-linked pyrazole which is optionally further substituted. In some cases, the Cy2 is a 1,3-linked 1 H-pyrrole which is optionally further substituted. In some cases, the Cy2 is a 1,4-linked 1-H-1,2,3-triazole which is optionally further substituted. In some cases, the Cy2 is a 1,4-linked 1 H-imidazole which is optionally further substituted. In some cases, the Cy2 is a 2,5-linked furan or thiophene which is optionally further substituted. In certain embodiments of Formula 1b, the Cy3 group is a pyrimidinyl. In certain embodiments of Formula 1b, the Cy3 group is a 2-pyrimidinyl or a 4-pyrimidinyl, where the pyrimidinyl is optionally further substituted. In certain embodiments of Formula 1b, the Cy3 group is a quinazolinyl. The quinazoline ring can be connected to Linker via the 4-position. The quinazoline ring can be connected to Linker via the 2-position. The Cy3 ring can be further substituted at any convenient positions. In some embodiments of Formula 1 b, the Linker group is —(CH$_2$),Het- where n is 0, 1, 2, 3, 4 or 5 (e.g., n is 0 or 1) and Het is a heterocycle. In some instances, Het is a saturated heterocycle, such as a monocyclic or bicyclic heterocycle. In certain cases, Het is a piperazine or a piperidine ring that is linked to the adjacent moieties via the N atom(s) of the heterocycle. In certain cases, Het is a octahydropyrrolo[3,4-c]pyrrole ring that is linked to the adjacent moieties via the N atom(s) of the bicyclic heterocycle. In some embodiments of Formula 1b, the Linker group is —(CH$_2$),Het-NR— where n is 0, 1, 2, 3, 4 or 5 (e.g., n is 0 or 1), Het is a heterocycle and R is H or an alkyl (e.g., a methyl). In certain instances, n is 1, Het is a 1,3-pyrrolidinyl and R is H, e.g., the Linker is —CH$_2$-(1,3-pyrrolidinyl)-NH—. In some embodiments of Formula 1 b, the Linker group is —(CH$_2$)$_n$(cycloalkyl)NR— (e.g., where n is 0, 1, 2, 3, 4 or 5 (e.g., n is 1), cycloalkyl is cyclobutyl, cyclopropyl and R is H). In some embodiments of Formula 1 b, the Linker group is —(CR$^1$R2)$_n$-Y$^2$— where Y$^2$ is a 1,4-dihydropyrazine, wherein Y$^2$ is optionally further substituted. In certain instances, n is 1 and Y$^2$ is linked via the 1,4-positions (e.g., as depicted in Formula 0).

In some embodiments of Formula 1, the Linker group is selected from (CH$_2$)$_2$—, —(CH$_2$)$_3$—, —(CH$_2$)$_4$—, —(CH$_2$)$_5$—, —OCH$_2$—, —O(CH$_2$)$_2$—, —O(CH$_2$)$_3$—, —O(CH$_2$)$_4$—, —O(CH$_2$)$_5$—, —SCH$_2$—, —S(CH$_2$)$_2$—, —S(CH$_2$)$_3$—, —S(CH$_2$)$_4$—, —S(CH$_2$)$_5$—, —SOCH$_2$—, —SO(CH$_2$)$_2$—, —SO(CH$_2$)$_3$—, —SO(CH$_2$)$_4$—, —SO(CH$_2$)$_5$—, —N(R)CH$_2$—, —SO$_2$CH$_2$—, —SO$_2$(CH$_2$)$_2$—, —SO$_2$(CH$_2$)$_3$—, —SO$_2$(CH$_2$)$_4$—, —SO$_2$(CH$_2$)$_5$—, —N(R)(CH$_2$)$_2$—, —N(R)(CH$_2$)$_3$—, —N(R)(CH$_2$)$_4$—, —N(R)(CH$_2$)$_5$—, —CH$_2$—O—CH$_2$—, —CH$_2$—O—(CH$_2$)$_2$—, —CH$_2$—O—(CH$_2$)$_3$—, —(CH$_2$)$_2$-O—CH$_2$—, —(CH$_2$)$_2$-O—(CH$_2$)$_2$—, —(CH$_2$)$_3$O—CH$_2$—, —(CH$_2$)$_3$-O—(CH$_2$)$_2$—, —CH$_2$—S—CH$_2$—, —CH$_2$—S—(CH$_2$)$_2$—, —CH$_2$—S—(CH$_2$)$_3$—, —(CH$_2$)$_2$-S—CH$_2$—, —(CH$_2$)$_2$-S—(CH$_2$)$_2$—, —(CH$_2$)$_3$—S—CH$_2$—, —(CH$_2$)$_3$—S—(CH$_2$)$_2$—, —CH$_2$—SO—CH$_2$—, —CH$_2$—SO—(CH$_2$)$_2$—, —CH$_2$—SO—(CH$_2$)$_3$—, —(CH$_2$)$_2$-SO—CH$_2$—, —(CH$_2$)$_2$-SO—(CH$_2$)$_2$—, —(CH$_2$)$_3$-SO—CH$_2$—, —(CH$_2$)$_3$-SO—(CH$_2$)$_2$—, —CH$_2$—SO$_2$—CH$_2$—, —CH$_2$—SO$_2$—(CH$_2$)$_2$—, —CH$_2$—SO$_2$—(CH$_2$)$_3$—, —(CH$_2$)$_2$-SO$_2$—CH$_2$—, —(CH$_2$)$_2$-SO$_2$—(CH$_2$)$_2$—, —(CH$_2$)$_3$-SO$_2$—CH$_2$—, —(CH$_2$)$_3$-SO$_2$—(CH$_2$)$_2$—, —CH$_2$—N(R)—CH$_2$—, —CH$_2$—N(R)—(CH$_2$)$_2$—, —CH$_2$—N(R)—(CH$_2$)$_3$—, —(CH$_2$)$_2$-N(R)—CH$_2$—, —(CH$_2$)$_2$-N(R)—(CH$_2$)$_2$—, —(CH$_2$)$_3$-N(R)—CH$_2$—, and —(CH$_2$)$_3$-N(R)—(CH$_2$)$_2$—, where R is H, an alkyl or a substituted alkyl (e.g., methyl). In some embodiments of Formula 1, the linker group comprises a 3-6 membered cyclic structure selected from unsubstituted or substituted benzene, cyclobutane, cyclopentane, cyclohexane, cyclopropane, pyrrole, piperazine, piperidine, pyridine, pyrimidine, imidazole, furan, pyran, thiophene, thiazole, pyrazine, oxazole, isoxazole, triazole, tetrazole,1,2,4-triazole, 1,2,3 triazole, 1,4-dihydropyrazine and isothiazole, where the 3-6 membered cyclic structure can be attached to an additional linear linker that together make up the "Linker", or can be directly connected to both the Cy2 and Cy3 groups.

In some embodiments of Formula 1, Cy1 and Cy2 are selected from monocyclic or bicyclic unsubstituted or substituted aryl, monocyclic or bicyclic unsubstituted or substituted C$_{5-10}$ heteroaryl, unsubstituted or substituted monocyclic or bicyclic C$_{3-10}$ heterocyclyl, and NR$_4$R$_5$ where R$_4$ and R$_5$ together with the nitrogen atom to which they are attached form unsubstituted or substituted monocyclic or bicyclic C3-10 heterocyclyls.

In some embodiments of Formula 1, the compound has the structure of one of Formulae 4 and 5:

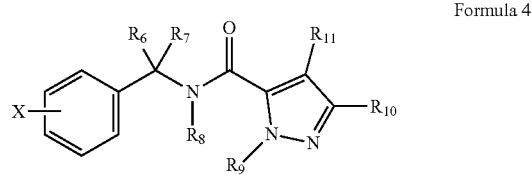

Formula 4

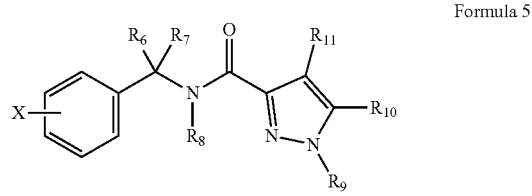

Formula 5 where:
  X is one or more substituents;
  each X, R$^{10}$ and R" are each independently selected from hydrogen, halogen, —CN, —NO$_2$, —OH, —OR$_a$, —C(O)R$_a$, —CO$_2$Ra, —O(CO)R$_a$, —C(O)NR$_a$Rb, —OC(O)NR$_a$Rb, —SR$_a$, —SOR$_a$, —SO$_2$R$_a$, —SO$_2$NR$_a$R$_b$, —NR$_a$R$_b$, —NR$_a$C(O)R$_b$, —NR$_a$C(O)$_2$R$_b$, —NR$_a$SO$_2$R$_b$, —NR$_a$(CO)NR$_b$R$_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein R$_a$, R$_b$ and R, are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of R$_a$, R$_b$ together or R$_a$ and R$_c$ together with the atom(s) to which they are attached, may form an unsubstituted or substituted 5-, 6- or 7-membered ring;
  R$_6$, R$_7$, R$_8$ and R$_9$ are each independently hydrogen, an alkyl or a substituted alkyl (e.g., an alkyl of Table 1);
  or a salt thereof.

In some embodiments, the compound has the structure of one of Formulae 6 and 7:

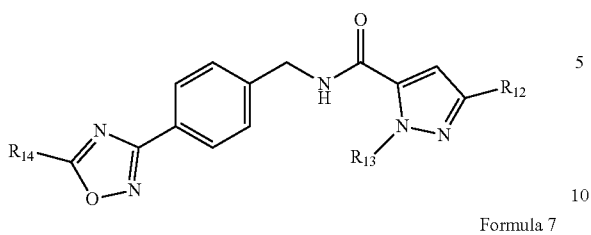

Formula 6

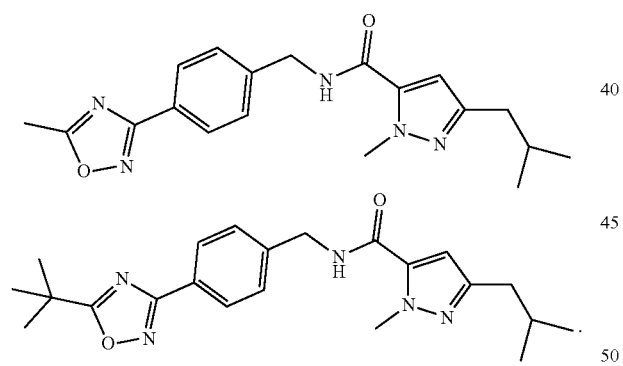

Formula 7 where:
R$_{13}$ and R$_{16}$ are selected from hydrogen, an alkyl and a substituted alkyl (e.g., an alkyls listed in Table 1); and
R$_{12}$, R$_{14}$, R$_{15}$ and R$_{17}$ are each independently hydrogen or a substituent as defined for group X of Formulae 4 and 5. In certain embodiments of Formula 6 and 7, R$_{12}$, R$_{14}$, R$_{15}$ and R$_{17}$ are independently selected from hydrogen, an alkyl and a substituted alkyl (e.g., an alkyl listed in Table 1). In certain embodiments of Formula 6 and 7, R$_{13}$ and R$_{16}$ are independently selected from hydrogen and an alkyls listed in Table 1. In certain embodiments of Formula 6 and 7, R$_{12}$ is isobutyl, R$_{13}$ is methyl and R$_{14}$ is hydrogen (e.g., Structure 2). In some cases, the compound has one of the following structures:

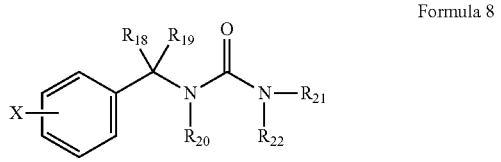

In some embodiments, the compound has the structure of Formula 8:

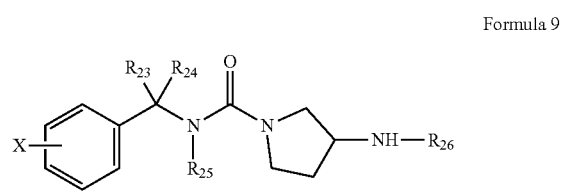

Formula 8 where:
R$_{21}$ and R$_{22}$ together with the nitrogen atom to which they are attached can form substituted or unsubstituted saturated or unsaturated C3-C9 heterocycle;

R$_{18}$, R$_{19}$ and R$_{20}$ are each independently hydrogen, an alkyl or a substituted alkyl (e.g., an alkyl listed in Table 1); and X is hydrogen or as described for Formula 4;

or a salt thereof. In some embodiments of Formula 8, the substituted or unsubstituted saturated or unsaturated C3-C9 heterocycle is a 5, 6 or 7-membered heterocycle which is optionally substituted, such as a pyrrolidine, a piperidine, a morpholine, a piperazine or the like.

In certain embodiments of Formula 8, the compound has the structure of Formula 9:

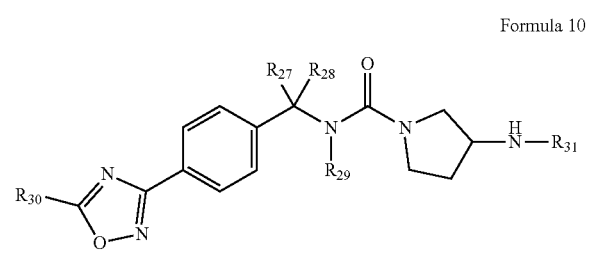

Formula 9 where:
R$_{23}$, R$_{24}$, and R$_{25}$ are independently hydrogen, alkyl or substituted alkyl (e.g., an alkyl listed in Table 1);

X is H or a substituent as described for Formula 4;

R$_{26}$ is hydrogen, an alkyl, a substituted alkyl, an acyl or a substituted acyl (e.g., acetyl, propionyl or butyryl);

or a salt thereof. In certain instances of Formula 9, R$_{26}$ is H. In certain instances of Formula 9, R$_{26}$ is an acyl or a substituted acyl. In certain instances of Formula 9, R$_{26}$ is acetyl, propionyl or butyryl. In certain instances of Formula 9, R$_{25}$ is H.

In certain embodiments of Formula 9, the compound has the structure of Formula 10:

Formula 10 where R$_{27}$, R$_{28}$, and R$_{29}$ are each independently hydrogen, an alkyl or a substituted alkyl;

R$_{30}$ is H or a substituent as described for group X of Formula 4; and

R$_{31}$ is hydrogen, an alkyl, a substituted alkyl, an acyl or a substituted acyl (e.g., acetyl, propionyl or butyryl);

or a salt thereof. In certain instances of Formula 10, R$_{31}$ is H. In certain instances of Formula 10, R$_{31}$ is an acyl or a substituted acyl. In certain instances of Formula 10, R$_{31}$ is acetyl, propionyl or butyryl. In certain instances of Formula 10, R$_{29}$ is H.

In some instances of Formula 1 or 1 b, the compound has a structure of one of Formulae 11-26. In these Formulae, X designates one or more substituents as described above for Formula 4. In certain embodiments, the compound is of Formula 11:

Formula 11

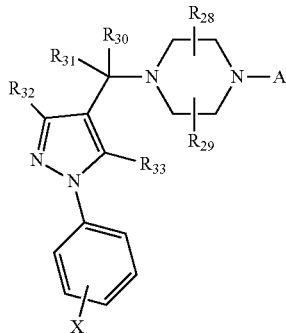

where:
$R_{28}$, $R_{29}$, $R_{30}$ and $R_{31}$ are each independently hydrogen, an alkyl or a substituted alkyl (e.g., an alkyl of Table 1);
$R_{32}$ and $R_{33}$ are each independently hydrogen or an X substituent as described for Formula 4; and
A is selected from the substituent groups listed in Table 6; or a salt thereof.

TABLE 6

Possible A groups at nitrogen of the pyrazine in Formula 11.

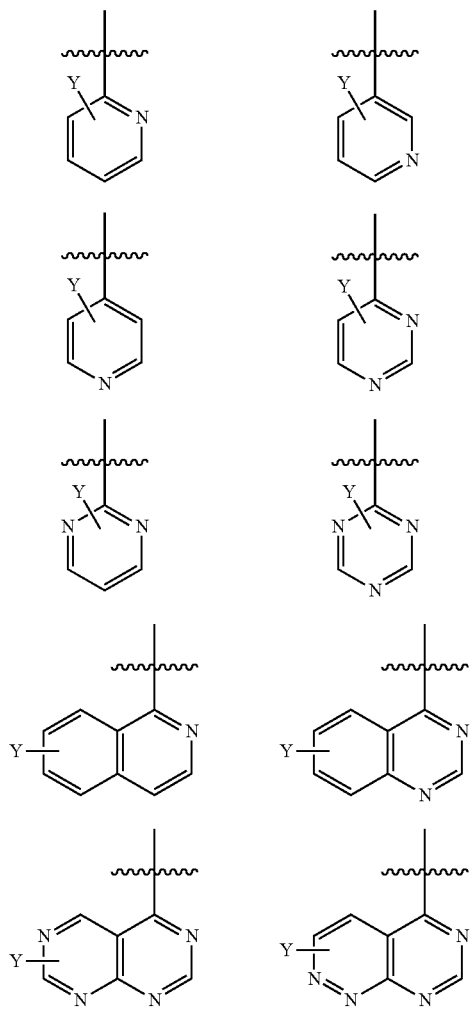

TABLE 6-continued

Possible A groups at nitrogen of the pyrazine in Formula 11.

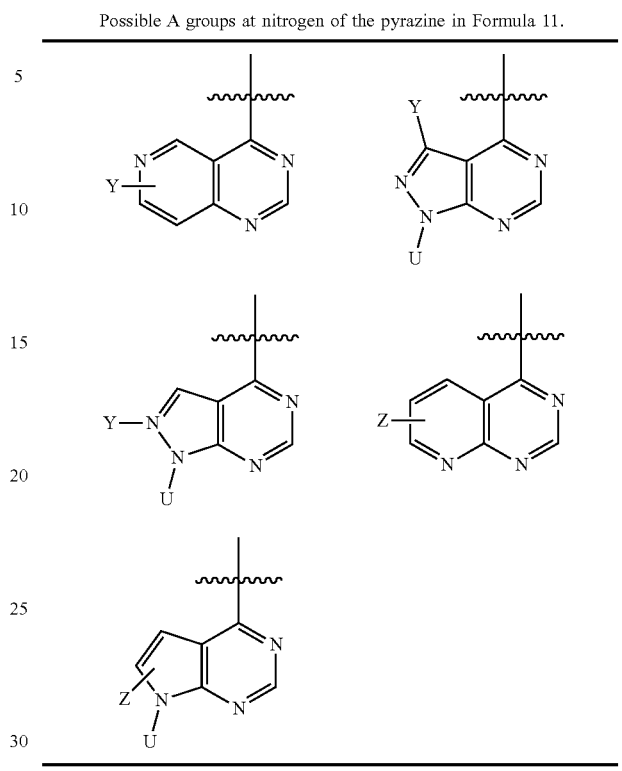

In Table 6, Y represents 0 to 6 substituents independently selected from hydrogen, halogen, —ON, —NO$_2$, —OH, —OR$_1$, —C(O)R$_{34}$, —CO$_2$R$_{35}$, —O(CO)R$_{36}$, —C(O)NR$_{37}$R$_{38}$, —OC(O)NR$_{39}$R$_{40}$, —SR$_{41}$, —SOR$_{42}$, —SO$_2$R$_{43}$, —SO$_2$NR$_{44}$R$_{45}$, —NR$_{46}$R$_{47}$, —NR$_{48}$C(O) R$_{49}$, —NR$_{50}$C(O)$_2$R$_{51}$, —NR$_{52}$SO$_2$R$_{53}$, —NR$_{54}$(CO)NR$_{55}$R$_{56}$, unsubstituted or substituted C$_{1-8}$-alkyl, unsubstituted or substituted C$_{2-8}$ alkenyl, unsubstituted or substituted C$_{2-8}$ alkynyl, unsubstituted or substituted C$_{3-6}$cycloalkyl, unsubstituted or aryl, unsubstituted or substituted 5- or 6-membered heteroaryl, and unsubstituted or substituted 3- to 6-membered heterocyclyl; where R$_{34}$—R$_{56}$ are each independently hydrogen, an alkyl or a substituted alkyl (e.g., an alkyl of Table 1);

U substituents are each independently selected from hydrogen, substituted or unsubstituted C$_{1-6}$ amino, unsubstituted or substituted C$_{1-6}$ haloalkyl, unsubstituted or substituted C$_{1-6}$ alkyl, unsubstituted or substituted C$_{3-6}$ cycloalkyl, unsubstituted or substituted C$_{2-6}$ alkenyl, unsubstituted or substituted C$_{2-6}$alkynyl; and Z represents 0 to 4 substituents independently selected from hydrogen, halogen, —ON, —NO$_2$, —OH, —OR$_{37}$, —(O)R$_{57}$, —C$_2$R58, —O(C)R$_{59}$, —C(O)NR$_{60}$R$_{61}$, —O(O)NR$_{62}$R$_{63}$, —SR$_{64}$, —SOR$_{65}$, —SO$_2$R$_{66}$, —SO$_2$NR$_{67}$R$_{68}$, —NR$_{69}$R$_{70}$, —NR$_{71}$C(O)R$_{72}$, —NR$_{73}$C(O)$_2$R$_{74}$, —NR$_{75}$SO$_2$R$_{76}$, —NR$_{77}$(CO)NR$_{78}$R$_{79}$, unsubstituted or substituted C$_{1-8}$ alkyl, unsubstituted or substituted C$_{2-8}$ alkenyl, unsubstituted or substituted C$_{2-8}$ alkynyl, unsubstituted or substituted C$_{3-6}$ cycloalkyl, unsubstituted or aryl, unsubstituted or substituted 5- or 6-membered heteroaryl, and unsubstituted or substituted 3- to 6-membered heterocyclyl; where R$_{37}$—R$_{79}$ are each independently Hydrogen, an alkyl or a substituted alkyl (e.g., an alkyl of Table 1).

In certain embodiments of Formula 11, the compound has a structure of Formula 12:

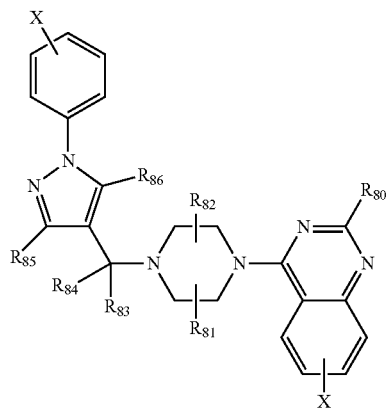

Formula 12 where:
- $R_{81}$, $R_{82}$, $R_{83}$, $R_{84}$, are each independently hydrogen, an alkyl or a substituted alkyl (e.g., an alkyl group listed in Table 1);
- $R_{80}$, $R_{85}$ and $R_{86}$ are independently selected from hydrogen and an X substituent as described for Formula 4;

or a salt thereof. In certain instances of Formula 12, X is H. In certain instances of Formula 12, $R_{80}$ is H. In certain instances of Formula 12, $R_{81-82}$ are each H. In certain instances of Formula 12, $R_{83-84}$ are each H. In certain instances of Formula 12, $R_{85}$ is H. In certain instances of Formula 12, $R_{86}$ is H. In certain instances of Formula 12, X, $R_{80}$, $R_{81}$, $R_{82}$, $R_{83}$, $R_{84}$, $R_{85}$, and $R_{86}$ are each hydrogen (e.g., Structure 3). In some instances, the compound has the following structure:

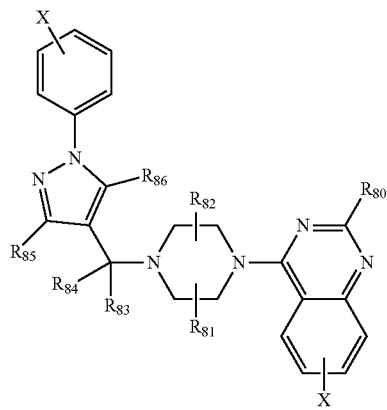

Formula 12 or a salt thereof.

In certain embodiments of Formula 1 b, the compound has a structure of one of the formula of Table 7.

TABLE 7

Exemplary compounds of Formula 1b

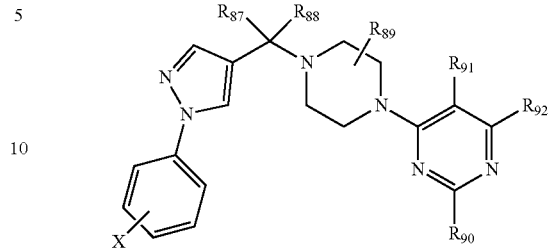

Formula 13

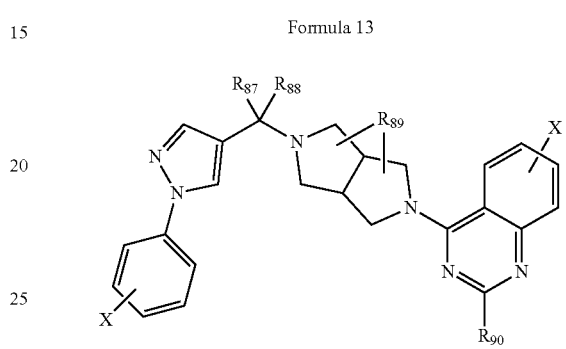

Formula 14

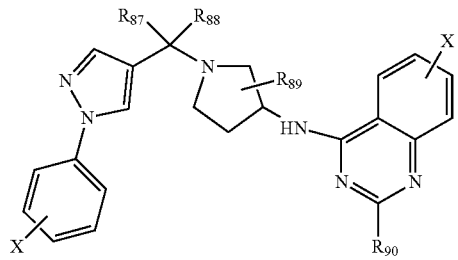

Formula 15

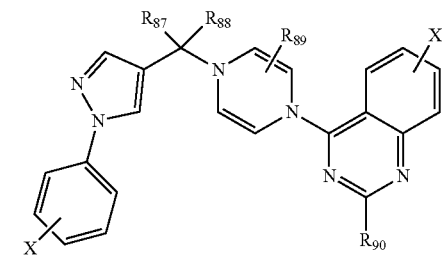

Formula 16

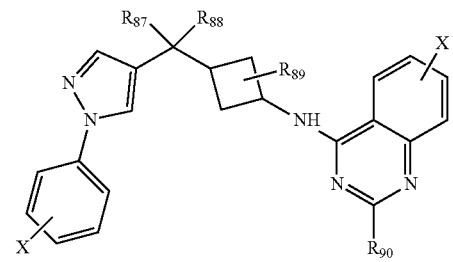

Formula 17

TABLE 7-continued
Exemplary compounds of Formula 1b
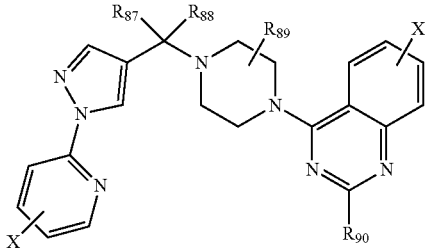
Formula 18
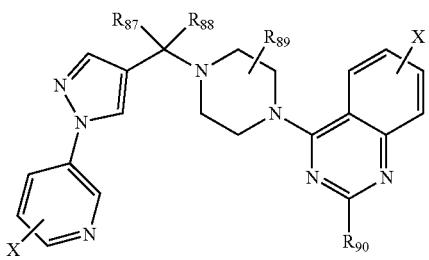
Formula 19
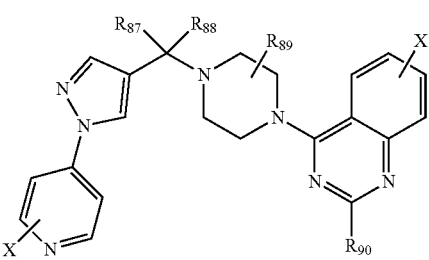
Formula 20
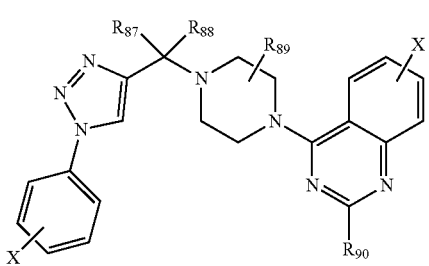
Formula 21
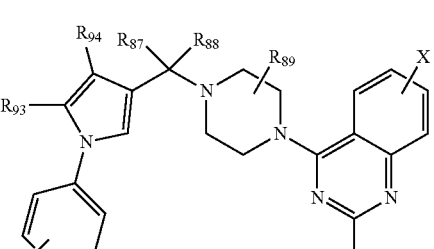
Formula 22
TABLE 7-continued
Exemplary compounds of Formula 1b
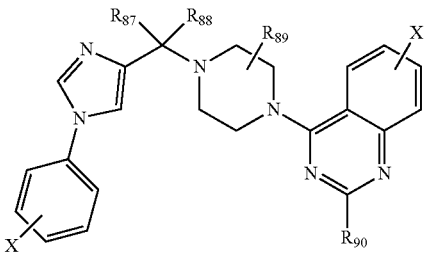
Formula 23
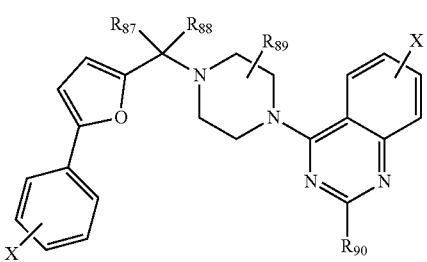
Formula 24
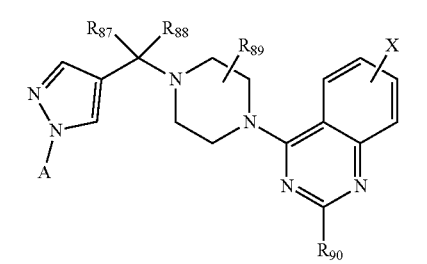
Formula 25
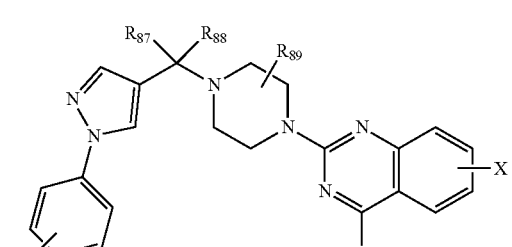
Formula 26
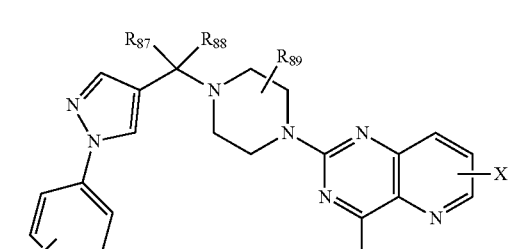
Formula 27

TABLE 7-continued

Exemplary compounds of Formula 1b

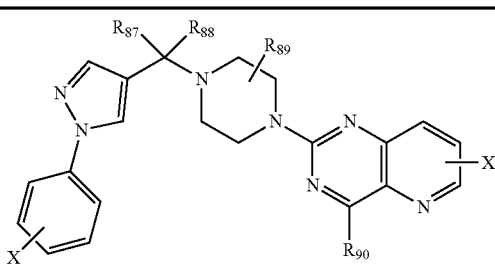

Formula 28

Formula 29

Formula 30

In Table 7, $R_{87}$, $R_{88}$, $R_{89}$ and $R_{90}$ are independently selected from hydrogen, an alkyl and a substituted alkyl (e.g., an alkyl of Table 1); $R_{92}$-$R_{94}$ are independently hydrogen or an X substituent as described for Formula 4; and A is one of the heterocyclic structures listed in Table 6.

Aspects of the present disclosure include RAS modulating compounds, salts thereof (e.g., pharmaceutically acceptable salts), and/or solvate, hydrate and/or prodrug forms thereof. In addition, it is understood that, in any compound described herein having one or more chiral centers, if an absolute stereochemistry is not expressly indicated, then each center may independently be of R-configuration or S-configuration or a mixture thereof. It will be appreciated that all permutations of salts, solvates, hydrates, prodrugs and stereoisomers are meant to be encompassed by the present disclosure.

In some embodiments, the subject compounds, or a prodrug form thereof, are provided in the form of pharmaceutically acceptable salts. Compounds containing an amine or nitrogen containing heteraryl group may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

In some embodiments, the subject compounds are provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)).

In some embodiments, the subject compounds, prodrugs, stereoisomers or salts thereof are provided in the form of a solvate (e.g., a hydrate). The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

Pharmaceutical Preparations

Also provided are pharmaceutical preparations. Pharmaceutical preparations are compositions that include a RAS modulating compound (for example one or more of the subject compounds, either alone or in the presence of one or more additional active agents) present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the present disclosure is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used.

When administered to a mammal, the compounds and compositions of the present disclosure and pharmaceutically acceptable vehicles, excipients, or diluents may be sterile. In some instances, an aqueous medium is employed as a vehicle when the subject compound is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference. The choice of excipient will be determined in part by the particular compound, as well as by the particular method used to administer the composition. Accordingly, there is a wide variety of suitable formulations of the subject pharmaceutical compositions.

Administration of the subject compounds may be systemic or local. In certain embodiments administration to a mammal will result in systemic release of a compound of the present disclosure (for example, into the bloodstream). Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the compounds and compositions of the present disclosure are administered subcutaneously. In certain embodiments, the compounds and compositions of the present disclosure are administered orally. In certain embodiments, it may be desirable to administer one or more compounds of the present disclosure locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject compound may also be formulated for oral administration. For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers. In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

The subject formulations can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (e.g., sunblocking agents), etc.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host. In pharmaceutical dosage forms, the compounds may be administered in the form of a free base, their pharmaceutically acceptable salts, or they may also be used alone or in appropriate association, as well as in combination, with other pharmaceutically active compounds.

Dose levels can vary as a function of the specific compound, the nature of the delivery vehicle, and the like. Desired dosages for a given compound are readily determinable by a variety of means. The dose administered to an animal, particularly a human, in the context of the present disclosure should be sufficient to effect a prophylactic or therapeutic response in the animal over a reasonable time frame, e.g., as described in greater detail herein. Dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound.

Methods of Inhibiting Mutant RAS

The RAS modulating compounds of the present disclosure find use in modulating the activity of a target RAS in a sample. The target RAS can be a mutant RAS. Aspects of the subject methods include contacting the sample with an effective amount of a RAS modulating compound (e.g., as described herein). In some cases, an effective amount of a RAS modulating compound is an amount sufficient to inhibit the activity of the target RAS in a sample by 10% or more, such as 20% or more, 30% or more, 40% or more, 50% or more, 60% or more, 70% or more, 80% or more, 90% or more, or even more relative to a control, e.g., a sample not contacted with the compound of interest.

As used herein, the term "sample" relates to a material or mixture of materials, in some cases in liquid form, containing one or more analytes of interest. In some embodiments, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents. The term "sample" may also refer to a "biological sample". As used herein, the term "a biological sample" refers to a whole organism or a subset of its tissues, cells or component parts (e.g. body fluids, including, but not limited to, blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, plasma, serum, spinal fluid, lymph fluid, the external sections of the skin, respiratory, intestinal, and genitourinary tracts, tears, saliva, milk, blood cells, tumors and organs. In certain embodiments, the sample has been removed from an animal or plant. Biological samples may include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

In some cases, the target RAS is a mutant kRAS, a mutant nRAS or a mutant hRAS. The mutant RAS may be one that is responsible for a RAS-induced promotion of cell growth or proliferation in the sample. The sample can be in vitro or in vivo. In some instances, the subject methods result in inhibition or decrease of RAS-induced proliferation by 10% or more, such as 20% or more, 30% or more, 40% or more, 50% or more, 60% or more, 70% or more, 80% or more, 90% or more, or even more, relative to a control, e.g., cells not contacted with the compound of interest.

Aspects of the subject methods include evaluating the activity of the target RAS in the sample. As used herein, the terms "evaluating", "determining," "measuring," and "assessing," and "assaying" are used interchangeably and include both quantitative and qualitative determinations. Evaluating the activity of the target RAS can be performed before and/or after the sample is contacted with the subject compound and can be achieved using any convenient methods, including both direct methods and indirect methods. Exemplary methods for evaluating the activity of the target RAS are described herein, for example, the cytotoxicity assay, the phosphorylated ERK bioassay, the cell morphology assay and the Fly assay of the Examples section.

Methods of Treatment

The RAS modulating compounds of the present disclosure find use in treatment of a condition or disease in a subject in which the activity of a mutant RAS GTPase is implicated (e.g., as described herein). Aspects of the method include administering to a subject in need thereof a therapeutically effective amount of a RAS modulating compound to treat the subject. By "a therapeutically effective amount" is meant the concentration of a compound that is sufficient to elicit the desired biological effect (e.g., treatment of the condition or disease). By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms. In the context of cancer, the term "treating" includes any or all of: reducing growth of a solid tumor, inhibiting replication of cancer cells, reducing overall tumor burden, and ameliorating one or more symptoms associated with a cancer.

The subject to be treated can be one that is in need of therapy, where the host to be treated is one amenable to treatment using the RAS modulating compound. In some embodiments, the subject is one that has kRAS-driven cancer. In certain embodiments, the subject has a tumor with cells containing a kRAS G1 2V mutation. In some embodiments, the subject is one that has a hRAS-driven tumor. In some embodiments, the subject is one that has a nRAS-driven tumor. In another aspect, the subject is a child with one of many genetic conditions termed RASopathies, as described by Niemeyer CM (RAS diseases in children. Haematologica. 2014; 99:1653-62).

In some cases, the subject methods of treatment include a step of determining or diagnosing whether the subject has a disease associated with a mutant RAS GTPase. The determining step can be performed using any convenient methods. In some cases, the determining step includes obtaining a biological sample from the subject and assaying the sample for the presence of a mutant RAS. The sample can be a cellular sample. In some cases, the sample is a biopsy (e.g., a tumor biopsy). The determining step can include identification of cancer cells including a kRAS mutation. The determining step can include identification of cancer cells including a hRAS mutation. The determining step can include identification of cancer cells including a nRAS mutation. In certain cases, the subject has a MYH associated polyposis, and the determining step includes identifying cells that include a mutant hRAS or nRAS.

Accordingly, a variety of subjects may be amenable to treatment using the RAS modulating compounds and pharmaceutical compositions disclosed herein. As used herein, the terms "subject" and "host" are used interchangeably. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of RAS modulating compound administered can be determined using any convenient methods to be an amount sufficient to produce the desired effect in association with a pharmaceutically acceptable diluent, carrier or vehicle. The specifications for the unit dosage forms of the present disclosure will depend on the particular compound employed and the effect to be achieved, and the pharmacodynamics associated with each compound in the host.

In some embodiments, an effective amount of RAS modulating compound is an amount that ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a RAS modulating compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 µg, from about 1 µg to about 10 µg, from about 10 µg to about 50 µg, from about 50 µg to about 150 µg, from about 150 µg to about 250 µg, from about 250 µg to about 500 µg, from about 500 µg to about 750 µg, from about 750 µg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

In some embodiments, a single dose of the subject compound is administered. In other embodiments, multiple doses of the subject compound are administered. Where multiple doses are administered over a period of time, the RAS modulating compound is administered twice daily (qid), daily (qd), every other day (qod), every third day, three times per week (tiw), or twice per week (biw) over a period of time. For example, a compound is administered qid, qd, qod, tiw, or biw over a period of from one day to about 2 years or more. For example, a compound is administered at any of the aforementioned frequencies for one week, two weeks, one month, two months, six months, one year, or two years, or more, depending on various factors.

Any of a variety of methods can be used to determine whether a treatment method is effective. For example, a biological sample obtained from an individual who has been treated with a subject method can be assayed for the presence and/or level of cells including a target RAS. Assessment of the effectiveness of the methods of treatment on the subject can include assessment of the subject before, during and/or after treatment, using any convenient methods. Aspects of the subject methods further include a step of assessing the therapeutic response of the subject to the treatment.

In some embodiments, the method includes assessing the condition of the subject, including diagnosing or assessing one or more symptoms of the subject which are associated with the disease or condition of interest being treated (e.g., as described herein). In some embodiments, the method includes obtaining a biological sample from the subject and assaying the sample, e.g., for the presence of a mutant RAS or for the presence of cells that are associated with the disease or condition of interest (e.g., as described herein). The sample can be a cellular sample. In some cases, the sample is a biopsy. The assessment step(s) of the subject method can be performed at one or more times before, during and/or after administration of the subject compounds, using any convenient methods. In certain cases, the assessment step includes identification of cancer cells including a kRAS mutation. The determining step can include identification of cancer cells including a hRAS mutation. In certain instances, assessing the subject include diagnosing whether the subject has a MYH associated polyposis. In certain cases, assessing the subject includes identifying cells that include a mutant hRAS or nRAS.

Combination Therapy

Aspects of the present disclosure further include combination therapies. In certain embodiments, the subject method includes administering a therapeutically effective amount of one or more additional active agents. By combination therapy is meant that a RAS modulating compound (e.g., as described herein) can be used in a combination with another therapeutic agent to treat a single disease or condition. In particular embodiments, a compound of the present disclosure is administered concurrently with the administration of another therapeutic agent, which can be administered as a component of a composition including the compound of the present disclosure or as a component of a different composition. In certain embodiments, a composition including a compound of the present disclosure is administered prior or subsequent to administration of another therapeutic agent.

The subject compounds can be administered in combination with other therapeutic agents in a variety of therapeutic applications. Therapeutic applications of interest for combination therapy include those applications in which activity of a mutant RAS is the cause or a compounding factor in disease progression. As such, the subject compounds find use in combination therapies in which the inhibition of a target RAS in the subject is desired. Examples of disease conditions which may be treated by a combination therapy including a subject compound include, but are not limited to, cancer and MYH associated polyposis.

The subject RAS modulating compounds can be used jointly with any agent useful in the treatment of a neoplastic condition, such as anti-cancer agents and anti-tumor agents. One class of anti-cancer agents of interest includes chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation.

Agents of interest which can be used in jointly with the subject RAS modulating compounds include, but are not limited to, Cancer chemotherapeutic agents, Agents that act to reduce cellular proliferation, Antimetabolite agents, Microtubule affecting agents, Hormone modulators and steroids, natural products and Biological response modifiers, e.g., as described in greater detail below.

Cancer chemotherapeutic agents include non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones. Peptidic compounds can also be used. Suitable cancer chemotherapeutic agents include dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. For example, dolastatin 10 or auristatin PE can be included in an antibody-drug conjugate of the present disclosure. Suitable cancer chemotherapeutic agents also include maytansinoids and active analogs and derivatives thereof (see, e.g., EP 1391213; and Liu et al 1996 Proc. Natl. Acad. Sci. USA 93:8618-8623); duocarmycins and active analogs and derivatives thereof (e.g., including the synthetic analogues, KW-2189 and CB 1-TM1); and benzodiazepines and active analogs and derivatives thereof (e.g., pyrrolobenzodiazepine (PBD).

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere@), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; aziranopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine. Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere@), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex@. Estrogens stimulate proliferation and differentiation; therefore compounds that bind to the estrogen receptor are used to block this activity. Corticosteroids may inhibit T cell proliferation.

Other suitable chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa@ (ZD 1839, 4-(3-chloro-4-fluorophenylamino)-7-methoxy-6-(3-(4-morpholinyl)propoxy)quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from Taxus brevifolia; or T-1912 from Taxus yannanensis). Paclitaxel should be understood to refer to not only the common chemically available form of paclitaxel, but analogs and derivatives (e.g., Taxotere□ docetaxel, as noted above) and paclitaxel conjugates (e.g., paclitaxel-PEG, paclitaxel-dextran, or paclitaxel-xylose). Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ; (8) colony-stimulating factors; and (9) inhibitors of angiogenesis.

Utility

The RAS modulating compounds, e.g., as described herein, find use in a variety of applications. Applications of interest include, but are not limited to: therapeutic applications and research applications. RAS modulating compounds of the present disclosure and pharmaceutical compositions including the same find use in a variety of therapeutic applications. Therapeutic applications of interest include those applications in which a target RAS GTPase activity is the cause or a compounding factor in disease progression. As such, the subject compounds find use in the treatment of a variety of different conditions in which the modulation of a target RAS in the host is desired. Examples of disease conditions which may be treated with compounds of the invention include, but are not limited to: cancer, MYH associated polyposis and RASopathies.

The subject compounds and compositions find use in treatment of a variety of cancers, including but not limited to, pancreatic cancer, colon cancer, endometrial cancer, lung adenocarcinoma, skin cancer, acute myeloid leukemia (AML) and multiple myeloma. In certain instances, the target RAS is a mutated kRAS implicated in pancreatic cancers, colon cancers, endometrial cancers, lung adenocarcinomas, eg, non-small cell lung carcinoma (NSCLC), skin cancers, acute myeloid leukemia (AML) liquid tumors or a multiple myeloma cancer.

The subject compounds and compositions find use in treatment of MYH associated polyposis, a hereditary condition characterized by a tendency to develop multiple adenomatous colon polyps with a concomitant increased risk of colorectal cancer. In some instances, patients who may be treated according to the subject methods also possess a mutated kRAS gene/protein. The subject compounds and compositions also find use in treatment of a genetic condition termed RASopathy, as described by Niemeyer CM (RAS diseases in children. Haematologica. 2014; 99:1653-62). In such applications, the patient can be one that has a kRAS, hRAS or nRAS mutation, such as a C1 2V mutation.

The subject compounds find use in a variety of research applications including the identification and testing of candidate RAS modulating compounds (e.g., for pharmaceutical development) and performing research on disease conditions of interest in which the activity of a target RAS GTPase is implicated. Research applications of interest can involve use of the subject compounds in a variety of in vitro assays including high throughput screening assays, potency assays, and competitive inhibition assays where the subject compounds can be useful as a control compound or as a tool in the investigation the pathology of cells of interest.

Systems and Kits

Also provided are kits that include RAS modulating compounds (e.g., as described herein). Systems of the present disclosure include collections of active agents brought together, e.g., by a health care practitioner, for administration to a subject, such as a patient. Such systems may include a RAS modulating compound and one or more additional active agents (e.g., as described herein). Kits that include RAS modulating compounds which are provided that may include one or more dosages of a RAS modulating compound, and optionally one or more dosages of one or more additional active agents. Conveniently, the formulations may be provided in a unit dosage format. In such kits, in addition to the containers containing the formulation(s), e.g. unit doses, is an informational package insert describing the use of the subject formulations in the methods of the invention, e.g., instructions for using the subject unit doses to treat cellular proliferative disease conditions. These instructions may be present in the subject systems and kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Screening

RAS modulating compounds of interest were identified using screening of various chemical libraries in cell culture using cancer cells whose growth is driven by mutated RAS, eg, SW480 cells whose growth is driven by a G12V mutation in the kRAS gene/protein (www.atcc.org/~/media/PDFs/Culture %20Guides/Cell_Lines_by_Gene_Mutation.ashx) followed by computational docking of potential hits to the recently published structures of guanylyl imidodiphosphate-bound hRAS-G12V & hRAS-wt (PDB code: 4EFM & 4EFL, respectively) (Muraoka et al., Crystal structures of the state 1 conformations of the GTP-bound H-Ras protein and its oncogenic G1 2V and Q61 L mutants. Febs Lett. 2012. 586: 1715-1718).

Structurally, RAS proteins contain a G domain (Wittinghofer A, Vetter IR. Structure-function relationships of the G domain, a canonical switch motif. Annu Rev Biochem. 2011; 80:943-71) which is responsible for the enzymatic activity of RAS: guanine nucleotide binding and GTPase hydrolysis. It also contains a C-terminal extension which may be post-translationally modified and is responsible for targeting the protein to the membrane. The G domain is approximately 19 kDa in size and it contains a phosphate binding loop (P-loop) (Chen et al., Computational analysis of KRAS mutations: implications for different effects on the KRAS p.G12D and p.G13D mutations. PLoS One. 2013; 8: e55793). The P-loop represents the pocket where the nucleotides are bound in the protein, and this is the rigid part of the domain with conserved amino acid residues which are essential for nucleotide binding and hydrolysis (Glycine-12, Threonine-26 and Lysine-16). The G domain also contains the so-called Switch I (residues 30-40) and Switch II (residues 60-76) regions, both of which are the dynamic parts of the protein that are often represented as the "spring-loaded" mechanism because of their ability to switch between the resting and loaded state (Muraoka et al., Crystal structures of the state 1 conformations of the GTP-bound H-Ras protein and its oncogenic G1 2V and Q61 L mutants. FEBS Lett. 2012; 586:1715-8). The key interaction is the hydrogen bonds formed by Threonine-35 and Glycine-60 with the α-phosphate of GTP which maintain Switch 1 and Switch 2 regions, respectively, in their active conformation. After hydrolysis of GTP and release of phosphate, these two hydrogen bonds relax into the inactive GDP conformation.

Systematic drug screening of chemical libraries using cultured cancer cells, mutant flies, and computational analyses using Autodock of hits from the screen were used to identify and characterize compounds with anti-RAS activity and anti-cancer.

Synthesis

General Procedures for the Synthesis of Compounds of interest are provided below. In the reaction schemes, "R" refers to the substituents of interest for the particular compound that is the target of the synthetic effort.

Scheme 2: Compounds related to Formula 2

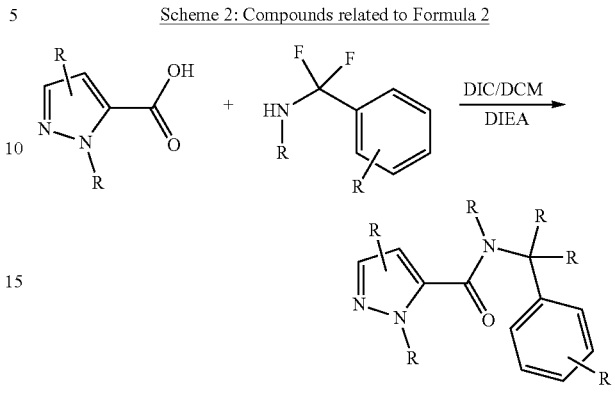

The appropriate carboxylic acid (1 mmole), diisopropylcarbodiimide (DIC, 2 mmole)) and diisopropyl ethyl amine (DIEA, 2 mmole) dissolved in dichloromethane (DCM) is treated with the appropriate benzyl amine (1 mmole) dissolved in DCM and stirred at room temperature. The progress of the reaction is monitored by thin layer chromatography (TLC) on silica gel using 10-50% ethyl acetate/hexane as the mobile phase. When the reaction is complete, the solvent is removed by rotary evaporation and the product purified by column chromatography on silica gel using ethyl acetate/hexane solvent mixture.

Synthesis of (4-(5-methyl-1,2,4-oxadiazol-3-yl)phenyl)methanamine hydrochloride

Step 1: Synthesis of tert-butyl (E)-(4—(N'-hydroxycarbamimidoyl)benzyl)carbamate: tert-Butyl (4-cyanobenzyl) carbamate (1 g, 4 mmol) was suspended in 10 mL ethanol and heated to 80° C. To the solution was added 10 mL of aqueous hydroxylamine and the mixture was heated for 3 hours and allowed to cool to room temperature and stirred overnight. After concentration the residue was concentrated to half volume, and product extracted with ethyl acetate (3×15 ml). The combined organic layer was washed with brine (15 mL), dried over anhydrous sodium sulfate, and the solvent was evaporated to dryness to yield white solid (890 mg) which was taken to the next step. Mass Spec, MH$^+$=266

Step 2: Synthesis of tert-butyl (4-(5-methyl-1,2,4-oxadiazol-3-yl)benzyl)carbamate: The product from Step 1 dissolved in tetrahydrofuran (THF, 15 mL) was treated with trimethylamine (6.6 mmol), acetic anhydride (4 mmol) and the mixture was refluxed overnight. TLC on silica gel using 30% ethyl acetate in hexane showed the reaction was complete. Following solvent evaporation, the product was purified by column chromatography on silica gel to yield white solid (760 mg). Mass Spec MH$^+$=290.

Step 3: Synthesis of (4-(5-methyl-1,2,4-oxadiazol-3-yl) phenyl)methanamine hydrochloride: The product from Step 2 was dissolved in 5 ml dioxane and treated with 5 ml of 4M HCl in dioxane. After stirring for 3 hours the solvent was evaporated and the residue dried under vacuum to yield 550 mg of desired product. Mass Spec, MH$^+$=190

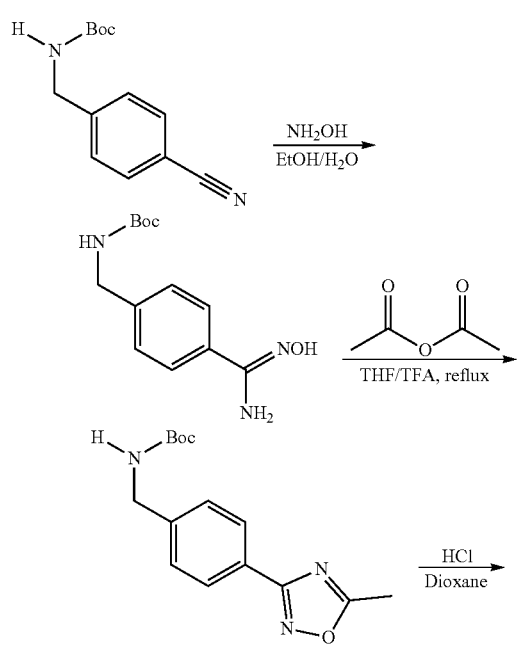

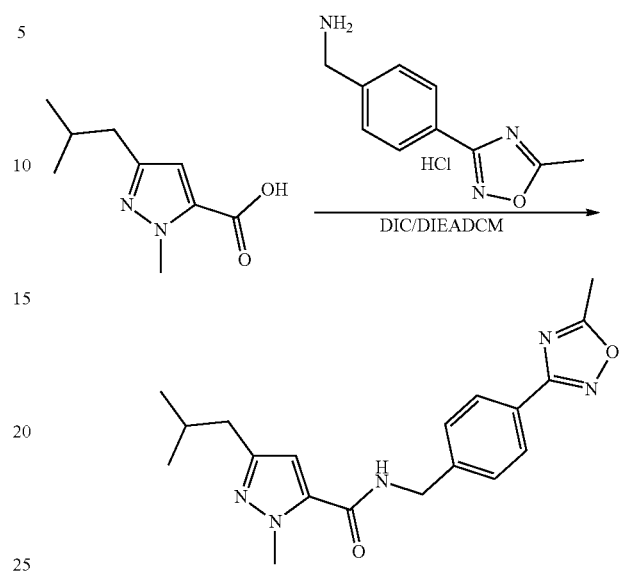

Synthesis of 3-isobutyl-1-methyl-N-(4-(5-methyl-1,2,4-oxadiazol-3-yl)benzyl)-1H-pyrazole-5-carboxamide (Structure 2, compound 1)

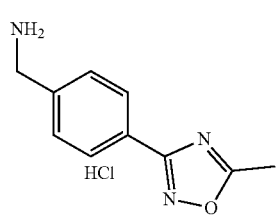

A solution of 3-isobutyl-1-methyl-1 H-pyrazole-5-carboxylic acid (445 mg, 2.4 mmol) and DIEA (7.2 mmol) in DCM (5 mL) was treated with DIC (2.4 mmol) and the mixture stirred for 15 minutes. The solution was then added to a suspension of (4-(5-methyl-1,2,4-oxadiazol-3-yl)phenyl)methanamine hydrochloride (550 mg, 2.4 mmol) and the mixture was stirred at room temperature overnight. After filtering through a glass frit, the solvent was evaporated the product purified by column chromatography on silica gel column (0-50% ethyl acetate in hexane) to afford 800 mg of white solid. Mass Spec, MH$^+$=354

Synthesis of N-(4-(5-(tert-Butyl)-1,2,4-oxadiazol-3-yl)benzyl)-3-isobutyl-1-methyl-1H-pyrazole-5-carbamide

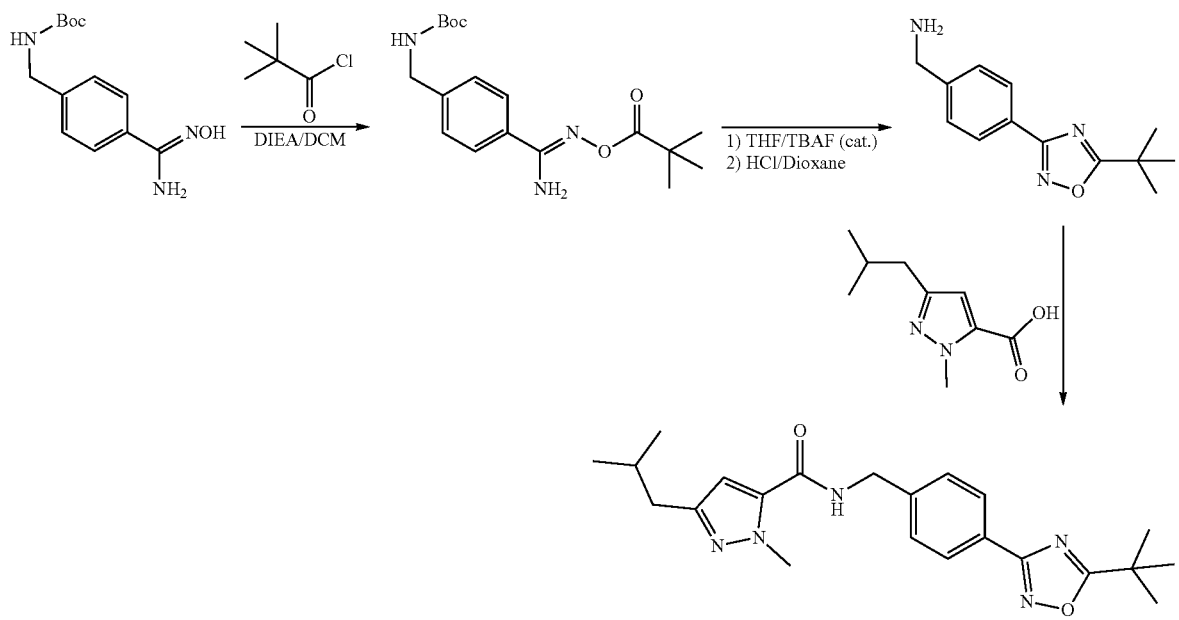

Step 1: tert-butyl-(4—(N'-hydroxycarbamimidoyl)benzyl)carbamate (2.65 g, 10 mmol) and DIEA (3.5 mL, 20 mmol) dissolved in DCM (40 mL) and cooled on ice bath was treated with a solution of pivaloyl chloride (1.33 g, 11 mmol) in DCM (10 mL) dropwise. The ice bath was removed and the mixture stirred overnight at ambient temperature. The reaction mixture was washed with 25 mL portions of water and brine. The organic layer was dried over anhydrous sodium sulfate and the solvent was evaporated to yield white solid which was taken to the next step without purification.

Step 2: To the crude mixture from Step 1 dissolved in anhydrous THF (50 mL) and cooled on ice bath, 1 mL of tetrabutylammonium fluoride in THF (1 M) was added dropwise over three minutes. The reaction mixture was allowed to room to room temperature and allowed to stir for 48 hours. The solvent was evaporated by rotary evaporation and the residue dissolved in ethyl acetate (50 mL) was washed with water (25 mL) and brine (15 mL). The organic layer was dried over anhydrous sodium sulfate and the solvent was evaporated to yield light brown oil. The desired tert-butyl (4-(5-(tert-butyl)-1,2,4-oxadiazol-3-yl)benzyl)carbamate was purified by column chromatography on silica gel column using 5-30% ethyl acetate in hexane to yield white solid (2.68 g). The white solid was dissolved in 10 mL dioxane and treated with 10 mL of 4 M HCl in dioxane and the mixture was stirred for 3 hours. The solvent was evaporated to dryness to yield the desired the product as hydrochloride salt (off-white solid, 2.14 g).

Synthesis of Compound 4: N-(4-(5-(tert-butyl)-1,2,4-oxadiazol-3-yl)benzyl)-3-(isopropylamino)pyrrolidine-1-carboxamide (see Formula H)

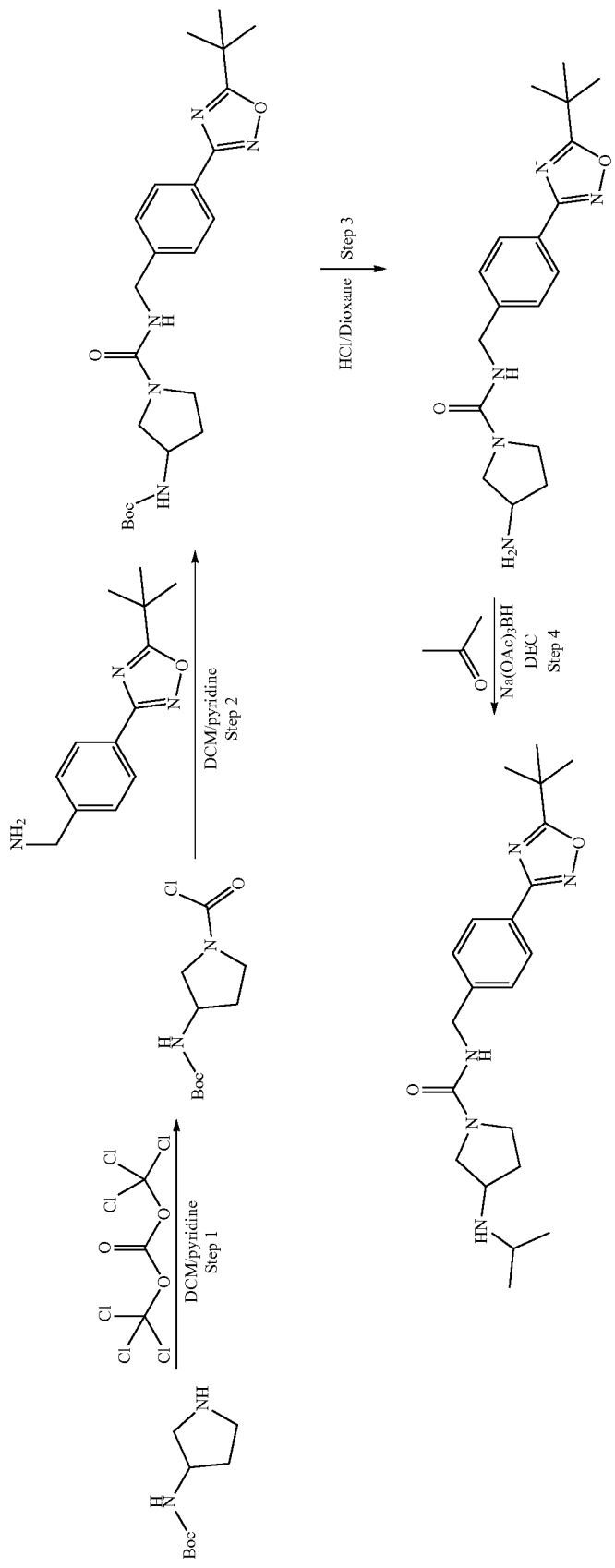

Step 1: tert-butyl (1-(chlorocarbonyl)pyrrolidin-3-yl)carbamate. A solution of tert-Butyl pyrrolidin-3-ylcarbamate (0.5.0 g, 2.7 mmol) and pyridine (0.44 mL, 2.7 mmol) in DCM (10 mL) was cooled to about 0° C. After adding triphosgene (0.308 g, 1 mmol) the reaction mixture was allowed to slowly warm to room temperature and stirred for about 2 h. After diluting with DCM (30 mL) the solution was washed with water (15 mL) and 1 N HCl (10 mL). The organic layer was dried over anhydrous sodium sulfate, filtered, and concentrated to dryness under reduced pressure. The mixture was stirred for about 1 h while slowly warming to ambient temperature. To the reaction solution was added DCM (50 mL) and the solution was washed with water (20 mL) and HCl (1N, 10 mL). The organic portion was separated, dried over anhydrous MgSO$_4$, filtered, and concentrated to dryness under reduced pressure to give tert-butyl 1-(chlorocarbonyl)pyrrolidin-3-ylcarbamate (0.64 g) as a yellow oil.

Step 2: tert-butyl (1-((4-(5-(tert-butyl)-1,2,4-oxadiazol-3-yl)benzyl)carbamoyl)pyrrolidin-3-yl)carbamate. (4-(5-(tert-Butyl)-1,2,4-oxadiazol-3-yl)phenyl)methanamine (0.3 g, 1.3 mmol) and DIEA (0.45 mL, 2.6 mmol) were dissolved in DCM (5 mL) and cooled to 0° C. A solution of tert-butyl 1-(chlorocarbonyl)pyrrolidin-3-ylcarbamate (0.32 g, 1.3 mmol) in DCM (3 mL) was added dropwise. The reaction mixture was allowed to slowly warm to room temperature and stirred overnight. After removing the solvent under reduced pressure the desired product was obtained (0.52 g) after purification on silica gel column using 20-50% ethyl acetate in hexane as the mobile phase. Mass Spec, MH$^+$=444.

Step 3: 3-amino-N-(4-(5-(tert-butyl)-1,2,4-oxadiazol-3-yl)benzyl)pyrrolidine-1-carboxamide. The product from Step 2 was suspended in 4 M HCl in dioxane (10 mL) for 1 h. The solvent was evaporated and the residue suspended in DCM (25 mL) and washed with 1 N NaOH (10 mL). The organic was layer dried over anhydrous sodium sulfate, filtered, and the solvent was evaporated under reduced pressure to give the desired product as an off-white solid (0.38 g). Mass Spec, M+H=344.

Step 4. N-(4-(5-(tert-butyl)-1,2,4-oxadiazol-3-yl)benzyl)-3-(isopropylamino)pyrrolidine-1-carboxamide. The product from Step 3 (0.38 g, 1.1 mmol), acetone (0.1 mL, 1.4 mmol) and acetic acid (0.015 mL) were dissolved in DCE (5 mL). The solution was treated with NaBH(OAc)$_3$ (0.35 g, 1.65 mmol) and stirred at room temperature overnight. The reaction mixture was diluted with DCM (15 mL) and washed with 1 M NaOH (10 mL). The aqueous layer was extracted with DCM (10 mL). The combined organic extract was concentrated and the desire product was purified by column chromatography on silica gel (mobile phase: 5% methanol, 0.5% TEA in DCM). Mass Spec, M+H=386.

Compound related to Structure 3 (Compound 2)
Synthesis of Compound of Formula 3 [4-(4-((1-phenyl-1H-pyrazol-4-yl)
methyl)piperazin-1-yl)quinazoline)]

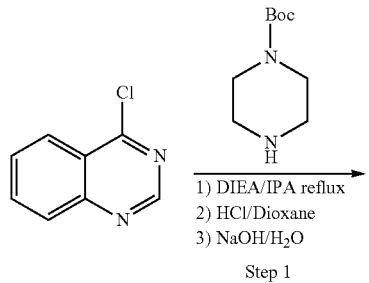

1) DIEA/IPA reflux
2) HCl/Dioxane
3) NaOH/H$_2$O

Step 1

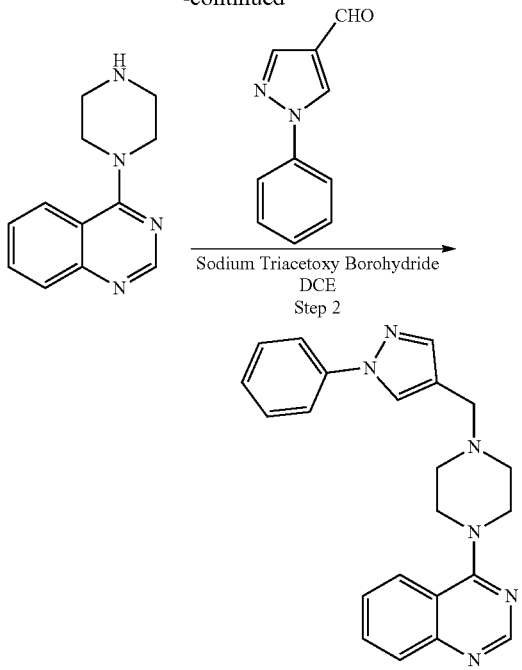

Structure 3

Step1: 4-Choloroquinazoline (2.0 g, 12.2 mmol), tert-butyl piperazine-1-carboxylate (1.96 g, 12.8 mmol), and N,N-diisopropylethylamine (3.2 mL, 18.4 mmol) were suspended in isopropyl alcohol and refluxed overnight. The reaction mixture was concentrated to half volume by rotary evaporation, diluted with 50 mL ethyl acetate, washed with saturated aqueous sodium bicarbonate solution, and brine. The organic layer was dried over sodium sulfate and the solvent was evaporated to yield white solid (3.6 g; Mass Spec M+H=314). The crude product dissolved in dioxane (15 mL) and treated with 4 M hydrogen chloride solution in dioxane (15 mL) was stirred at room temperature for four hours. After removing the solvent by rotary evaporation, the residue was suspended in ethyl acetate (50 mL), washed with saturated sodium bicarbonate solution, the aqueous layer was extracted with ethyl acetate (3×15 mL). The organic extracts were combined, washed with brine, dried over sodium sulfate and the solvent was evaporated to yield 4-(piperazin-1-yl)quinazoline as an off-white solid (2.3 g; Mass Spec, MH$^+$=215).

Step 2: A solution of 4-(Piperazin-1-yl)quinazoline (1.0 g, 4.7 mmol) and 1-phenyl-1 H-pyrazole-4-carbaldehyde (0.81 g, 4.7 mmol) in 1,2-dichloroethane (20 mL) was treated with sodium triacetoxy borohydride (1.5 g, 7 mmol) and the reaction mixture was stirred overnight. The mixture was diluted with dichloromethane (30 mL) and washed sequentially with 25 mL portions of 1 M NaOH, water and brine. The organic layer was evaporated and the desired product was purified by column chromatography on silica gel column using ethyl acetate/hexane (10-50%) as the mobile phase the desired product was obtained as a white solid (1.5 g). Mass Spec, M+H=371.

In Vitro Assays
Cytotoxicity Assays

Compounds were assayed for inhibition of cell proliferation and killing cancer cells. Cytotoxicity assays were conducted according to the following general procedure. SW480, SW48, SW900, SW620 were all maintained in Leibowitz L15 media supplemented with 10% fetal bovine serum and 1% PenStrep and grown in a 37° C. incubator without supplemental $CO_2$. Capan-1 cells were maintained in Iscove's Modified Dulbecco's Medium (ATCC 30-2005) containing 20% fetal bovine serum and 1% PenStrep and grown in a 37° C. incubator containing 5% $CO_2$.

Cells were plated into 96 well flat bottom plates (1 million/plate, ~10,000/well, 250 µL media/well). The cells were allowed to settle and adhere to plate bottom overnight. 1 µL from 10 mM library (located in columns 2-11) transferred to SW480 plate and 100 µM oncrasin was used for a positive control in wells E1, F1, G1, and H1. (Thus compounds were screened at a concentration of 40 µM.) Plates were incubated 48 hours at 37° C. with no supplementary $CO_2$. Plates were allowed to come to room temperature. 150 µL was removed from each well and 100 µL room temperature CellTiter-Glo 2.0 reagent (Promega, G924C) was added. Plates shaken for 2 minutes, then allowed to rest 15 minutes. Luminescence was read with FLx800 (BioTek Instruments). The average luminescence value of media alone wells was set to 100% and the average value of oncrasin treated wells was set to 0%. Compounds that were found to give cell viability of less than 25% were chosen for retesting.

Retesting of compounds was performed at concentrations of 40 and 10 µM. The 40 µM concentration was set up as above but 50 µL media plus compounds were removed and placed in 96 well flat bottom plates containing 1 million SW480 cells (~10,000/well) and 150 µL media per well. (Both concentrations have 200 µL media/well.) Plates incubated 48 hours at 37° C. with no supplemental $CO_2$. Plates were allowed to come to room temperature. 100 µL was removed from each well and 100 µL room temperature CellTiter-Glo 2.0 reagent (Promega, 0924C) was added. Plates shaken for 2 minutes, then allowed to rest 15 minutes. Luminescence was read with FLx800 (BioTek Instruments).

For dose-response assays, SW480 cells were plated into 96 well plates (1 million/plate, ~10,000/well, 250 µL media/well). Cells were allowed to settle and adhere to plate bottom overnight. Compounds were placed in 500 uL media and mixed. Then 250 µL compounds+media was placed in an intermediate plate in row A. Rows 8 through H were filled with 125 µL media. 125 µL from row A was serially diluted down the plate to row G. (Row H reserved for controls.) Media was aspirated from plates containing SW480 cells and replaced with 100 µL media+compounds from intermediate plate. Plates were incubated 48 hours at 37° C. with no supplementary $C_2$. Plates were allowed to come to room temperature and 100 µL room temperature CellTiter-Glo 2.0 reagent (Promega, 0924C) was added to each well. Plates shaken for 2 minutes, then allowed to rest 15 minutes. Luminescence was read with FLx800 (BioTek Instruments).

Cell Morphology Assay

An assay was performed (see e.g., Kato-Stankiewicz et al., Inhibitors of RAS/Raf-1 interaction identified by two-hybrid screening revert RAS-dependent transformation phenotypes in human cancer cells. Proc Natl Acad Sci USA. 2002; 99: 14398-403) to evaluate the ability of an inhibitor to dampen the RAS/RAF/MEK/ERK pathway and provide a reversion of cell appearance from a rounded to a flat, elongated morphology (Paterson et al., Activated nRAS controls the transformed phenotype of HT1080 human fibrosarcoma cells. Cell. 1987 Dec. 4; 51(5):803-12). HT-1080 cells were maintained in DMEM containing 10% fetal bovine serum. For the morphology assays, the cells were plated at 400,000 per plate in a 6-well plate and grown overnight at 37° C. Media was removed and replaced with fresh media with or without Structure 2. The plate was incubated an additional 24 hours at 37° C. Cells were washed 2 times with warm PBS and fixed using 3.7% formaldehyde in PBS for 10 minutes at room temperature. After washing 2 times with PBS extraction was performed in 0.1% Triton X-100 in PBS for 3-5 minutes. After 2 PBS washes, cells were stained for 20 minutes with Alexa Fluor 488 Phalloidin in methanol (Life Technologies) diluted 40-fold in PBS. Cells were then washed 2 times with PBS and imaged using a Zeiss Axiovert 25 fluorescence microscope.

Figure 7:
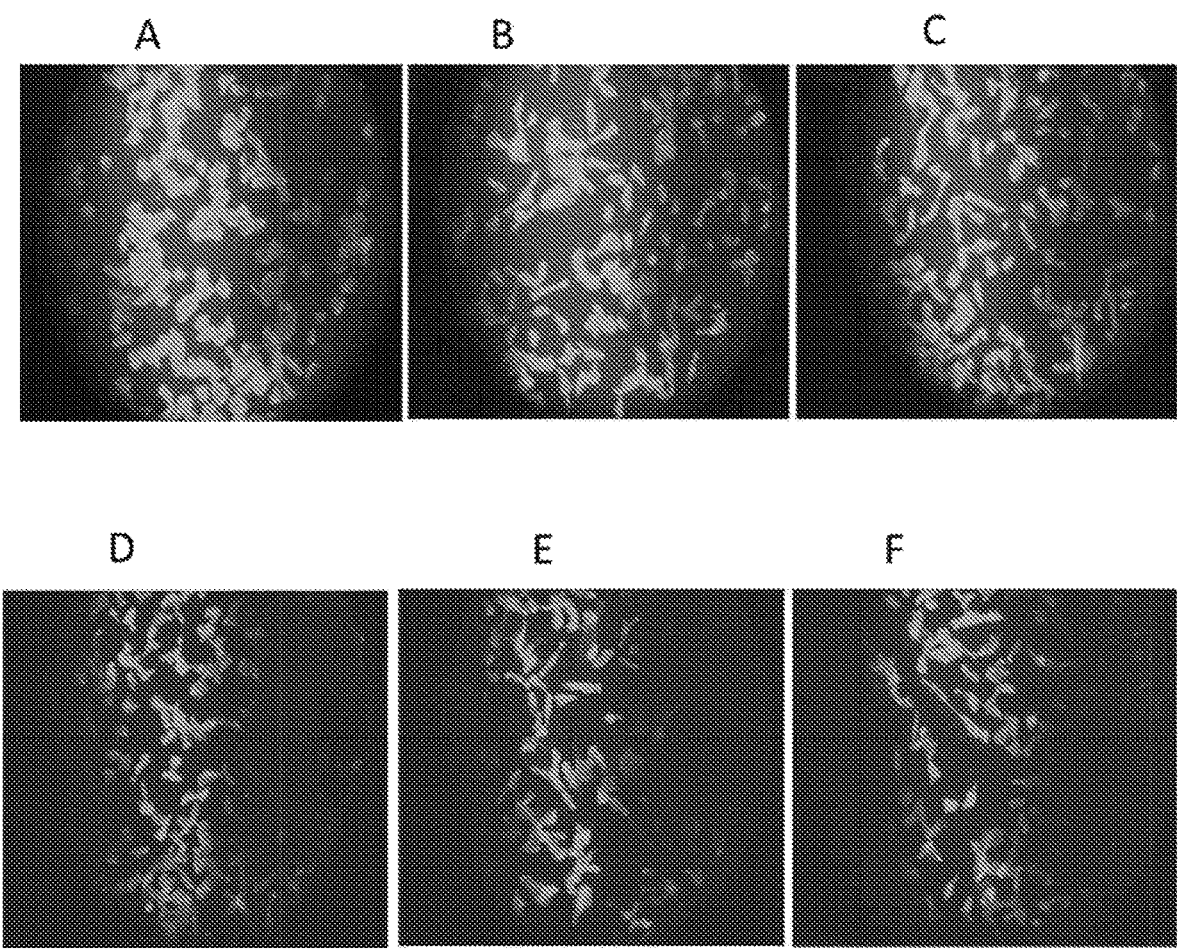
FIG. 7, panels A-F, illustrate the effect of an exemplary compound of Structure 2 on the HT-1080 cells in a cell morphology assay. Effect of Structure 2 on the HT-1080 cells in cell morphology assay. HT1080 cells were seeded in 6-well plates at 300,000 per plate, incubated overnight and various amounts of Structure 2 (compound 1) in the DMSO vehicle or vehicle control added. After 24 hours, cells were washed, fixed with formaldehyde, stained with Alexa Fluor 488 Phalloidin and imaged using a fluorescence microscope. Panel A provides results with vehicle control (DMSO), Panel B provides results with 1.2 μM, Panel C provides results with 3.7 μM, Panel D provides results with 11 μM, Panel E provides results with 33 μM and Panel F provides results with 100 μM.

As illustrated in FIG. 7, the compound of Structure 2 produced reversion of cell phenotype from the rounded to the flatter more elongated morphology that is consistent with inhibition of the RAS/RAF/MEK/ERK pathway.

Selectivity of Compounds for kRAS G12V

Figure 2:
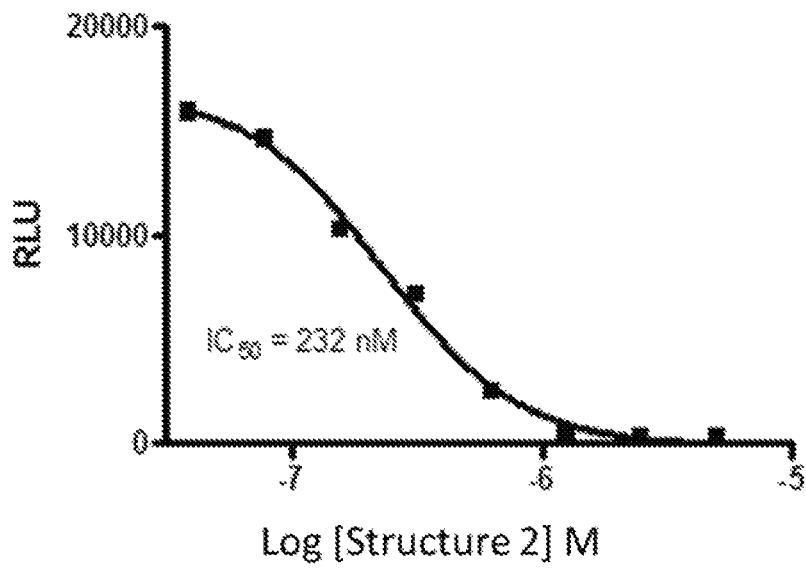
FIG. 2, panels A-B, illustrate the cytotoxicity of Structure 2 and Structure 3 on SW480 cells. The cytotoxicity of compounds of interest was tested against the human colon cancer cell line SW480 as described in the experimental section. SW480 cells express a mutant G1 2V kRAS. Compounds were incubated with cells for 48 hours and the assay was developed using Cell Titer Glo 2.0. $IC_{50}$ vales were determined using GraphPad Prism 4.
Figure 2:
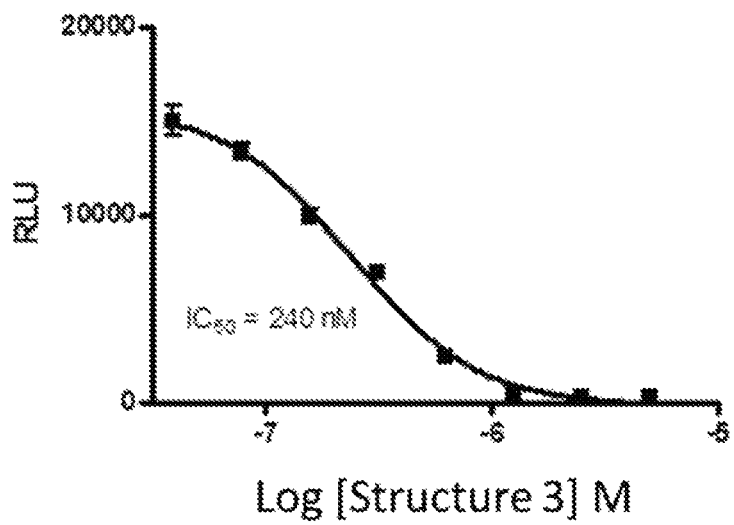
Figure 4:
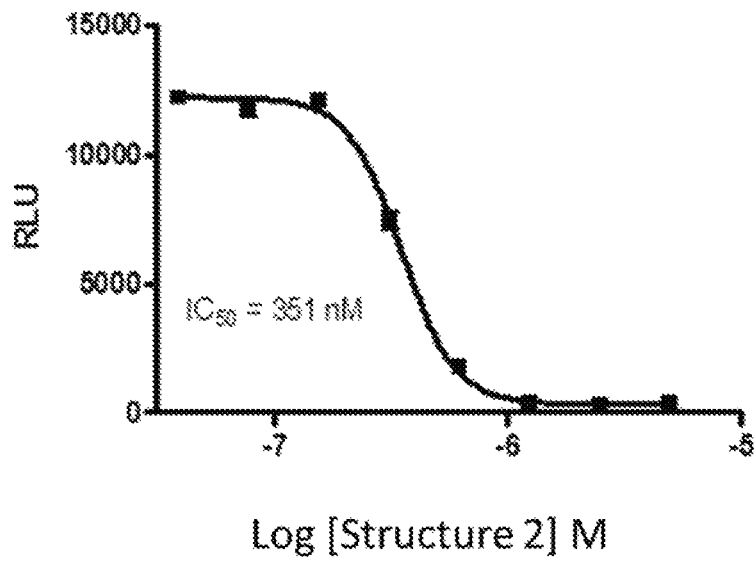
FIG. 4, panels A-B, illustrates the cytotoxicity of Structure 2 and Structure 3 on SW900 cells. The cytotoxicity of compounds of interest were tested against the human lung cancer cell line SW900 as described in the experimental section. SW900 cells express a G1 2V mutant kRAS. Compounds were incubated with cells for 48 hours and the assay was developed using Cell Titer Glo 2.0. $IC_{50}$ vales were determined using GraphPad Prism 4.
Figure 4:
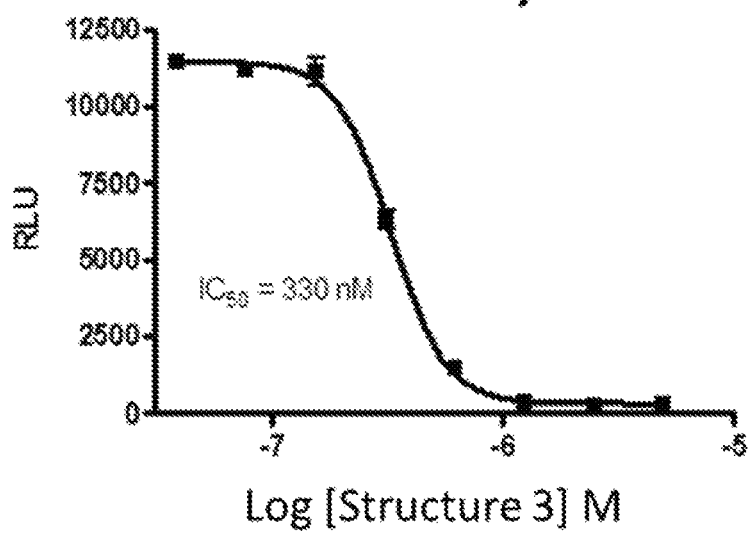
Figure 5:
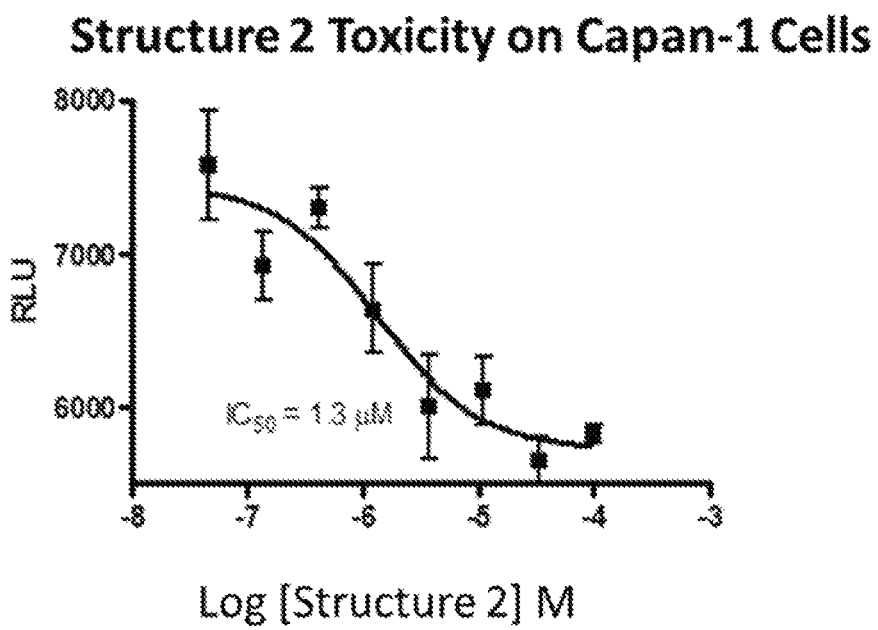
FIG. 5, panels A-B, illustrates the cytotoxicity of Structure 2 and Structure 3 on Capan-1 cells. The cytotoxicity of compounds of interest were tested against the human pancreatic cancer cell line Capan-1 as described in the experimental section. Capan-1 cells express a mutant G12V kRAS. Compounds were incubated with cells for 48 hours and the assay was developed using Cell Titer Glo 2.0. $IC_{50}$ vales were determined using GraphPad Prism 4.
Figure 5:
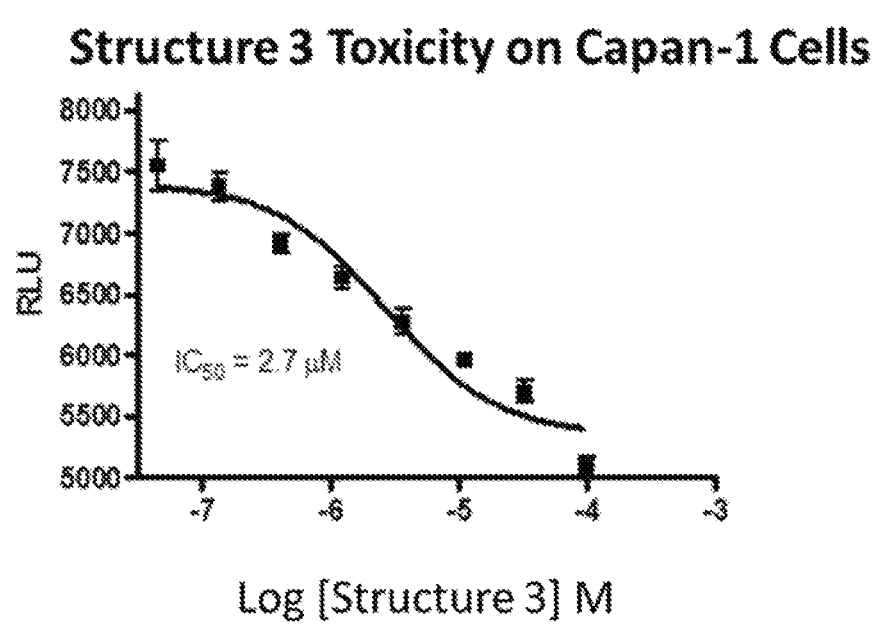
Figure 6:
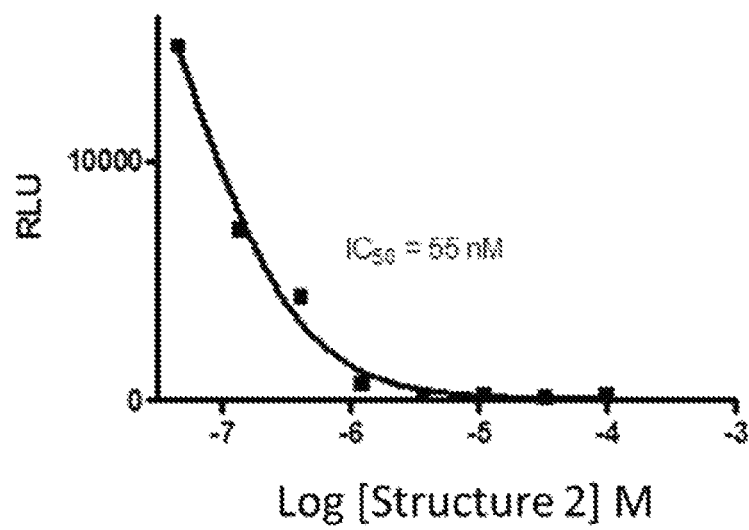
FIG. 6, panels A-B, illustrate the cytotoxicity of Structure 2 and Structure 3 on SW620 Cells. The cytotoxicity of compounds of interest were tested against the human colon cancer cell line SW620 as described in the experimental section. SW620 cells express a mutant G12V kRAS. Compounds were incubated with cells for 48 hours and the assay was developed using Cell Titer Glo 2.0. $IC_{50}$ values were determined using GraphPad Prism4.
Figure 6:
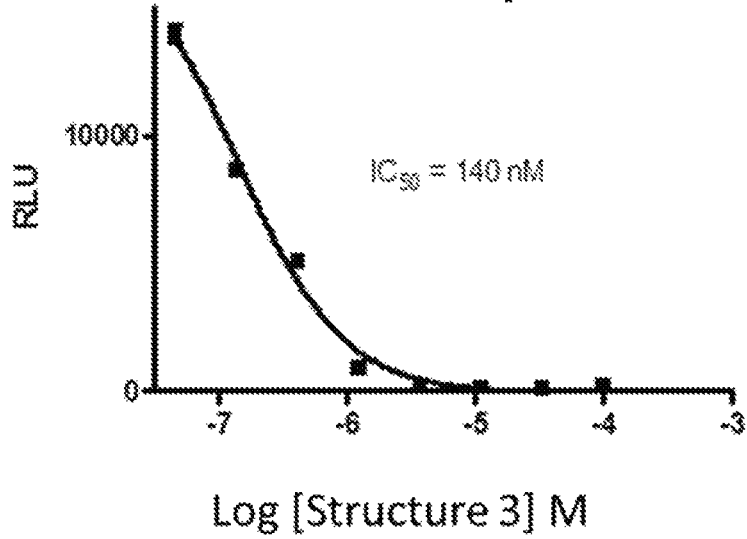

The activity and selectivity of Structure 2 was tested against both genetically normal cells and cells expressing kRAS with the G12V mutation. Structure 2 was cytotoxic to SW480 cells (FIG. 2), a human colon cancer cell line expressing kRAS G1 2V, with an $IC_{50}$ of 232 nM. Structure 2 was also tested against SW48 cells (FIG. 3), a human colon cancer cell line expressing wild type kRAS, and found to have an $IC_{50}$ of 607 nM. Against SW900 cells (FIG. 4), a human lung cancer cell expressing the kRAS G1 2V mutation, Structure 2 had an $IC_{50}$ of 351 nM. Structure 2 was tested against Capan 1 (FIG. 5), a human pancreatic cancer cell line expressing the kRAS G12V mutation, where it had an $IC_{50}$ of 1.3 µM. Structure 2 was also tested against SW620 (FIG. 6), another human colon cancer cell line expressing the mutant G12V kRAS, where it had an $IC_{50}$ of 55 nM. Structure 2 was not cytotoxic at concentrations up to 40 µM against the rat cardiomyocyte cell line H9C2. Against human lung cancer cell lines expressing wild type kRAS (H322 and A431), Structure 2 was not cytotoxic at concentrations up to 200 µM and 40 µM respectively. Against the human colon cancer cell line HT29, Structure 2 was not cytotoxic at concentrations up to 40 µM.

Figure 3:
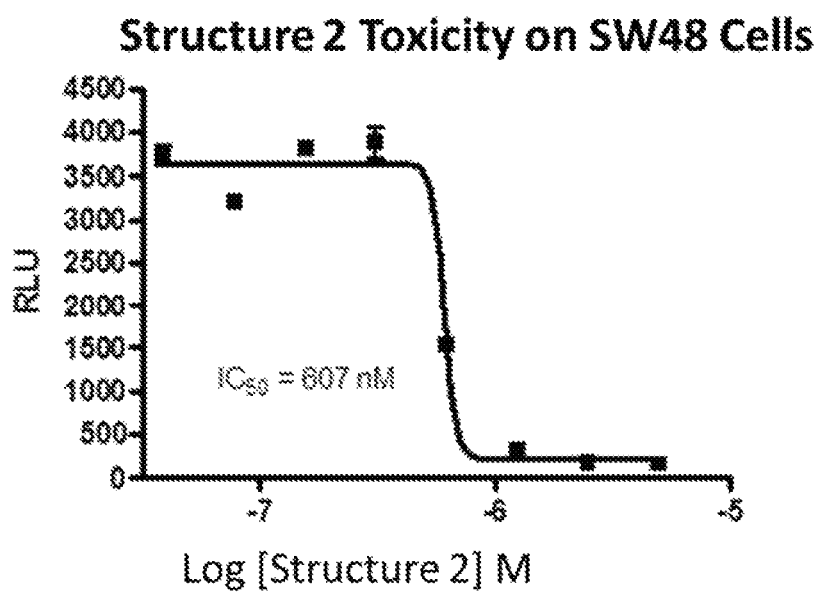
FIG. 3, panels A-B, illustrates the cytotoxicity of Structure 2 and Structure 3 on SW48 cells. The cytotoxicity of compounds of interest were tested against the human colon cancer cell line SW48 as described in the experimental section. SW48 cells express the wild type kRAS but are driven by an EGF receptor mutation G1255A. Compounds were incubated with cells for 48 hours and the assay was developed using Cell Titer Glo 2.0. $IC_{50}$ vales were determined using GraphPad Prism 4.
Figure 3:
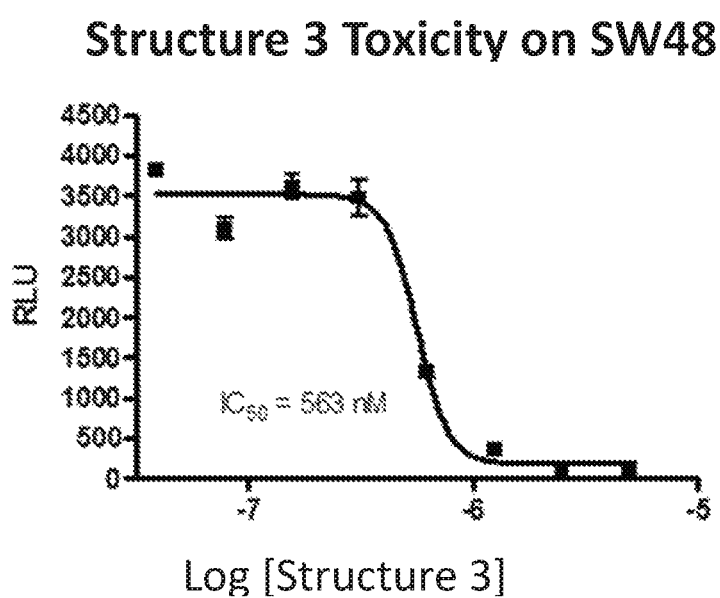

In general, the compounds killed the cells containing the G12V mutations at sub µM concentrations but not cells such as normal cells or cancer cells not expressing G1 2V. The exception was SW48 cells, a wild type kRAS cell line where Structure 2 was cytotoxic with an $IC_{50}$ of 607 nM (FIG. 3). However, SW48 cells have a mutation in the EGF receptor that keeps it continuously activated. Because kRAS is directly downstream of the EGF receptor and kRAS is an EGFR-effector, inhibition of wt kRAS would be expected to inhibit growth of this cell line.

Phosphorylated ERK Bioassay

As described herein, the main downstream target for kRAS is ERK (Samatar et al., Targeting RAS-ERK signaling in cancer: promises and challenges. Nat Rev Drug Discov. 2014; 13:928-42). kRAS activates ERK leading to phosphorylated ERK. A compound that suppresses kRAS activity is expected to lower phosphorylated ERK.

Test articles abrogate the expression of phosphorylated ERK (T202/Y204) SW480 cells were subjected to test article incubation at 3 µM for 24 hours in the presence of serum to mimic natural growth environment. Cells were extracted and total protein of samples normalized through BCA assay. Processed extracts were subjected to SDS-PAGE/Western blot and blotted for phosphorylated ERK 1/2 (T202/Y204); ERK 1/2; and α-Tubulin. Results are provided in FIG. 8. Both test articles dramatically suppressed phosphorylated ERK without affecting non-phosphorylated ERK.

Figure 8:
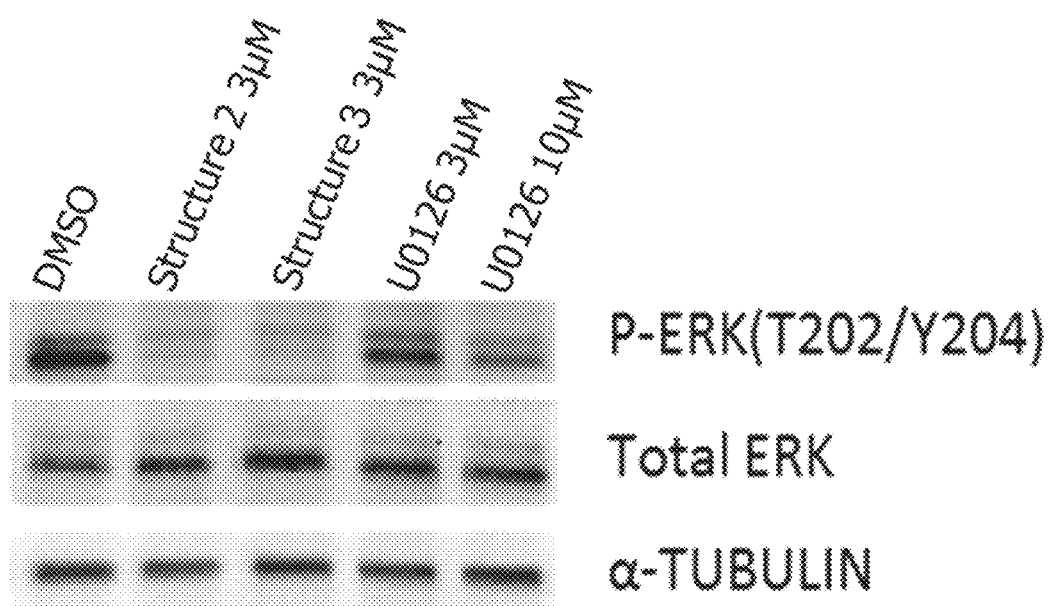
FIG. 8 illustrates the effect of Structure 2 and Structure 3 on phosphorylated ERK. Both compounds dramatically decrease phosphorylated ERK

The compound U0126 in FIG. 8 is a MEK inhibitor which is known to suppress phosphorylation of ERK. The compound was tested along with the test articles to serve as a positive control. Measurement of kRAS in this experiment and other experiments as well suggest that both test articles depleted kRAS and that this loss is possibly the reason for the lowered phosphorylated ERK.

In-Vivo Assays

Fly Assay (Karo T, Yanofsy S, Garland W, U.S. Application Ser. No. 14/911,101: Entitled: Non-Mammalian RAS Transgenic Animal Model)

Embryo preparation. GAL4 virgin ♀ were collected over a period of 3-5 days, then crossed with kRAS G12V (3M) ♂ inside a plastic condo supplied with grape agar containing yeast paste.

Flies were acclimated for 2 days and embryos present after a span of 4-5 hours were collected along with the agar plate and incubated for 24 hours. The next day, embryos were washed off the agar plate with Embryo Wash solution (120 mM NaCl, 0.03% Triton X) and resuspended in Embryo Inoculation solution (120 mM NaCl, 420 mM Sucrose, 0.05% Triton X-100). Embryos were counted and diluted to 15 embryos/10 µL. 150 embryos (100 µL) were dispensed into each vial.

Wing mounting and scoring. Flies hatch 10-12 days after the above experimental setup is performed. The resulting adult flies are submerged in a 3:1 70% ethanol: glycerol solution for 24 hours, then wings are dissected with curved Vannas spring scissors (FST #15001-08). The wings are mounted in an 80% glycerol solution on a microscope slide under coverslip seal.

Pictures of the wings were taken using an Accu-Scope microscope equipped with a digital camera and connected to a laptop containing the Accu-Scope Micrometric SE Premium software. The wings were scored according to the following scoring tree:

Wing score analysis. After each wing received a score from two independent scorers, the analysis of the scores given to the Structure 2 and 3 groups was compared to the scores given for the control group and was performed using the IBM SPSS software. It was found that scores received by the Structure 2 and 3 groups were significantly different from the control group by employing either parametric (Tukey HSD and LSD, $p<0.001$) or non-parametric (Mann Whitney, $p=0.002$) methods of analysis. An analysis of scoring data for Structure 2 is provided in Table 3.

TABLE 3

Selected results showing ability of Structure 2 to reverse crimped phenotype of flies expressing G12V in their wing

| | | | Scored 1-6 | | | | Scored 0-1 | | |
|---|---|---|---|---|---|---|---|---|---|
| Treatment | Concentration (µmolar) | Wing s(n) | Mean ± SD | Tukey HSD* | LSD* | Mann-Whitney* | Reversal Phenotype (%) | Tukey HSD* | LSD* |
| Control | 0 | 423 | 1.86 ± 0.62 | <0.001 | <0.001 | 0.002 | 8.27 | <0.001 | <0.001 |
| Structure 2 | 10 | 218 | 2.15 ± 0.95 | | | | 24.31 | | |

*p values for Tukey's honest significance difference test, Fishers least significant difference, and Mann-Whitney U test Food-drug admix preparation. Each fly vial contains 1.5 g of fly food in 4 mL water. The quantity of drug needed is calculated for a total of 4 vials, each vial containing 10 µM of Structure 2. This is equivalent to 0.014 mg of Structure 2/vial, for a total of 0.056 mg of Structure 2.

A stock solution of 0.1 mg/mL Structure 2 in ethanol is prepared. A 500-ml round bottom flask is charged with 6 g of fly food (1.5 g×4), to which is added 20 mL of ethanol, ensuring that the food is entirely covered in solvent. To this heterogeneous solution is added an appropriate amount of Structure 2 stock solution, containing the calculated required quantity, in this case 0.56 mL stock solution.

The ethanol is evaporated under reduced pressure via a rotary evaporator equipped with a bump trap. The resulting dry food is added to three vials, each containing 1.5 g, so that the experiment is performed in triplicate. The quantity is calculated initially for 4 vials, because some food will be stuck to the walls of the round bottom flask and some is also invariably lost in the bump trap during the solvent evaporation step. Control vials lacking Structure 2 or Structure 3 are also analyzed and undergo the exact same food preparation and solvent extraction procedure.

Embryo addition to vials. After all the food-drug admix is prepared and added to the respective vials, to each vial is added 4 mL of water and the vial briefly vortexed. To this liquid mixture is added the embryo solution (100 µL), the vials capped and placed in an incubator or fly room.

Figure 9:
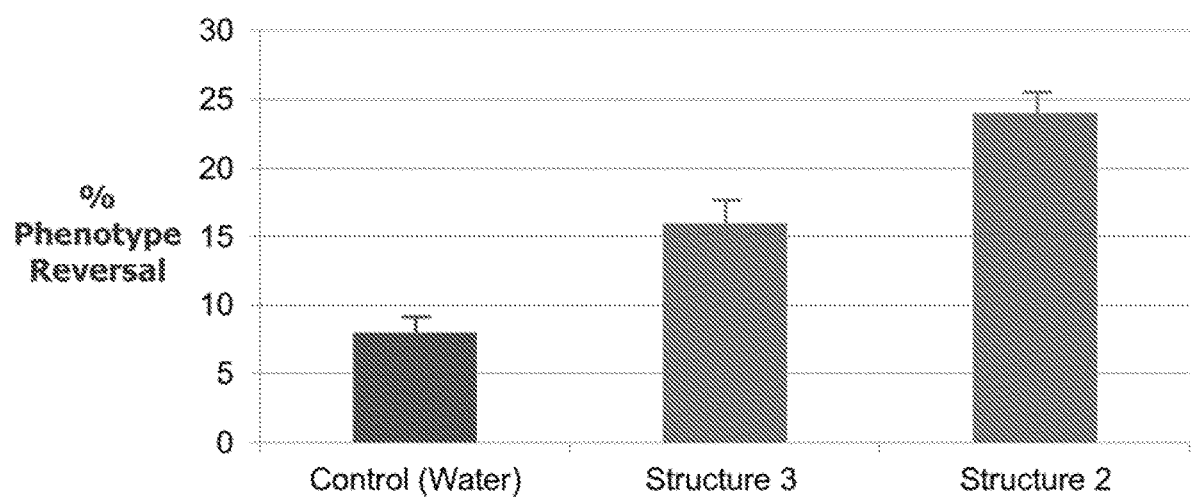
FIG. 9 shows a graph of the anti G12V phenotype activity of Structure 2 and Structure 3 in flies.

Wings that received a score of 3 or above are considered "reversed", since their phenotype is closer to WT than to kRAS G12V bearing *Drosophila*. The findings are plotted in FIG. 9. Structures 2 and 3 treatments led to a phenotype reversal % of 24% and 16%, respectively, compared to 8% for control. The difference for mean scores between the treated and control group was significantly different by Tukey's honest significance difference test ($p<001$).

Pharmacokinetic Study in Mice

Pharmacokinetic studies were carried out using 10 weeks old CD-1 mice. Structure 2 and Structure 3 were injected ip, 3 mg/kg and 10 mg/kg, respectively, at 8 time points (0, 0.25, 0.5, 1, 2, 4, 8 and 24 hours post-dose). Blood was collected from 3 animals/time point and concentrations of Structure 2 in plasma determined using LC/MS. The results are provided in Table 4 below.

TABLE 4

Pharmacokinetic Profile C06 in Mice

| | | Value | |
|---|---|---|---|
| Parameter Estimate (PE) | Units | Structure 2 | Structure 3 |
| $R_{sq}$ for Pharmacokinetic Fit | Dimensionless | 0.99 | 0.97 |
| Concentration$_{max}$ | Microgram/mL | 5.74 | 3.38 |

TABLE 4-continued

Pharmacokinetic Profile C06 in Mice

| Parameter Estimate (PE) | Units | Value Structure 2 | Structure 3 |
|---|---|---|---|
| $Time_{last}$ | Hour | 8.00 | 4.00 |
| $Concentration_{last}$ | Microgram/mL | 0.11 | 0.15 |
| $AUC_{last}$ | (Microgram * Hour)/mL | 10.71 | 3.92 |
| Lambda_z | $Hour^{-1}$ | 0.53 | 0.76 |
| $t_{1/2}$_Lambda_z | Hour | 1.32 | 0.91 |
| $AUC_{INF}$ | (Microgram * Hour)/mL | 10.92 | 4.12 |
| AUC_%Extrap | % | 1.92 | 4.92 |
| Vz/F | mL/kg | 532.24 | 3191.64 |
| Cl/F | mL/Minute/kg | 4.58 | 4.04 |
| $MRT_{last}$ | Hour | 2.00 | 1.03 |
| $MRT_{INF}$ | Hour | 2.15 | 1.25 |

Structure 2 and Structure 3 both appear intact in plasma post an ip dose but are also cleared relatively rapidly (Cl/F=4.58 and 4.04 ml/minute/kg, respectively), but at a rate less than the typical maximum possible clearance which is liver blood flow, 90 ml/minute/hour in mice. Consistent with the relatively rapid clearance, the elimination half-lives and mean resident times (MRT) appears to be approximately one to two hours. Structure 2 appears to distribute widely which is also consistent with the relatively rapid clearance, eg, the observed apparent volume of distribution during the terminal elimination phase (Vz/F) of 532 ml/kg approximates estimated total body water in the mouse, 725 ml/kg (Davies B, Morris T, Physiological parameters in laboratory animals and humans. Pharm Res. 1993; 10:1093-5). Structure 3 appears to distribute even more widely (Vz/F of over 3 liters/kg)

Safety Study in Mice

The multi-day safety study used female, 10 week old, CD1 mice (4/treatment group) dosed with DMSO. Mice were administered 2 mg/kg of Structure 2 or 10 mg/kg Structure 3, ip, daily for 6 days and evaluated for changes clinical chemistry values, hematology values and animal weight as well as signs of health and grooming habits.

Heparinized blood samples were obtained by retro-orbital puncture on Day 6, 12 hours after the last dose of Structure 2. The plasma harvested from the blood was analyzed for standard clinical chemistry parameters (ALB. ALP, ALT, AMY, TBIL, BUN, CA, PHOS, CRE GLU, NA, K, TP & GLOB) and hematology (WBC, LYM, MON, GRA, RBC, HGB, HCT, MCV, MCH, MCHC, RDWc, PLT, PCT, MPV, PDWc) analytes (see definitions herein). Animal weight changes were also monitored. Values for all analytes were analyzed by one way ANOVA plus post-hoc Bonferroni using SPSS (IBM, Armonk, NY).

Clinic chemistry results for Structure 2 and Structure 3 dosed ip in mice for six days are provided in the Table 5 below. The dosing vehicle was DMSO.

TABLE 5

Clinical chemistry values post 6 day treatment with 2 mg/kg Structure 2 or 10 mg/kg Structure 3, or treatment the respective dosing vehicles for each study.

| Treatment | Structure 2 | Vehicle Control (Structure 2) | 3 Structure | Vehicle Control (Structure 3) |
|---|---|---|---|---|
| ALB (g/dl) | 3.88 ± 0.30 | 3.78 ± 0.30 | 4.0 ± 0.10 | 3.90 ± 0.10 |
| ALP (U/L) | 66.50 ± 8.80 | 76.00 ± 12.60 | 106.3 ± 21.40 | 129.00 ± 14.7 |
| ALT (U/L) | 59.00 ± 32.50 | 59.75 ± 33.50 | 77.3 ± 16.30 | 42.80 ± 6.80 |
| AMY (U/L) | 871.50 ± 74.70 | 1061.25 ± 187.00 | 932.0 ± 98.90 | 991.80 ± 162.30 |
| TBIL (mg/dl) | 0.43 ± 0.00 | 0.40 ± 0.00 | 0.4 ± 0.00 | 0.40 ± 0.00 |
| BUN (mg/dl) | 18.25 ± 4.10 | 20.25 ± 5.30 | 22.0 ± 5.40 | 23.80 ± 5.40 |
| $Ca^{++}$ (mg/dl) | 9.43 ± 0.40 | 9.60 ± 0.10 | 9.7 ± 0.10 | 9.60 ± 0.20 |
| PHOS (mg/dl) | 8.13 ± 1.00 | 8.98 ± 1.20 | 9.8 ± 0.40 | 8.80 ± 1.10 |
| CRE (mg/dl) | 0.34 ± 0.10 | 0.45 ± 0.20 | <0.40 | <0.60 |
| GLU (mg/dl) | 234.25 ± 31.70 | 229.00 ± 34.70 | 309.0 ± 45.10 | 278.50 ± 66.80 |
| $NA^+$ (mmol/L) | 147.00 ± 0.80 | 148.50 ± 2.60 | 147.8 ± 2.20 | 146.80 ± 2.60 |
| $K^+$ (mmol/L) | 5.35 ± 0.40 | 6.25 ± 1.20 | 4.6 ± 0.20 | 4.60 ± 0.50 |
| TP (g/dl) | 5.08 ± 0.20 | 5.13 ± 0.40 | 5.2 ± 0.20 | 5.40 ± 0.20 |
| GLOB (g/dl) | 1.23 ± 0.10 | 1.33 ± 0.20 | 1.2 ± 0.10 | 1.40 ± 0.10 |

With respect to clinical chemistry results, both Structure 2 and Structure 3 appear safe, ie, no significant clinical chemistry changes were observed between Structure 2- or Structure 3 dosed animals and their respected dosing vehicles treated animals. Hematology results for Structure 2 and Structure 3 dosed ip in mice for six days are provided in the following Table 6.

TABLE 6

Hematology values post 6 day treatment with 2 mg/kg Structure 2 or 10 mg/kg Structure 3, or treatment the respective dosing vehicles for each study.

| Treatment | Structure 2 | Vehicle Control (Structure 2) | Structure 3 | Vehicle Control (Structure 3) |
|---|---|---|---|---|
| WBC ($10^9$/l) | 6.72 ± 2.00 | 7.94 ± 1.80 | 5.2 ± 1.80 | 5.2 ± 0.70 |
| LYM ($10^9$/l) | 5.17 ± 1.80 | 5.96 ± 2.50 | 4.6 ± 1.40 | 4.4 ± 0.40 |

TABLE 6-continued

Hematology values post 6 day treatment with 2 mg/kg Structure 2 or 10 mg/kg Structure 3, or treatment the respective dosing vehicles for each study.

| Treatment | Structure 2 | Vehicle Control (Structure 2) | Structure 3 | Vehicle Control (Structure 3) |
|---|---|---|---|---|
| MON (10^9/l) | 0.33 ± 0.10 | 0.46 ± 0.20 | 0.2 ± 0.20 | 0.1 ± 0.10 |
| GRA (10^9/l) | 1.23 ± 0.20 | 1.53 ± 0.90 | 0.4 ± 0.20 | 0.7 ± 0.30 |
| LYM (%) | 76.18 ± 3.50 | 72.95 ± 14.30 | 90.0 ± 4.30 | 84.1 ± 4.50 |
| MON (%) | 4.85 ± 0.40 | 5.68 ± 2.10 | 3.1 ± 2.00 | 2.5 ± 1.70 |
| GRA (%) | 19.03 ± 3.70 | 21.33 ± 14.00 | 7.0 ± 3.00 | 13.5 ± 3.70 |
| RBC (10^12/l) | 9.44 ± 1.00 | 9.11 ± 0.40 | 8.8 ± 0.50 | 9.6 ± 0.80 |
| HGB (g/dl) | 15.23 ± 1.70 | 15.00 ± 1.20 | 14.1 ± 0.50 | 14.8 ± 1.70 |
| HCT (%) | 44.34 ± 4.60 | 44.70 ± 1.50 | 43.1 ± 1.80 | 44.6 ± 3.20 |
| MCV (fl) | 47.00 ± 2.40 | 49.25 ± 1.50 | 49.3 ± 4.30 | 46.3 ± 1.30 |
| MCH (pg) | 16.15 ± 0.40 | 16.40 ± 0.60 | 16.0 ± 0.70 | 15.5 ± 0.60 |
| MCHC (g/dl) | 34.35 ± 1.30 | 33.45 ± 2.20 | 32.7 ± 2.50 | 33.2 ± 1.60 |
| RDWc (%) | 17.40 ± 0.40 | 16.48 ± 0.50 | 17.4 ± 0.70 | 17.4 ± 0.60 |
| PLT (10^9/l) | 448.50 ± 193.10 | 452.25 ± 165.80 | 578.8 ± 86.70 | 357.0 ± 153.70 |
| PCT (%) | 0.31 ± 0.10 | 0.35 ± 0.10 | 0.4 ± 0.10 | 0.2 ± 0.10 |
| MPV (fl) | 7.10 ± 0.60 | 7.78 ± 1.00 | 6.7 ± 0.40 | 6.5 ± 0.50 |
| PDWc (%) | 33.08 ± 3.40 | 34.38 ± 1.00 | 30.0 ± 1.50 | 29.3 ± 1.80 |

With respect to clinical chemistry results, both Structure 2 and Structure 3 appear safe, ie, no significant clinical chemistry changes were observed between Structure 2- or Structure 3 dosed animals and their respected dosing vehicles treated animals. Finally, no statistically significant difference was noted in body weight or grooming habits between Structure 2- and Structure 3 dosed animals and their respected dosing vehicles treated animals.

Xenograft Study

Female nude mice (nu/nu) were purchased from Simonsen Laboratories (Gilroy, CA). All experiments were performed with 4 to 6-week-old female mice. Mice were housed in a barrier unit in the Tosk Animal facility, kept in filter-top cages with water and food provided ad libitum, and were checked at least twice a week for clinical signs of disease and discomfort.

Subcutaneous tumors are induced by subcutaneous inoculation in the right flank of $3 \times 10^6$ human colon cancer cell line SW480 in Matrigel. The tumors are allowed to grow and volumes (mm$^3$) are calculated weekly from digital caliper measurements as 0.5× length×width$^2$. Treatment was initiated 6 days post tumor implantation. Structure 2 was administrated ip at 2 mg/kg, while control was given vehicle DMSO. All the animals were sacrificed at day 30.

Figure 10:
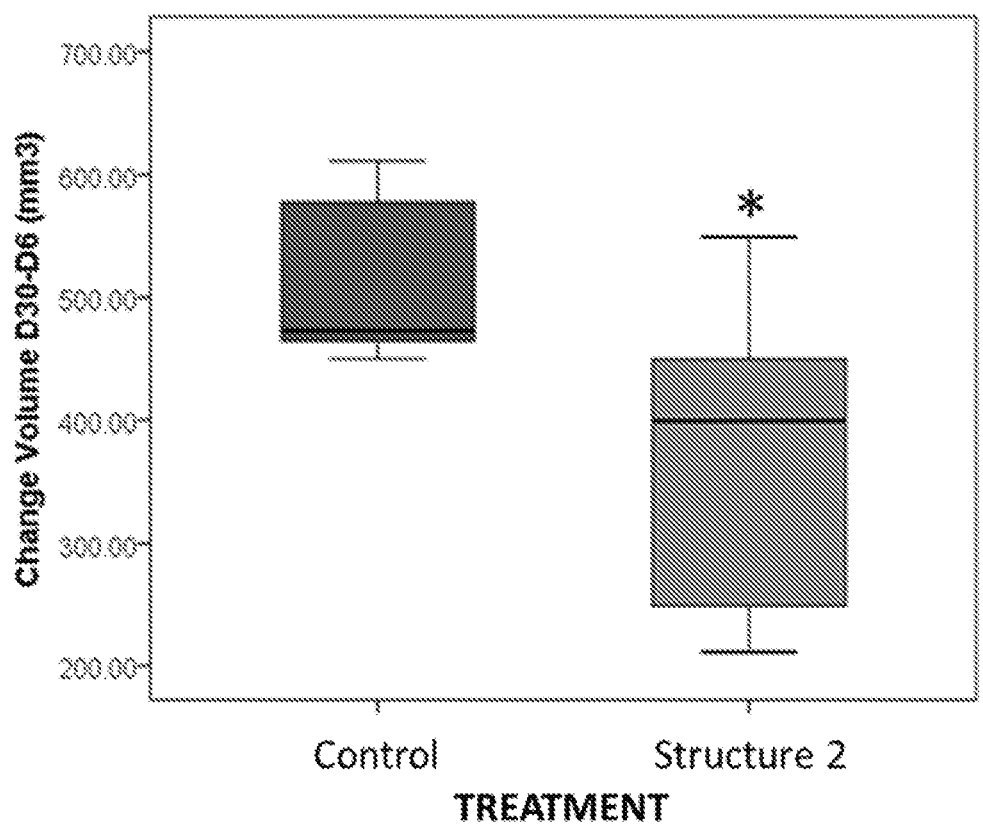
FIG. 10 Effect of Structure 2 on growth of SW480 cells implanted into nu/nu mice. Boxplots showing tumor volumes in nude mice 24 days post treatment ip with either 2 mg/kg Structure 2 or vehicle control (DMSO). Subcutaneous tumors were induced by subcutaneous inoculation in the right flank of 3×10$^6$ human colon cancer cell line SW480 in Matrigel. Treatment with Structure 2 was initiated 6 days post tumor implantation. Structure 2 was administrated ip at 2 mg/kg, while control was given vehicle DMSO. All animals were sacrificed at day 30. Structure 2 provided a statistically significant reduction in tumor volume compared to vehicle control shows the effect of an exemplary compound on growth of SW480 cells implanted into nu/nu mice. In the Figure, (*) designates p<0.028 compared to vehicle control by Student's t-test.

The findings provided in FIG. 10 demonstrate that Structure 2 mitigates the growth of SW480 cells implanted into nu/nu mice. The result was statistically significant (*p<0.028 by Student's t-test for tumor size in Structure 2 treated mice versus vehicle control treated mice).

Notwithstanding the appended claims, the disclosure is also defined by the following clauses:

1. A RAS modulating compound of the formula:

$$Cy_1-Cy_2-L-Cy_3$$

wherein:

$Cy_1$, $Cy_2$ and $Cy_3$ are cyclic groups independently selected from a substituted or unsubstituted cycloalkyl, a substituted or unsubstituted aryl, a substituted or unsubstituted heteroaryl, a substituted or unsubstituted cycloheteroalkyl, a substituted or unsubstituted bicycloalkenyl, a substituted or unsubstituted bicycloheteroalkenyl, a substituted or unsubstituted bicycloaryl and a substituted or unsubstituted bicycloheteroaryl, wherein $Cy_1$ is optional; and L is a linker group;

or a salt thereof, or a solvate, hydrate or prodrug form thereof.

2. The compound according to clause 1, wherein the compound has the formula:

$$Cy_1-Cy_2-(CR^1R^2)_n-Y^1-(CR^1R^2)_m-Cy_3$$

wherein:

$Cy_1$ is an optional cyclic group selected from an oxadiazole and a thiadiazole;

$Cy_2$ is a phenyl;

$Cy_3$ is a pyrazole, wherein $Cy_1$, $Cy_2$ and $Cy_3$ are optionally further substituted;

n and m are each independently 0, 1, 2, 3, 4, 5 or 6, wherein n+m is less than 7;

each $R^1$ and each $R^2$ is independently H, an alkyl or a substituted alkyl; and $Y^1$ is selected from —CONR—, —NRCO—, —NRSO$_2$— and —SO$_2$NR— wherein R is H, an alkyl or a substituted alkyl.

3. The compound according to clause 2, wherein the compound is of Formula A:

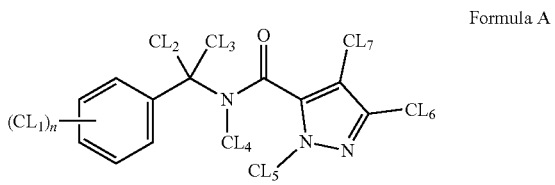

Formula A wherein:

each $CL_1$, $CL_6$ and $CL_7$ are each independently selected from hydrogen, halogen, —CN, —NO$_2$, —OH, —OR$_a$, —C(O)R$_a$, —CO$_2$R$_a$, —O(CO)R$_a$, —C(O)NR$_a$R$_b$, —OC(O)NR$_a$R$_b$, —SR$_a$, —SOR$_a$, —SO$_2$R$_a$, —SO$_2$NR$_a$R$_b$, —NR$_a$R$_b$, —NR$_a$C(O)R$_b$, —NR$_a$C(O)$_2$R$_b$, —NR$_a$SO$_2$R$_b$, —NR$_a$(CO)NR$_b$R$_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein R$_a$, R$_b$ and R$_c$ are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of $R_a$, $R_b$ together or $R_a$ and R, together with the atom(s) to which they are attached, may form an unsubstituted or substituted 5-, 6- or 7-membered ring; n is 0, 1, 2, 3, 4 or 5; and $CL_2$, $CL_3$, $CL_4$ and $CL_5$ are each independently selected from hydrogen, alkyl and substituted alkyl (e.g., selected from hydrogen, methyl, ethyl, propyl, isopropyl, butyl, tert-butyl, sec-butyl, pentyl, neopentyl, isopentyl, hexyl and isohexyl).

4. The compound according to clause 2, wherein the compound is of Formula B:

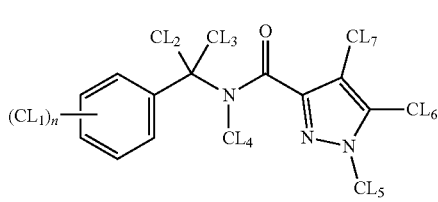

Formula B wherein:

each $CL_1$, $CL_6$ and $CL_7$ are each independently selected from hydrogen, halogen, —CN, —$NO_2$, —OH, —$OR_a$, —C(O)$R_a$, —$CO_2R_a$, —O(CO)$R_a$, —C(O)$NR_aR_b$, —OC(O)$NR_aR_b$, —$SR_a$, —$SOR_a$, —$SO_2R_a$, —$SO_2NR_aR_b$, —$NR_aR_b$, —$NR_aC(O)R_b$, —$NR_aC(O)_2R_b$, —$NR_aSO_2R_b$, —$NR_a(CO)NR_bR_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein $R_a$, $R_b$ and R, are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of $R_a$, $R_b$ together or $R_a$ and R, together with the atom(s) to which they are attached, may form an unsubstituted or substituted 5-, 6- or 7-membered ring; n is 0, 1, 2, 3, 4 or 5; and $CL_2$, $CL_3$, $CL_4$ and $CL_5$ are each independently selected from hydrogen, alkyl and substituted alkyl (e.g., selected from hydrogen, methyl, ethyl, propyl, isopropyl, butyl, tert-butyl, sec-butyl, pentyl, neopentyl, isopentyl, hexyl and isohexyl).

5. The compound according to clause 2, wherein the compound has a structure corresponding to Formula C:

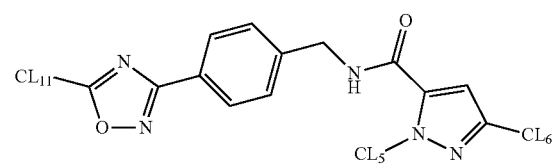

Formula C wherein:

$CL_{11}$ is selected from hydrogen, halogen, —CN, —$NO_2$, —OH, —$OR_a$, —C(O)$R_a$, —$CO_2R_a$, —O(CO)$R_a$, —C(O)$NR_aR_b$, —OC(O)$NR_aR_b$, —$SR_a$, —$SOR_a$, —$SO_2R_a$, —$SO_2NR_aR_b$, —$NR_aR_b$, —$NR_aC(O)R_b$, —$NR_aC(O)_2R_b$, —$NR_aSO_2R_b$, —$NR_a(CO)NR_bR_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein $R_a$, $R_b$ and R, are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of $R_a$, $R_b$ together or $R_a$ and R, together with the atom(s) to which they are attached, may form an unsubstituted or substituted 5-, 6- or 7-membered ring.

6. The compound according to clause 4, wherein the compound is of Formula D:

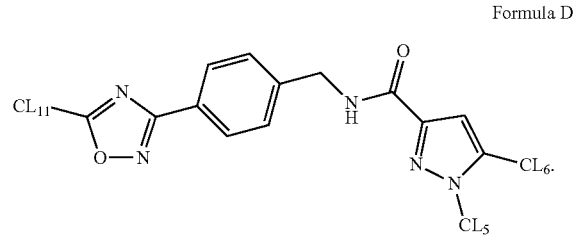

Formula D

7. The compound according to clause 5, wherein the compound has the following structure:

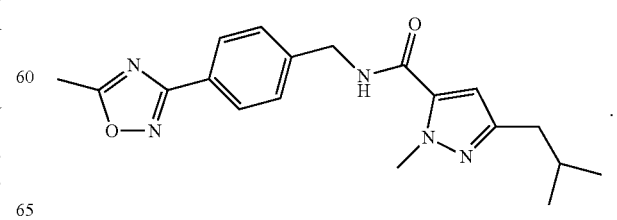

8. The compound according to clause 5, wherein the compound has the following structure:

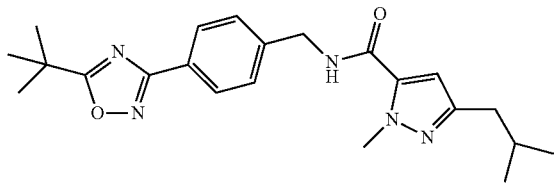

9. The compound according to clause 1, wherein the compound is of Formula G:

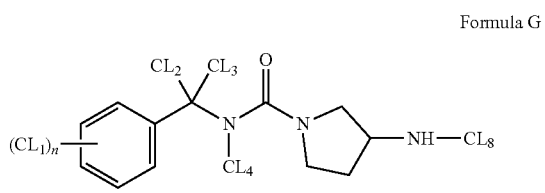

Formula G wherein:

CL$_1$ is selected from hydrogen, halogen, —CN, —NO$_2$, —OH, —OR$_a$, —C(O)R$_a$, —CO$_2$R$_a$, —O(CO)R$_a$, —C(O)NR$_a$R$_b$, —OC(O)NR$_a$R$_b$, —SR$_a$, —SOR$_a$, —SO$_2$R$_a$, —SO$_2$NR$_a$R$_b$, —NR$_a$R$_b$, —NR$_a$C(O)R$_b$, —NR$_a$C(O)$_2$R$_b$, —NR$_a$SO$_2$R$_b$, —NR$_a$(CO)NR$_b$R$_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein R$_a$, R$_b$ and R$_c$ are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of R$_a$, R$_b$ together or R$_a$ and R$_c$ together with the atom(s) to which they are attached, may form an unsubstituted or substituted 5-, 6- or 7-membered ring;

n is 0, 1, 2, 3, 4 or 5;

CL$_2$, CL$_3$ and CL$_4$ are each independently selected from hydrogen, methyl, ethyl, propyl, isopropyl, butyl, tert-butyl, sec-butyl, pentyl, neopentyl, isopentyl, hexyl and isohexyl; and CL$_8$ is selected from hydrogen, acetyl, propionyl and butyryl.

10. The compound according to clause 9, wherein the compound is of Formula H:

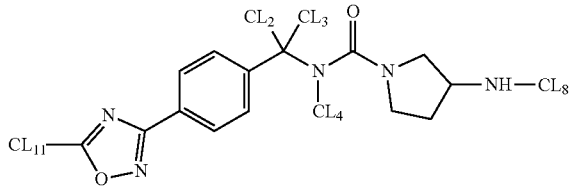

Formula H wherein:

CL$_{11}$ is selected from hydrogen, halogen, —CN, —NO$_2$, —OH, —OR$_a$, —C(O)R$_a$, —CO$_2$R$_a$, —O(CO)R$_a$, —C(O)NR$_a$R$_b$, —OC(O)NR$_a$R$_b$, —SR$_a$, —SOR$_a$, —SO$_2$R$_a$, —SO$_2$NR$_a$R$_b$, —NR$_a$R$_b$, —NR$_a$C(O)R$_b$, —NR$_a$C(O)$_2$R$_b$, —NR$_a$SO$_2$R$_b$, —NR$_a$(CO)NR$_b$R$_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein R$_a$, R$_b$ and R$_c$ are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of R$_a$, R$_b$ together or R$_a$ and R$_c$ together with the atom(s) to which they are attached, may form an unsubstituted or substituted 5-, 6- or 7-membered ring.

11. The compound according to clause 1, wherein the compound has the formula:

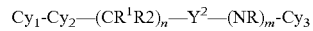

Cy$_1$-Cy$_2$—(CR$^1$R2)$_n$—Y$^2$—(NR)$_m$-Cy$_3$ wherein:

Cy$_1$ is selected from phenyl and a 4, 5 or 6-membered heterocycle (e.g., heteroaryl) comprising one or more heteroatoms in the ring independently selected from O, N and S and at least one carbon atom;

Cy$_2$ is selected from a pyrazole, a pyrrole, a 1,2,3-triazole and an imidazole;

Cy$_3$ is a pyridinyl, a pyrimidinyl, a triazinyl, a quinazolinyl, a pyrido-pyrimidinyl, a pyrido-pyridazinyl, a pyrrolo-pyrimidinyl, a pyrazolo-pyrimidinyl or a purine, wherein Cy$_1$, Cy$_2$ and Cy$_3$ are optionally further substituted;

n is 0, 1, 2, 3, 4, 5 or 6, and m is 0 or 1;

each R$^1$, each R$^2$ and R is independently H, an alkyl or a substituted alkyl; and Y$^2$ is a cycloalkyl or a heterocycle.

12. The compound of clause 11, wherein the compound is of Formula 1:

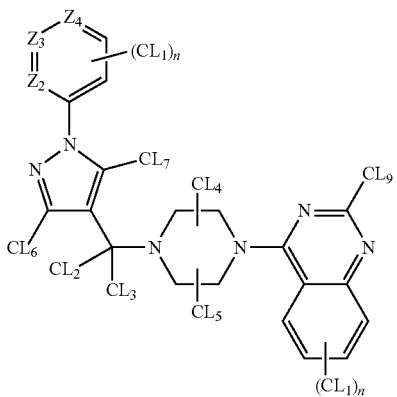

Formula I wherein:
Z$_2$, Z$_3$ and Z$_4$ are each independently CH or N (e.g., at least two of Z$_2$, Z$_3$ and Z$_4$ are CH);
each CL$_1$, CL$_6$, CL$_7$ and CL$_9$ are each independently selected from hydrogen, halogen, —CN, —NO$_2$, —OH, —OR$_a$, —C(O)R$_a$, —CO$_2$R$_a$, —O(CO)R$_a$, —C(O)NR$_a$R$_b$, —OC(O)NR$_a$R$_b$, —SR$_a$, —SOR$_a$, —SO$_2$R$_a$, —SO$_2$NR$_a$R$_b$, —NR$_a$R$_b$, —NR$_a$C(O)R$_b$, —NR$_a$C(O)$_2$R$_b$, —NR$_a$SO$_2$R$_b$, —NR$_a$(CO)NR$_b$R$_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein R$_a$, R$_b$ and R$_c$ are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of R$_a$, R$_b$ together or R$_a$ and R$_c$ together with the atom(s) to which they are attached, may form an unsubstituted or substituted 5-, 6- or 7-membered ring;
each n is independently 0, 1, 2, 3, 4 or 5; and
CL$_2$, CL$_3$, CL$_4$ and CL$_5$ are each independently selected from hydrogen, methyl, ethyl, propyl, isopropyl, butyl, tert-butyl, sec-butyl, pentyl, neopentyl, isopentyl, hexyl and isohexyl.

13. The compound according to clause 12, wherein the compound is of Formula J:

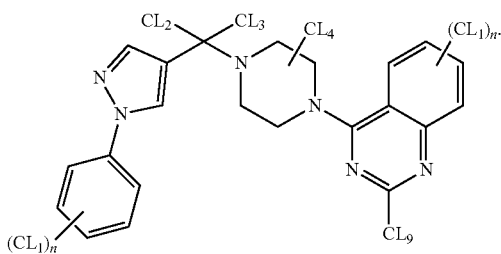

Formula J

14. The compound according to clause 13, wherein the compound has the following structure:

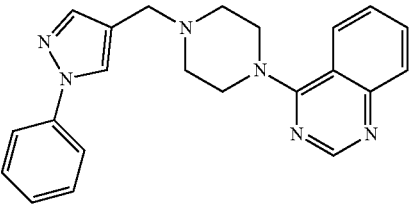

15. The compound according to clause 11, wherein the compound is of Formula L:

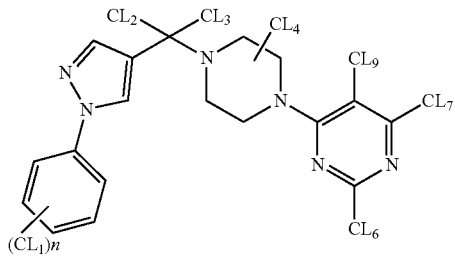

Formula L wherein:
CL$_1$, CL$_6$, CL$_7$ and CL$_9$ are each independently selected from hydrogen, halogen, —CN, —NO$_2$, —OH, —OR$_a$, —C(O)R$_a$, —CO$_2$R$_a$, —O(CO)R$_a$, —C(O)NR$_a$R$_b$, —OC(O)NR$_a$R$_b$, —SR$_a$, —SOR$_a$, —SO$_2$R$_a$, —SO$_2$NR$_a$R$_b$, —NR$_a$R$_b$, —NR$_a$C(O)R$_b$, —NR$_a$C(O)$_2$R$_b$, —NR$_a$SO$_2$R$_b$, —NR$_a$(CO)NR$_b$R$_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein R$_a$, R$_b$ and R$_c$ are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of R$_a$, R$_b$ together or R$_a$ and R, together with the atom(s) to which they are attached, may form an unsubstituted or substituted 5-, 6- or 7-membered ring;

n is 0, 1, 2, 3, 4 or 5; and

CL$_2$, CL$_3$ and CL$_4$ are each independently selected from hydrogen, methyl, ethyl, propyl, isopropyl, butyl, tert-butyl, sec-butyl, pentyl, neopentyl, isopentyl, hexyl and isohexyl.

16. The compound according to clause 11, wherein the compound is of Formula M:

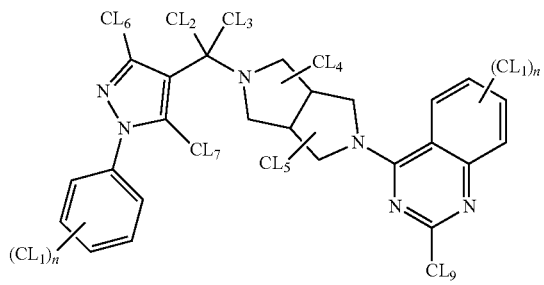

Formula M wherein:
each $CL_1$, $CL_6$, $CL_7$ and $CL_9$ are each independently selected from hydrogen, halogen, —CN, —NO$_2$, —OH, —OR$_a$, —C(O)R$_a$, —CO$_2$R$_a$, —O(CO)R$_a$, —C(O)NR$_a$R$_b$, —OC(O)NR$_a$R$_b$, —SR$_a$, —SOR$_a$, —SO$_2$R$_a$, —SO$_2$NR$_a$R$_b$, —NR$_a$R$_b$, —NR$_a$C(O)R$_b$, —NR$_a$C(O)$_2$R$_b$, —NR$_a$SO$_2$R$_b$, —NR$_a$(CO)NR$_b$R$_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein R$_a$, R$_b$ and R$_c$ are each independently selected from hydrogen, unsubstituted or substituted C1-6 haloalkyl, unsubstituted or substituted C1-6 alkyl, unsubstituted or substituted O3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of R$_a$, R together or R$_a$ and R$_c$ together with the atom(s) to which they are attached, may form an unsubstituted or substituted 5-, 6- or 7-membered ring;
each n is independently 0,1, 2, 3, 4 or 5; and
$CL_2$, $CL_3$, $CL_4$ and $CL_5$ are each selected from hydrogen, methyl, ethyl, propyl, isopropyl, butyl, tert-butyl, sec-butyl, pentyl, neopentyl, isopentyl, hexyl and isohexyl.

17. The compound according to clause 11, wherein the compound is of Formula N:

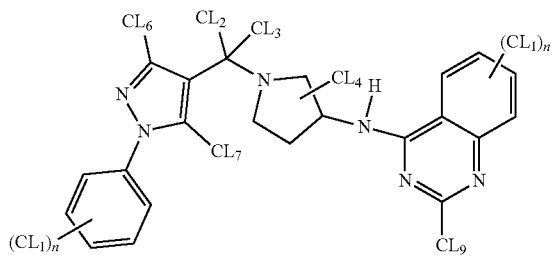

Formula N wherein:
each $CL_1$, $CL_6$, $CL_7$ and $CL_9$ are each independently selected from hydrogen, halogen, —CN, —NO$_2$, —OH, —OR$_a$, —C(O)R$_a$, —CO$_2$R$_a$, —O(CO)R$_a$, —C(O)NR$_a$R$_b$, —OC(O)NR$_a$R$_b$, —SR$_a$, —SOR$_a$, —SO$_2$R$_a$, —SO$_2$NR$_a$R$_b$, —NR$_a$R$_b$, —NR$_a$C(O)R$_b$, —NR$_a$C(O)$_2$R$_b$, —NR$_a$SO$_2$R$_b$, —NR$_a$(CO)NR$_b$R$_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein R$_a$, R$_b$ and R$_c$ are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of R$_a$, R$_b$ together or R$_a$ and R$_c$ together with the atom(s) to which they are attached, may form an unsubstituted or substituted 5-, 6- or 7-membered ring;
each n is independently 0, 1, 2, 3, 4 or 5; and
$CL_2$, $CL_3$ and $CL_4$ are each independently selected from hydrogen, methyl, ethyl, propyl, isopropyl, butyl, tert-butyl, sec-butyl, pentyl, neopentyl, isopentyl, hexyl and isohexyl.

18. The compound according to clause 11, wherein the compound is of Formula O:

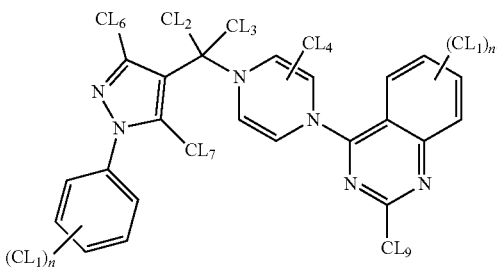

Formula O wherein:
each $CL_1$, $CL_6$, $CL_7$ and $CL_9$ are each independently selected from hydrogen, halogen, —CN, —NO$_2$, —OH, —OR$_a$, —C(O)R$_a$, —CO$_2$R$_a$, —O(CO)R$_a$, —C(O)NR$_a$R$_b$, —OC(O)NR$_a$R$_b$, —SR$_a$, —SOR$_a$, —SO$_2$R$_a$, —SO$_2$NR$_a$R$_b$, —NR$_a$R$_b$, —NR$_a$C(O)R$_b$, —NR$_a$C(O)$_2$R$_b$, —NR$_a$SO$_2$R$_b$, —NR$_a$(CO)NR$_b$R$_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein R$_a$, R$_b$ and R$_c$ are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of $R_a$, $R_b$ together or $R_a$ and $R_c$ together with the atom(s) to which they are attached, may form an unsubstituted or substituted 5-, 6- or 7-membered ring;

each n is independently 0, 1, 2, 3, 4 or 5; and $CL_2$, $CL_3$ and $CL_4$ are each independently selected from hydrogen, methyl, ethyl, propyl, isopropyl, butyl, tert-butyl, sec-butyl, pentyl, neopentyl, isopentyl, hexyl and isohexyl.

19. The compound according to clause 11, wherein the compound is of Formula P:

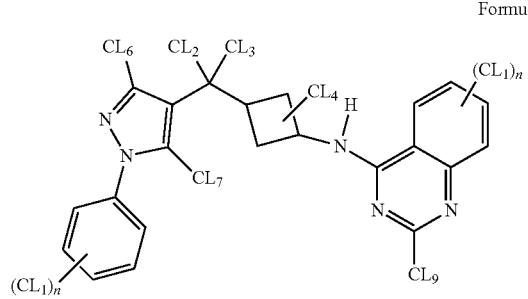

Formula P wherein:

each $CL_1$, $CL_6$, $CL_7$ and $CL_9$ are each independently selected from hydrogen, halogen, —CN, —NO$_2$, —OH, —OR$_a$, —C(O)R$_a$, —CO$_2$R$_a$, —O(CO)R$_a$, —C(O)NR$_a$R$_b$, —OC(O)NR$_a$R$_b$, —SR$_a$, —SOR$_a$, —SO$_2$R$_a$, —SO$_2$NR$_a$R$_b$, —NR$_a$R$_b$, —NR$_a$C(O)R$_b$, —NR$_a$C(O)$_2$R$_b$, —NR$_a$SO$_2$R$_b$, —NR$_a$(CO)NR$_b$R$_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein $R_a$, $R_b$ and R, are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of $R_a$, $R_b$ together or $R_a$ and $R_c$ together with the atom(s) to which they are attached, may form an unsubstituted or substituted 5-, 6- or 7-membered ring;

each n is independently 0, 1, 2, 3, 4 or 5; and $CL_2$, $CL_3$ and $CL_4$ are each independently selected from hydrogen, methyl, ethyl, propyl, isopropyl, butyl, tert-butyl, sec-butyl, pentyl, neopentyl, isopentyl, hexyl and isohexyl.

20. The compound according to clause 12, wherein the compound is of Formula Q:

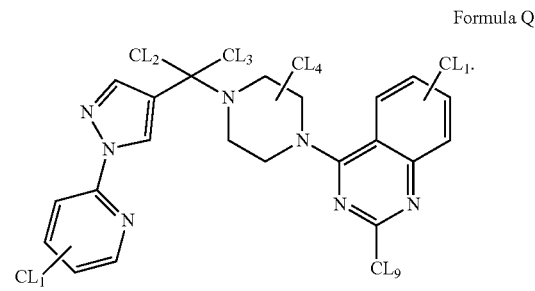

Formula Q

21. The compound according to clause 12, wherein the compound is of Formula R:

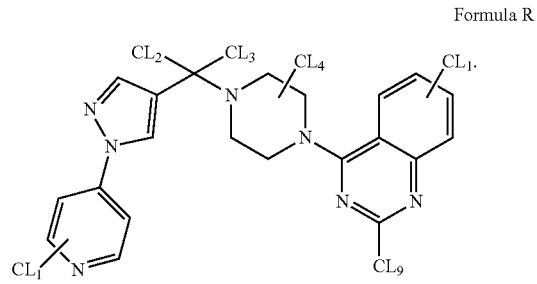

Formula R

22. The compound according to clause 12, wherein the compound is of Formula S:

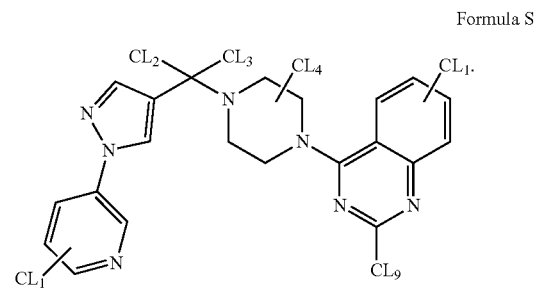

Formula S

23. The compound according to clause 11, wherein the compound is of Formula T:

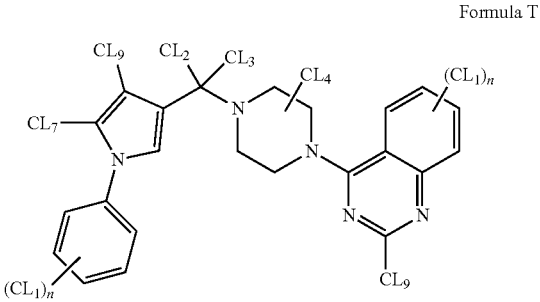

Formula T wherein:

each $CL_1$, $CL_6$, $CL_7$ and $CL_9$ are each independently selected from hydrogen, halogen, —CN, —NO$_2$, —OH, —OR$_a$, —C(O)R$_a$, —CO$_2$R$_a$, —O(CO)R$_a$, —C(O)NR$_a$R$_b$, —OC(O)NR$_a$R$_b$, —SR$_a$, —SOR$_a$, —SO$_2$R$_a$, —SO$_2$NR$_a$R$_b$, —NR$_a$R$_b$, —NR$_a$C(O)R$_b$, —NR$_a$C(O)$_2$R$_b$, —NR$_a$SO$_2$R$_b$, —NR$_a$(CO)NR$_b$R$_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein R$_a$, R$_b$ and R$_c$ are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of R$_a$, R$_b$ together or R$_a$ and R$_c$ together with the atom(s) to which they are attached, may form an unsubstituted or substituted 5-, 6- or 7-membered ring;

each n is independently 0, 1, 2, 3, 4 or 5; and

CL$_2$, CL$_3$ and CL$_4$ are each independently selected from hydrogen, methyl, ethyl, propyl, isopropyl, butyl, tert-butyl, sec-butyl, pentyl, neopentyl, isopentyl, hexyl and isohexyl.

24. The compound according to clause 11, wherein the compound is of Formula U:

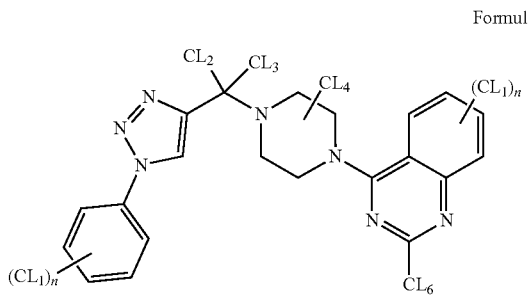

Formula U wherein:

each CL$_1$ and CL$_6$ are each independently selected from hydrogen, halogen, —CN, —NO$_2$, —OH, —OR$_a$, —C(O)R$_a$, —COO$_2$R$_a$, —O(CO)R$_a$, —C(O)NR$_a$R$_b$, —OC(O)NR$_a$R$_b$, —SR$_a$, —SOR$_a$, —SO$_2$R$_a$, —SO$_2$NR$_a$R$_b$, —NR$_a$R$_b$, —NR$_a$C(O)R$_b$, —NR$_a$C(O)$_2$R$_b$, —NR$_a$SO$_2$R$_b$, —NR$_a$(CO)NR$_b$R$_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein R$_a$, R$_b$ and R$_c$ are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of R$_a$, R$_b$ together or R$_a$ and R$_c$ together with the atom(s) to which they are attached, may form an unsubstituted or substituted 5-, 6- or 7-membered ring;

each n is independently 0, 1, 2, 3, 4 or 5; and

CL$_2$, CL$_3$ and CL$_4$ are each independently selected from hydrogen, methyl, ethyl, propyl, isopropyl, butyl, tert-butyl, sec-butyl, pentyl, neopentyl, isopentyl, hexyl and isohexyl.

25. The compound according to clause 11, wherein the compounds of Formula V:

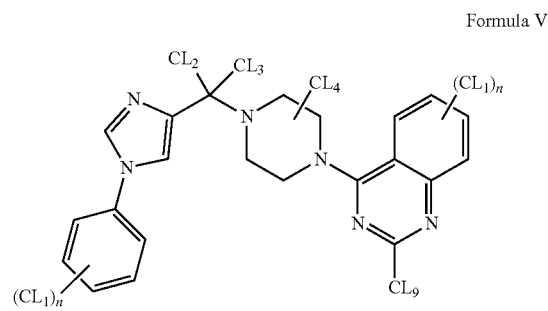

Formula V wherein:

each CL$_1$ and CL$_6$ are each independently selected from hydrogen, halogen, —CN, —NO$_2$, —OH, —OR$_a$, —C(O)R$_a$, —CO$_2$R$_a$, —O(CO)R$_a$, —C(O)NR$_a$R$_b$, —OC(O)NR$_a$R$_b$, —SR$_a$, —SOR$_a$, —SO$_2$R$_a$, —SO$_2$NR$_a$R$_b$, —NR$_a$R$_b$, —NR$_a$C(O)R$_b$, —NR$_a$C(O)$_2$R$_b$, —NR$_a$SO$_2$R$_b$, —NR$_a$(CO)NR$_b$R$_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein R$_a$, R$_b$ and R$_c$ are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of R$_a$, R$_b$ together or R$_a$ and R$_c$ together with the atom(s) to which they are attached, may form an unsubstituted or substituted 5-, 6- or 7-membered ring;

each n is independently 0, 1, 2, 3, 4 or 5; and

CL$_2$, CL$_3$ and CL$_4$ are each independently selected from hydrogen, methyl, ethyl, propyl, isopropyl, butyl, tert-butyl, sec-butyl, pentyl, neopentyl, isopentyl, hexyl and isohexyl.

26. The compound according to clause 11, wherein the compound is of Formula W:

Formula W

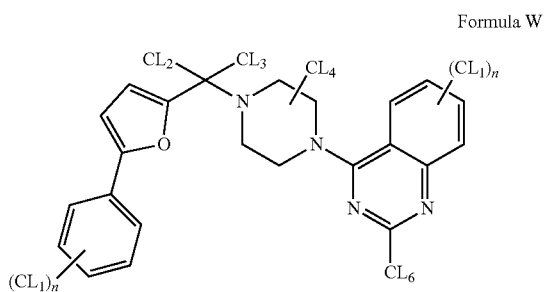

wherein:
each $CL_1$ and $CL_6$ are each independently selected from hydrogen, halogen, —CN, —NO$_2$, —OH, —OR$_a$, —C(O)R$_a$, —CO$_2$R$_a$, —O(CO)R$_a$, —C(O)NR$_a$R$_b$, —OC(O)NR$_a$R$_b$, —SR$_a$, —SOR$_a$, —SO$_2$R$_a$, —SO$_2$NR$_a$R$_b$, —NR$_a$R$_b$, —NR$_a$C(O)R$_b$, —NR$_a$C(O)$_2$R$_b$, —NR$_a$SO$_2$R$_b$, —NR$_a$(CO)NR$_b$R$_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein R$_a$, R$_b$ and R$_c$ are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of R$_a$, R$_b$ together or R$_a$ and R$_c$ together with the atom(s) to which they are attached, may form an unsubstituted or substituted 5-, 6- or 7-membered ring;
each n is independently 0, 1, 2, 3, 4 or 5; and
$CL_2$, $CL_3$ and $CL_4$ are each independently selected from hydrogen, methyl, ethyl, propyl, isopropyl, butyl, tert-butyl, sec-butyl, pentyl, neopentyl, isopentyl, hexyl and isohexyl.

27. The compound according to clause 11, wherein the compound is of Formula X:

Formula X

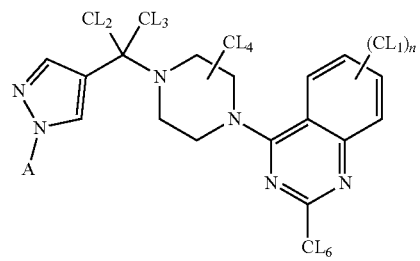

wherein:
A is a 4, 5 or 6 membered heterocycle comprising one or more heteroatoms independently selected from O, N or S and at least one carbon atom, optionally substituted with one or more $CL_1$ groups;

each $CL_1$ and $CL_6$ are each independently selected from hydrogen, halogen, —CN, —NO$_2$, —OH, —OR$_a$, —C(O)R$_a$, —CO$_2$R$_a$, —O(CO)R$_a$, —C(O)NR$_a$R$_b$, —OC(O)NR$_a$R$_b$, —SR$_a$, —SOR$_a$, —SO$_2$R$_a$, —SO$_2$NR$_a$R$_b$, —NR$_a$R$_b$, —NR$_a$C(O)R$_b$, —NR$_a$C(O)$_2$R$_b$, —NR$_a$SO$_2$R$_b$, —NR$_a$(CO)NR$_b$R$_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein R$_a$, R$_b$ and R$_c$ are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of R$_a$, R$_b$ together or R$_a$ and R$_c$ together with the atom(s) to which they are attached, may form an unsubstituted or substituted 5-, 6- or 7-membered ring;
n is 0, 1, 2, 3 or 4; and
$CL_2$, $CL_3$ and $CL_4$ are each independently selected from hydrogen, methyl, ethyl, propyl, isopropyl, butyl, tert-butyl, sec-butyl, pentyl, neopentyl, isopentyl, hexyl and isohexyl.

28. The compound according to clause 11, wherein the compound is of Formula Y or Formula Z:

Formula Y

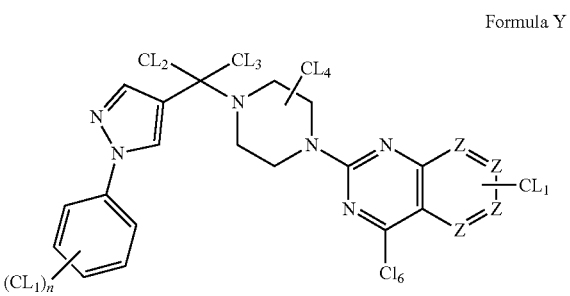

Formula Z

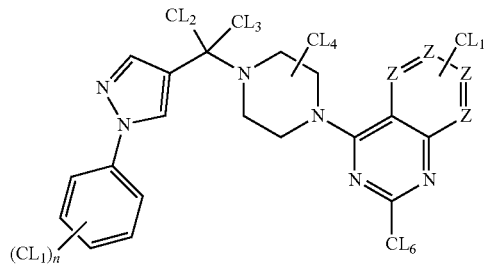

wherein:
each Z is independently nitrogen or carbon, wherein one or two of Z is nitrogen;
each $CL_1$ and $CL_6$ are each independently selected from hydrogen, halogen, —CN, —NO$_2$, —OH, —OR$_a$, —C(O)R$_a$, —CO$_2$R$_a$, —O(CO)R$_a$, —C(O)NR$_a$R$_b$, —OC(O)NR$_a$R$_b$, —SR$_a$, —SOR$_a$, —SO$_2$R$_a$, —SO$_2$NR$_a$R$_b$, —NR$_a$R$_b$, —NR$_a$C(O)R$_b$, —NR$_a$C(O)$_2$R$_b$, —NR$_a$SO$_2$R$_b$, —NR$_a$(CO)NR$_b$R$_c$, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, and unsubstituted or substituted 3- to 10-membered heterocyclyl; wherein R$_a$, R$_b$ and R$_c$ are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, unsubstituted or substituted aryl-C1-4 alkyl, and unsubstituted or substituted aryloxy-C1-4 alkyl; or two of R$_a$, R$_b$ together or R$_a$ and R$_c$ together with the atom(s) to which they are attached, may form an unsubstituted or substituted 5-, 6- or 7-membered ring;

n is 0, 1, 2, 3, 4 or 5; and

CL$_2$, CL$_3$ and CL$_4$ are each independently selected from hydrogen, methyl, ethyl, propyl, isopropyl, butyl, tert-butyl, sec-butyl, pentyl, neopentyl, isopentyl, hexyl and isohexyl.

29. A method of modulating the activity of a target RAS in a sample, the method comprising: contacting a sample comprising a target RAS with an effective amount of a compound of one of clauses 1 to 28 to modulate the activity of the target RAS.

30. The method according to clause 29, wherein the sample is a cellular sample.

31. The method according to any one of clauses 29-30, wherein the sample is in vitro.

32. The method according to clause 30, wherein the sample is in vivo.

33. The method according to any one of clauses 29-32, wherein the target RAS is a mutant kRAS, a mutant nRAS or a mutant hRAS.

34. The method according to any one of clauses 29-33, wherein the compound inhibits synthetic lethal targets downstream of RAS.

35. A method of treating a subject for a RAS driven disease, the method comprising administering to the subject a therapeutically effective amount of a compound of one of clauses 1 to 28.

36. The method according to clause 35, wherein the RAS driven disease is cancer.

37. The method according to clause 36, wherein the cancer is a kRAS dependent cancer.

38. The method according to clause 37, wherein the cancer is selected from pancreatic cancer, colon cancer, endometrial cancer, lung cancer, skin cancer, acute myeloid leukemia (AML) and multiple myeloma.

39. The method according to any one of clauses 35-38, further comprising obtaining a sample from the subject and determining whether the sample comprises a mutant RAS.

40. The method according to clause 39, wherein the mutant RAS is a mutant kRAS.

41. The method according to any one of clauses 35-40, wherein the subject is human.

42. A pharmaceutical composition comprising a therapeutically effective amount of a compound of any one of clauses 1 to 28 and a pharmaceutically acceptable vehicle.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A pharmaceutical composition comprising a therapeutically effective amount of a RAS modulating compound of the formula:

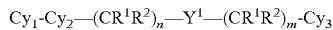

$Cy_1$-$Cy_2$—$(CR^1R^2)_n$—$Y^1$—$(CR^1R^2)_m$-$Cy_3$ wherein:

Cy1 is a cyclic group selected from an oxadiazole and a thiadiazole;

Cy2 is a phenyl;

Cy3 is a pyrazole, wherein Cy1, Cy2 and Cy3 are optionally further substituted;

n and m are each independently 0, 1, 2, 3, 4, 5 or 6, wherein n+m is less than 7; each R1 and each R2 is independently H, an alkyl or a substituted alkyl; and Y1 is selected from —CONR—, —NRCO—, —NRSO2- and —SO2NR— wherein R is H, an alkyl or a substituted alkyl;

or a salt thereof, and a pharmaceutically acceptable vehicle.

2. The pharmaceutical composition according to claim 1, wherein the compound is of the formula:

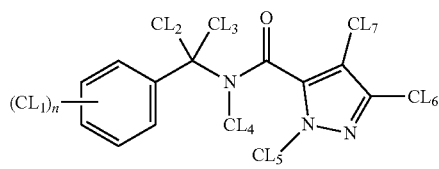

wherein:

CL1 is Cy1;

CL6 and CL7 are each independently selected from hydrogen, halogen, —CN, —NO2, —OH, —ORa, —C(O)Ra, —CO2Ra, —O(CO)Ra, —C(O)NRaRb, —SRa, —SO2Ra, —SO2NRaRb, —NRaRb, —NRaC(O)Rb, —NRaC(O)2Rb, —NRaSO2Rb, —NRa(CO)NRbRc, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, unsubstituted or substituted 3- to 10-membered heterocyclyl; wherein Ra, Rb and Rc are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, and unsubstituted or substituted aryloy-C1-4 alkyl; or two of Ra, Rb together or Ra and Rc together with the atom(s) to which they are attached, may form an unsubstituted or substituted 5-, 6- or 7-membered ring;

n is 1; and

CL2, CL3, CL4 and CL5 are each independently selected from hydrogen, alkyl and substituted alkyl.

3. The pharmaceutical composition according to claim 1, wherein the compound is of the formula:

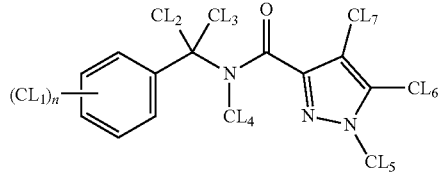

wherein:

CL1 is Cy1;

CL6 and CL7 are each independently selected from hydrogen, halogen, —CN, —NO2, —OH, —ORa, —C(O)Ra, —CO2Ra, —O(CO)Ra, —C(O)NRaRb, —SRa, —SO2Ra, —SO2NRaRb, —NRaRb, —NRaC(O)Rb, —NRaC(O)₂Rb, —NRaSO2Rb, —NRa(CO)NRbRc, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, unsubstituted or substituted 3- to 10-membered heterocyclyl; wherein Ra, Rb and Rc are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, and unsubstituted or substituted aryloy-C1-4 alkyl; or two of Ra, Rb together or Ra and Rc together with the atom(s) to which they are attached, may form an unsubstituted or substituted 5-, 6- or 7-membered ring;

n is 1; and

CL2, CL3, CL4 and CL5 are each independently selected from hydrogen, alkyl and substituted alkyl.

4. The pharmaceutical composition according to claim 2, wherein the compound has a structure corresponding to the formula:

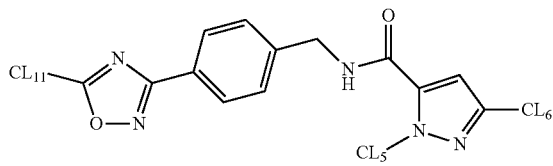

wherein:

CL11 is selected from hydrogen, halogen, —CN, —NO2, —OH, —ORa, —C(O)Ra, —CO2Ra, —O(CO)Ra, —C(O)NRaRb, —OC(O)NRaRb, —SRa, —SORa, —SO2Ra, —SO2NRaRb, —NRaRb, —NRaC(O)Rb, —NRaC(O)₂Rb, —NRaSO2Rb, —NRa(CO)NRbRc, unsubstituted or substituted C1-8 alkyl, unsubstituted or substituted C2-8 alkenyl, unsubstituted or substituted C2-8 alkynyl, unsubstituted or substituted C3-8 cycloalkyl, unsubstituted or substituted C3-10 aryl, unsubstituted or substituted 5- to 10-membered heteroaryl, unsubstituted or substituted 3- to 10-membered heterocyclyl; wherein Ra, Rb and Rc are each independently selected from hydrogen, unsubstituted or substituted C1-6 haloalkyl, unsubstituted or substituted C1-6 alkyl, unsubstituted or substituted C3-6 cycloalkyl, unsubstituted or substituted C2-6 alkenyl, unsubstituted or substituted C2-6 alkynyl, unsubstituted or substituted C6-10 aryl, unsubstituted or substituted 5- to 10-membered heteroaryl, unsubstituted or substituted aryl-C1-4 alkyl, and unsubstituted or substituted aryloy-C1-4 alkyl; or two of Ra, Rb together or Ra and Rc together with the atom(s) to which they are attached, may form an unsubstituted or substituted 5-, 6- or 7-membered ring.

5. The pharmaceutical composition according to claim 3, wherein the compound is of the formula:

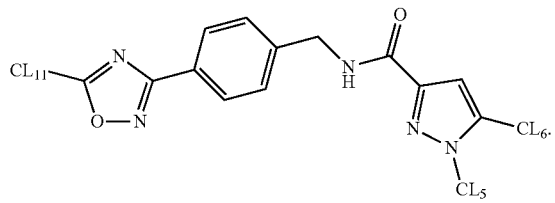

6. The pharmaceutical composition according to claim 4, wherein the compound has the following structure:

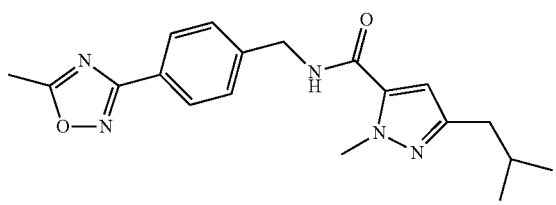

7. The pharmaceutical composition according to claim 2, wherein the compound has the following structure:

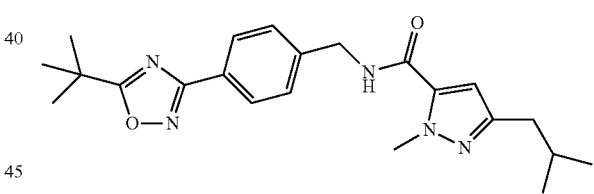

8. A method of modulating the activity of a target RAS in a sample, the method comprising:
contacting a sample comprising a target RAS with an effective amount of the pharmaceutical composition of claim 1 to modulate the activity of the target RAS.

9. A method of treating a subject for a RAS driven disease, the method comprising administering to the subject a therapeutically effective amount of the pharmaceutical composition of claim 1.

* * * * *